United States Patent [19]
Dean et al.

[11] Patent Number: 6,140,085
[45] Date of Patent: Oct. 31, 2000

[54] GENETIC CONTROL OF FLOWERING

[75] Inventors: Caroline Dean; Richard Colin Macknight; Ian Bancroft; Clare Katharine Lister, all of Norwich, United Kingdom

[73] Assignee: Plant BioScience Limited, Norwich, United Kingdom

[21] Appl. No.: 08/973,273

[22] PCT Filed: Jun. 3, 1996

[86] PCT No.: PCT/GB96/01332

§ 371 Date: Dec. 1, 1997

§ 102(e) Date: Dec. 1, 1997

[87] PCT Pub. No.: WO96/38560

PCT Pub. Date: Dec. 5, 1996

[30] Foreign Application Priority Data

Jun. 2, 1995 [GB] United Kingdom .................... 9511196

[51] Int. Cl.$^7$ .................................................. C12P 19/34
[52] U.S. Cl. ...................... 435/91.2; 435/320.1; 435/419; 536/23.1; 536/24.1; 800/278; 800/286; 800/287; 800/290
[58] Field of Search ................................. 435/320.1, 4, 5, 435/6, 91.2, 419, 466, 469, 471; 536/23.1, 24.1; 800/278, 285, 286, 287, 290

[56] References Cited

PUBLICATIONS

Putterill et al. Cell. vol. 80, pp. 847–857, Mar. 24, 1995.
Lee et al. The Plant Cell. vol. 6, pp. 75–83, Jan. 1994.
JP4258292 Abstract of Gene expressing at floral differentiation for flowering control–obtained from cluture of floral axis epithelium cells, Sep. 14, 1992.
Bancroft et al, "The Development of Systems for the Isolation of Gene from *Arabidopsis–thaliana* by Chromosome Walking in YAC Libraries Towards the Isolation of the Floral Induction Gene FCA", J Exp Bot 42(238 Suppl.):48 (1991).
Chandler et al, "Factors influencing the vernalization response and flowering time of late flowering mutants of *Arabidopsis thaliana* (L.) Heynh", Journal of Experimental Botany 45(278):1279–1288, (1994) & Westphal, et al, "Cloning FCA, a late–flowering locus of *Arabidopsis thaliana* (L.) Heynh", Third International Congress of Plant Molecular Biology: Molecular Biology of Plant Growth and Development, Tucson, Arizona, Abstract No. 508 (1991).
Newman et al, "5292 *Arabidopsis thaliana* cDNA clone 110C13T7", EMBL Sequence Database, Rel.42, Jan. 31, 1995, Accession No. T42029.
Wilson et al, "Analysis of the molecular basis of vernalization in *Arabidopsis thaliana*", Semin. Cell Dev. Biol. 7(3):435–440 (1996).
MacKnight et al, "Characterisation of the Arabidopsis FCA gene: Required for the early transition to flowering", Journal of Experimental Botany 47(Suppl.):7 (1996).
Koornneef et al, "A genetic and physiological analysis of late flowering mutants in *Arabidopsis thaliana*", Molecular and General Genetics 229:57–66 (1991).

Lee et al, "Isolation of Luminidependens: a gene involved in the control of flowering time in Arabidopsis", The Plant Cell 6 (1):75–83 (1994).
Putterill et al, "The Constans Gene of Arabidopsis Promotes Flowering and Encodes a Protein Showing Similarities to Zinc Finger Transcription Factors", Cell 80:847–857 (1995).
Database WPI Section Ch, Week 9243 Derwent Publications Ltd., London, GB; Class C06, An 92–354683 & JP,A,04 258 292 (Japan Tobacco Inc), Sep. 14, 1992 see abstract.
An et al, "Regulatory genes controlling flowering time or floral organ development", Plant Molecular Biology 25:335–337 (1994).
Grill et al, "Construction and characterization of a yeast artificial chromosome library of Arabidopsis which is suitable for chromosome walking", Molecular and General Genetics 226:484–490 (1991).
Putterill et al, "Chromosome walking with YAC clones in Arabidopsis: isolation of 1700 kb of contiguous DNA on chromosome 5, including a 300 kb region containing the flowering–time gene CO", Molecular and General Genetics 239:145–157 (1993).
MacKnight et al, "FCA, a Gene Controlling Flowering Time in Arabidopsis, Encodes a Protein Containing RNA–Binding Domains", Cell 89:737–745 (1997).
MacKnight et al, "Cloning and Analysis of FCA—A Gene Controlling Flowering Time in Arabidopsis", Cold Spring Harbor Meeting Abstracts, p. 77, Sep. 1995.
Dean et al, "Control of Flowering Time in Arabidopsis", International Society for Plant Molecular Biology Abstracts, No. 7, Sep. 1997.
Dean et al, "The FCA gene, Involved in Controlling the Floral Transition, Encodes a Putative RNA–Binding Protein and is itself Alternatively Spliced", 7$^{th}$ International Conference on Arabidopsis Research Abstracts, No. S32, Jun. 1996.
MacKnight et al, "Characterisation of the Arabidopsis FCA Gene—Required for the Early Transition to Flowering", 7$^{th}$ International Conference on Arabidopsis Research Abstracts, No. P69, Jun. 1996.
Instruction Manual—Hybond™–N+; positively charged nylon membrane, Version 2.0, Amersham Life Science, Amersham International plc (1992).
Hicks et al, "The Photoperiod–insensitive Early Flowering 3 mutant is Conditionally Defective in Circadian Regulated Processes", 7$^{th}$ International Conference on Arabidopsis Research Abstracts, S33, Jun. 1996.
Alonso–Blanco et al, "Mapping Quantitative Trait Loci for Seed Traits and Flowering Time by Means of Ler/CVI Recombinant Inbred Lines and AFLP Markers", 7$^{th}$ International Conference on Arabidopsis Research Abstracts, No. P70, Jun. 1996.

*Primary Examiner*—Remy Yucel
*Attorney, Agent, or Firm*—Nixon & Vanderhye P.C.

[57] ABSTRACT

FCA genes of *Arabidopsis thaliana* and *Brassica napus* are provided, enabling flowering characteristics, particularly timing of flowering, to be influenced in transgenic plants. Timing of flowering may be delayed or hastened using sense and antisense expression, also various mutants and alleles, including alternatively spliced forms.

51 Claims, 26 Drawing Sheets

Figure 1

```
   1  gatctaggtg aaattaatct gaagtttaga aatagatttt cttggaactt
  51  cggagaaaat atgcttcact caactttttt ttggtgctat atgaacaaag
 101  ataatggtca tatgaatgta aacgtgtttt gggatgatgt tatcttgttc
 151  catagatgcg gttggaagaa ttgcatttgg actgcaaaaa ctgatggcct
 201  ttatctttgg aattcagcga gcggtgaaga tgtattgtca agaaaatggg
 251  aagttggatg gtgaagccat attttttgctt ttgggtaatt ttttagtaca
 301  tgtatcttgt tgttttggc aaaaaaaaa ttgaaataat aaaaaacatt
 351  tgttttaact ttctctctta ttttgtgtat ttttcatcaa tgatagattt
 401  tttgttttag ttctttattt ataggtcatt taattattag attaatttcc
 451  tgagataata agatcataga ttaaataaca atattgtgtt tgtgatatat
 501  agagattaca ttttacactt atatatagtg gtaagatttc ttttgcttt
 551  caaaccatta aaaacctgtt aaacgattaa cttgactcaa gacaaagcca
 601  ttgattattg actcatgaat ctagtgactc atgatgaagg agacgaacag
 651  taaatattca tttgattatt ttaggtaaaa ggtagttcag acctagtcat
 701  atatcctcta aattcatata gtgatgcaag tattttgcat tacttagaac
 751  tttatattat tgatcaccca acacatgatt taataaacgc catgaaatgc
 801  atgtactata tcaaaatgtt tctgaagcat atagttgaca tgagaatttt
 851  ggattggact taagaatgtg agagttacct gaaatgtcaa tttttttccc
 901  tttgttaacg aaaactcatt ggaacaattg tatccccctt ttggcagtat
 951  ataaatatat tgatggccca agtagctgta ttttccgtta tcagccaaga
1001  ctcaataaag tctaccggtc caaatttcaa ctgaatcacc ggtccaacca
1051  ctattaccgt aactagaccg cttttttcttt tttacattcg gacaaaaaaa
1101  tcaaaatttc gagcaactaa attgatctca tcttcaatcA AATTCATCAT
1151  CTTCGATACT CGTTTCTTCT CTCTTTGGTT TCATACAGAT CCCAAATTTC
1201  TAGGGCTCCT AGTCCTTTGA TTTCTTCGAC TGGAATCGCA ATTCCCCACT
1251  ACGTCAAGCT GGACAGACAC CGAAGGGATC GCCATGAGAG TGGCGGCTAC
1301  GAGGATTCCT ACCATAACCA CCGAGCCCAT CCCAGAGGTC CATCTCGTCC
1351  CTCAGATTCA CGCTTCGAAG AGGATGATGA TGATTTTCGC CGCCACCGTC
1401  GTCGTCGTGG AAGCAGCCCT AGCAATTATC GAATTGGAAT TGGGGGCGGA
```

Figure 1 Continued

```
1451 GGAGGAGGTA ATGGTGGTCG ACGCTGGGAA GATGACACTC CTAAGGATTT
1501 TGATGGTCCC GGAGATGGAG GTTTCCGGCA G[ATG]AATGGT CCCCCAGATA
1551 GAGTAGATTT TAAGCCT[ATG] GGTCCTCACC ATGGTGGAAG TTTTCGGCCT
1601 [ATG]GGGTTTG CCTACGATGA TGGTTTTCGT CCAATGGGTC CTAACGGTGG
1651 TGTGGGAGGA GAAGGGACAC GGTCAATTGT TGGAGCTCGG TATAACTATC
1701 CCGCGAAGTA TCCTCCTTCA GAGAGTCCAG ACAGGAGGAG ATTTATCGGT
1751 AAAGCAATGG AGTCTGATTA TTCTGTAAGA CCGACTACAC CGCCGGTCCA
1801 GCAGCCTCTT TCCGGTCAGA AAGAGGGTA TCCTATCTCA GACCATGGCA
1851 GCTTTACTGG AACTGgtaag catgagttca ctcttctttc ttctatgtat
1901 atttattctt gtagtctgtt aaggttcctg agtgtctctt attttgtgg
1951 gaatcaatga ttagagtatt gaaggtagt atggttgtta tgttactgta
2001 ttgttgaagg tttttcatgg gatcgactct agaggatcct ttcgattttc
2051 ccatgtatgt gataatcaaa actatatgcc atcttcatgt gtatccttat
2101 ctggttaatt tgatttgcag ATGTCTCTGA TCGTAGCAGT ACAGTCAAGC
2151 TTTTTGTTGG ATCTGTACCA AGGACAGCTA CAGAAGAAGA Agtgagttaa
2201 tcttggaaat cattgttatc tatatactca ttactgagaa cctttctaa
2251 attttttctg ttggttttca tattgtagAT CCGTCCCTAT TTCAACAGC
2301 ATGGAAATGT TCTGGAGGTT GCTCTGATCA AGGACAAGAG AACTGGACAG
2351 CAGCAAGgta tgtcaatctc cattttatta ggaaatagtc gtgaattata
2401 cttttaaaa tttcaggtct ccctgaaaag gctgatggga agcaacccca
2451 gtctcatcat tggcctccaa ttgtttgcaa caattttcgg gcttattgct
2501 tatgcttgcc agcgtcttat ctgtgttcga ttctgtcaca gaagaaggct
2551 acctgtgcta agaagggtt tatgtactta tgttgggcaa atagatttcg
2601 ctacttgtgt gtattctaga actttagatg tgtttgaaaa gtgtagaatt
2651 tattgagggt gttttagagt tggagttaat gtacagagaa ctgaattttg
2701 ctgttgcctt tatagtggga attggttata agaacatcgc tattttcctc
2751 tcctattgaa attcattttc tttactcttc ctctagatgg attgaagatg
2801 ttgtatgg tcttgacagg atgaatgtat tttttaagt tggtagtttg
2851 ataaggacat gaggttcaaa agatggtttc ttgatttgcc actcctgctg
2901 gtcaaagatt tggccgtctt tctaatttta tcatgttgga ggtttggcgt
```

Figure 1 Continued

```
2951  cttcattttc tttcatatca atttatgggt gtgctgtcta ttggttaatg
3001  atggcattcc ttttaccttt ttggatgagt gatgctggaa tgaatgcgtt
3051  tctccttttc ttttgttgat ggcctgagga actatgatgg ctatatttct
3101  ttccactctc tttgaatggc ctgaaatgtg tgctttctgt atggtcgtcc
3151  ctctcaattt cttggatggc ttgtgatgtg ataccatc tctcgtcata
3201  ggtgaatgaa tgatttgttt agtagttctt atgtatgtat tttgtatgtt
3251  cccacgtctc tattccttgg atggcttgtg atgtgatata ccatctctcg
3301  tcatagatga atgaatattt tgttgagtag ctcttatgtc tgtatggtgg
3351  cccttgcagt gctgatcgat atttatgtgg aagaaatgtt tgatgataga
3401  ttttttttgt atgctccctt ttcgctaatc aagcctttgt gcttgcaagg
3451  tgcaactgtt attttattat tgaatttcct gttctactac tccatttagt
3501  tctgtctcta ttttgtcagt gtgaagaaat actagacgat gaatggtgtg
3551  tttgtacgtg catagttatt tataaattct tgactttcca agaagttatt
3601  atttctataa ctgctacacc tttgtggatg gcagaacaaa tgcatctgat
3651  tgtggtgaca taaacacttt tgatcgcggt tgaatgtact agattccata
3701  caactctttc ttcagccttg tgaaatatta ttatgttagg tggtgcaaac
3751  atatggaagg aacctgattg ttttagtttc ttagaatagt ttctgatgtt
3801  aatacagcat gttgacttca ctctcttgcc cttgatcaat cagcatcagg
3851  caggggccta attatgtatt acatgaagca atcgtattct tttctgaatt
3901  agatttttt ccaatgagtt atcttgccca taactgtagt tctttatttg
3951  aagtcttcaa atgcttgatg tatggtgacg aaaatgtgta tatgttttgg
4001  ttttgattat ccgctactca tcaattattg agattcttac atactgaatc
4051  cgttactttg gacctatagt tatgttttat gttgctaatt aacttgtaca
4101  tgtttctaga ttttctttca aatggatcct gcttggacaa atgcagccac
4151  cctttgtctg aaaggccctc ttgtagatat gttatctgca gatactgact
4201  gtgttcaatt ttttaatatt tgttttttgcc atattctcca tttgaagaca
4251  ttaattactt ctctccaaca acttacatc aatatttaag tggaggctgt
4301  cagacatgtc ttatgatttt cctactgaac ttatgtgctt tgagtagtac
4351  atcttgttac tagtacaatt tgatggtaga aggaaaagtt gaaccctgaa
4401  acagatagct taagtatcag tctttaatgc agGCTGTTGT TTTGTAAAAT
4451  ATGCAACTTC GAAAGATGCG GATAGAGCCA TCAGAGCACT GCACAATCAG
```

Figure 1 Continued

```
4501   ATCACTCTTC CTGGGgtaat taccctgagg cttctctta tcaagaacag
4551   gaaactatag gttgtttcac cttttataat tttgttgatt cccagGGAAC
4601   TGGTCCTGTT CAAGTTCGAT ATGCTGACGG GGAGAGAGAA CGCATAGgta
4651   atcaacttcc acacagagta tctaatgtgg ctgtcattgt ctagtgttca
4701   tagccaagac catacgctgc ataagttcag attacaaaaa ttaagaaaat
4751   gtgggaaatg atatgaactt tatggatgtt gatccttttc tttccctgtt
4801   ttctttgcct tactatcaag tgatatagtt ctcttcttct gaagGCACCC
4851   TAGAGTTTAA GCTTTTTGTT GGTTCACTAA ACAAGCAAGC CACTGAAAAA
4901   GAAGTTGAGG AGgtatgttt cgtatcttac ttttgaagt tgttacttat
4951   gtcagattaa cggaacaggg aagagttcta aacttggata ttattgtgtc
5001   ccctgttacc tgagttgata attttaaatg actctttgat aaattttgtt
5051   agtcttacca aagggtgagt gtctagaaaa tctgtgtcaa taatgcaagc
5101   gcttggacat tctacttact gtgtaatctc ttcttccaat tgatccaact
5151   gtttgactgt cataatagat aaaattaata aatgtgaacg gctaccttcc
5201   cagttcaact tatgtgtttc aatttctcat gtaatctttt aacaaactgt
5251   tttattgtta ttgctttaac agATCTTTTT ACAATTTGGT CATGTGGAAG
5301   ATGTCTATCT CATGCGGGAT GAATATAGAC AGAGTCGTGg tatgttttgt
5351   aatttgtact agattctata aattatttgt tgtgtgatga tgttgagatg
5401   gtgaaactgt gttttcact ttgtagGATG TGGGTTTGTT AAATATTCAA
5451   GCAAAGAGAC GGCAATGGCA GCTATCGATG GTCTCAACGG AACTTATACC
5501   ATGAGAGtaa gctgtgaatc acataagtat ctcagtttct ctcattatca
5551   ccctttggac ctgttttgtt tactggcctc tatcctttcc ccagGGTTGC
5601   AATCAGCCAT TGATTGTTCG GTTTGCTGAG CCAAAGAGGC CTAAACCTGG
5651   CGAGTCAAGg taatgccttg ggtactatat tttgattaat cctaatactc
5701   ttatcaagta aattgtatat accttcattc tttgttctgt ctgagttata
5751   tttgtggaga atcttttgga catggtggag agttgggaac cctgttcctt
5801   ctccagttat tactggaatg tgaagcattg cttctagat atccttaagt
5851   agtttctgtt tccagGGAAA TGGCACCTCC TGTTGGACTT GGTTCAGGGC
5901   CTCGTTTTCA AGCTTCAGGA CCAAGgtaac tggtgtgaaa ggagatcatg
5951   attatgctca ttaggtaatt atatatgttg acttaccccg gtctcctcat
```

Figure 1 Continued

```
6001  ctctattcgt tagGCCTACC TCTAACTTTG GTGACTCTAG TGGGATGTA
6051  AGCCACACAA ATCCTTGGCG TCCAGCTACT TCACGAAACG TAGGCCCACC
6101  TAGTAACACT GGGATCCGTG GTGCCGGTAG TGACTTTCCC CCTAAACCAG
6151  gtcaagcaac attgccttca aatcaggtga gaacaggttg atgatcatgt
6201  atatcatctt aaatctgcac attcatataa gtaagcgcat agagtttgca
6251  tgtattgtgc gagacaaata aaagaaagt acttcatata ctgcacacat
6301  gggcttatga caggtgaaaa gaagcatgaa gttctgacct ttcaactttt
6351  catataatgc aacaaacacg atgtgtgttg ctcaaatgat atggcttaa
6401  tttgcagttt gtcagttact gaggcaattt ttttttgaa taatttctag
6451  ccctgatgtg agctttttta aatgtaacat tctatattgt tagGGTGGCC
6501  CGTTAGGTGG TTATGGTGTT CCTCCCCTTA ACCCTCTCCC AGTCCCTGGA
6551  GTTTCATCTT CTGCCACATT GCAACAGgta ctttagctat attttttccaa
6601  ttaagcaaat ctgaaaatgt tgtgatgatt aacttggatt ttcaattgtt
6651  tctattccat agCAAAATCG GGCAGCTGGC CAGCATATAA CACCATTAAA
6701  AAAACCTCTT CACAGTCCAC AGGGTCTCCC TCTCCCCCTC CGTCCGCAAA
6751  CTAATTTCCC TGGGGCCCAG GCACCCTTGC AGAATCCTTA TGCTTATAGC
6801  AGCCAGTTGC CTACCTCTCA GCTGCCACCA CAGCAAAACA TCAGTCGTGC
6851  AACTGCTCCT CAAACTCCTT TGAACATTAA TCTACGGCCA ACAACTGTGT
6901  CTTCTGCAAC TGTTCAATTT CCCCCTCGTT CCCAGCAGCA ACCGCTACAA
6951  AAGATGCAAC ATCCTCCTTC TGAGCTAGCT CAGCTCTTGT CGCAGCAAAC
7001  TCAGAGTCTA CAAGCAACAT TCCAATCGTC TCAGCAAGCA ATTTCTCAGC
7051  TGCAGCAGCA GGTGCAGTCT ATGCAGCAAC CAAACCAAAA TTTACCACTC
7101  TCACAGAATG GCCGAGCTGG TAAACAACAG gtatgaatat agtctctcag
7151  ttgcatctgc ccagacgggt tcttcagctg ctattgtgtt gttttaactt
7201  aaaattattt cctgatagac atcccgtttt ttatccttca tgtgttttag
7251  tattctcccc ttttctaatg ttcctctcgg ctgcttcttt atcagTGGGC
7301  TGGATCTGCA ATTCCAAGAG TGGCTAGCAC CACTGGTTCG ACACCAGTGA
7351  GCTATGTGCA AACAGCTGCA CCTGCAGTAA GTCAGAGCGT AGGTTCTGTC
7401  AAATGTACCT GGACCGAGCA TACCTCGCCT GATGGATTTA AATATTATTA
7451  CAATGGTCTA ACGGGTGAAA GCAAGgtgag aaacgtggtt cctcttaat
7501  atattttcctt gtgagttca ggagtattcc tcctggttta ttgtgctatt
```

Figure 1 Continued

```
7551 gataatcctt acacatgtat attttatatt tgaagtcctt cagtacgtgc
7601 catattatgt atataattca cttttgcagT GGGAAAAACC TGAGGAAATG
7651 ATAGTGTTCG AACGAGAGCA ACAGAAACAG CAACAACATC AAGAGAAGCC
7701 AACTATACAG CAGTCCCAGA CCCAATTACA GCCGTTGCAG CAACAACCAC
7751 AACAAGTTCA GCAGCAATAT CAGGGCCAGC AATTACAGCA GCCGTTTTAT
7801 TCTTCACTGg ttggtttcgt tttcatgctg gttacattca aatatttttg
7851 tcacatggtt tctaatttgc atatttactc ttgttcattt ggagttgcag
7901 TATCCAACTC CAGGGGCCAG CCATAATACT CAGgtgtata tctgtttaat
7951 ctgtttactt atttttcatt tcaagatttg attcttgata tgctaatctt
8001 gtggtagaag gagattgacc accttaaagt aaaattcagt agccatggtt
8051 ttgccagcat tttgaaatac agataacaaa tctctaacgt gaatgcctat
8101 tttcctttct aaaatgcagT ATCCATCATT GCCAGTAGGT CAAAATAGCC
8151 AGgtacatat ctgaatctgt ggacttattt ttcattgaac tgattgattc
8201 tcagttacaa cattgacttc ctctgatgcg tagttttgt aacatatcag
8251 aataacaaaa acttcatctg attcgtatat tctctggttg aaaatctttt
8301 tttcttttct ggaaaatgca gTTTCCTATG TCAGGAATTG GTCAGAATGC
8351 TCAGgtatat atctcatttt gtattaacaa tttcccatac cttctgtacc
8401 tttgaattta atcacagaac ataatgagtt cttggattta atgtcatttt
8451 aaaagaaac atcagtgata tgacttcctt ccttggttaa aaatggttta
8501 ggcagagctt attttctatt ctgtttggat tgtctagGAT TATGCTCGGA
8551 CACATATACC CGTGGGAGCT GCTTCAATGA ATGATATATC AAGAACTCCA
8601 CAGgtagtta tggttttat cagtgattca gaacttctct ctgttcataa
8651 ttcgtccttt ggtattcaga tgttcttttt cgttgaaacc gttttttcc
8701 ttaattctct ttacaatcat atctctttt cccagAGCCG TCAATCTCCC
8751 CAAGAACTCA TGTGGAAGAA TAAAGCTTGA Ggttcatatc taccctttct
8801 ctcctctctc ttgtattttc tccataccga aacacattcc aatgtatgtg
8851 gtttctttag ttgaagttac ctctgtgttg atcgatactc tacttcagGT
8901 ACATGAGACG AGGAGCTAAA CTATCTCAGT AGCTAGATAG AAATTTCTGG
8951 AACTAATTAG TCAAGGAGAG GAAAGCAGC AATGGTAGTG TCCTTAGTCT
9001 CTGATTTTTT TAGTTAACCC CTTCAGTTAT AATAGATAGG CGATCGTAGA
```

Figure 1 Continued

```
9051 CCATCTGCAT TCTATCTTTT CTCTAATCAG ATATCTCCTC CTTTTCCATT
9101 TTAAGAGCTG CCAAACAATG GCCTGTTGTA ACATAGCTAG CGCAAGTTAT
9151 GTCTCATGTT GTGTTACTAG TAGTAACTTA GCTGGGTAAA CCAAACTTTG
9201 ATCCAGATTA GGAGTCATAT ATAATTATAT AAATAGAATA TGTACATTCA
9251 TAGATAgctc atcacttata atgagactag atcttagcaa aatccaactc
9301 taattgtcat tttcagagat ctatcaattt gtagtttcct gatcttcata
9351 tatgtgttcg ctcttctaat gattacgtaa aatcagagtc ctacgtaggt
9401 ggacttcttt aatttttata tagataatta gatatcattc aataagtcgg
9451 gcttttattt ttagttaatc attctacaat tcttcctaat ctcgctatta
9501 ctaccaccgg gtatccctcc cattttaacc atagcgttct taaaatcctc
9551 aaagaaaacc gactgatctg ttgcgtaggt ctcaacaatc gcccttgtcc
9601 ctgggtcttg aaccgctaaa gcctggtctg atggaagcaa tccctcaccc
9651 gagaggaggt ttacatagta ctggttgtca aatgttgatg gagtcaccaa
9701 gtcaagctga gtgataccta cactgggccc aacagtcgag cataactgtt
9751 gcagtgactc gag
```

Figure 2

```
  1  MNGPPDRVDF KPMGPHHGGS FRPMGFAYDD GFRPMGPNGG VGGEGTRSIV
 51  GARYNYPAKY PPSESPDRRR FIGKAMESDY SVRPTTPPVQ QPLSGQKRGY
101  PISDHGSFTG TDVSDRSSTV KLFVGSVPRT ATEEEIRPYF EQHGNVLEVA
151  LIKDKRTGQQ QGCCFVKYAT SKDADRAIRA LHNQITLPGG TGPVQVRYAD
201  GERERIGTLE FKLFVGSLNK QATEKEVEEI FLQFGHVEDV YLMRDEYRQS
251  RGCGFVKYSS KETAMAAIDG LNGTYTMRGC NQPLIVRFAE PKRPKPGESR
301  DMAPPVGLGS GPRFQASGPR PTSNEGDSSG DVSHTNPWRP ATSRNVGPPS
351  NTGIRGAGSD FSPKPGQATL PSNQGGPLGG YGVPPLNPLP VPGVSSSATL
401  QQENRAAGQH ITPLKKPLHS PQGLPLPLRP ETNFPGGQAP LQNPYAYSSQ
451  LPTSQLPPQQ NISRATAPQT PLNINLRPTT VSSATVQFPR RSQQQPLQKM
501  QHPPSELAQL LSQQTQSLQA TFQSSQQAIS QLQQQVQSMQ QPNQNLPLSQ
551  NGRAGKQQWA GSAIPRVAST TGSTPVSYVQ TAAPAVSQSV GSVKCTWTEH
601  TSPDGFKYYY NGLTGESKWE KPEEMIVFER EQQKQQQHQE KPTIQQSQTQ
651  LQPLQQQPQQ VQQQYQGQQL QQPFYSSLYP TPGASHNTQY PSLPVGQNSQ
701  FPMSGIGQNA QDYARTHIPV GAASMNDISR TQQSRQSPQE LMWKNKT
```

Figure 3

```
   1    AAATTGATCT CATCTTCAAT CAAATTCATC ATCTTCGATA CTCGTTTCTT
  51    CTCTCTTTGG TTTCATACAG ATCCCAAATT TCTAGGGCTC CTAGTCCTTT
 101    GATTTCTTCG ACTGGAATCG CAATTCCCCA CTACGTCAAG CTGGACAGAC
 151    ACCGAAGGGA TCGCCATGAG AGTGGCGGCT ACGAGGATTC CTACCATAAC
 201    CACCGAGCCC ATCCCAGAGG TCCATCTCGT CCCTCAGATT CACGCTTCGA
 251    AGAGGATGAT GATGATTTTC GCCGCCACCG TCGTCGTCGT GGAAGCAGCC
 301    CTAGCAATTA TCGAATTGGA ATTGGGGGCG GAGGAGGAGG TAATGGTGGT
 351    CGACGCTGGG AAGATGACAC TCCTAAGGAT TTTGATGGTC CCGGAGATGG
 401    AGGTTTCCGG CAGATGAATG GTCCCCCAGA TAGAGTAGAT TTTAAGCCTA
 451    TGGGTCCTCA CCATGGTGGA AGTTTTCGGC TATGGGGTT  TGCCTACGAT
 501    GATGGTTTTC GTCCAATGGG TCCTAACGGT GGTGTGGGAG GAGAAGGGAC
 551    ACGGTCAATT GTTGGAGCTC GGTATAACTA TCCCGCGAAG TATCCTCCTT
 601    CAGAGAGTCC AGACAGGAGG AGATTTATCG GTAAAGCAAT GGAGTCTGAT
 651    TATTCTGTAA GACCGACTAC ACCGCCGGTC CAGCAGCCTC TTTCCGGTCA
 701    GAAAAGAGGG TATCCTATCT CAGACCATGG CAGCTTTACT GGAACTGATG
 751    TCTCTGATCG TAGCAGTACA GTCAAGCTTT TGTTGGATC  TGTACCAAGG
 801    ACAGCTACAG AAGAAGAAAT CCGTCCCTAT TTCGAACAGC ATGGAAATGT
 851    TCTGGAGGTT GCTCTGATCA AGGACAAGAG AACTGGACAG CAGCAAGGTA
 901    TGTCAATCTC CATTTTATTA GGAAATAGTC GTGAATTATA CTTTTTAAAA
 951    TTTCAGGTCT CCCTGAAAAG GCTGATGGGA AGCAACCCCA GTCTCATCAT
1001    TGGCCTCCAA TTGTTTGCAA CAATTTTCGG GCTTATTGCT TATGCTTGCC
1051    AGCGTCTTAT CTGTGTTCGA TTCTGTCACA GAAGAAGGCT ACCTGTGCTA
1101    AGAAAGGGTT TATGTACTTA TGTTGGGCAA ATAGATTTCG CTACTTGTGT
1151    GTATTCTAGA ACTTAGATG  TGTTTGAAAA GTGTAGAATT TATTGAGGGT
1201    GTTTTAGAGT TGGAGTTAAT GTACAGAGAA CTGAATTTTG CTGTTGCCTT
1251    TATAGTGGGA ATTGGTTATA AGAACATCGC TATTTTCCTC TCCCTATTGA
1301    AATTCATTTT CTTTACTCTT CCTCTAGATG GATTGAAGAT GTTGTGTATG
```

Figure 3 Continued

```
1351  GTCTTGACAG GATGAATGTA TTTTTTTAAG TTGGTAGTTT GATAAGGACA
1401  TGAGGTTCAA AAGATGGTTT CTTGATTTGC CACTCCTGCT GGTCAAAGAT
1451  TTGGCCGTCT TTCTAATTTT ATCATGTTGG AGGTTTGGCG TCTTCATTTT
1501  CTTTCATATC AATTTATGGG TGTGCTGTCT ATTGGTTAAT GATGGCATTC
1551  CTTTTACCTT TTTGGATGAG TGATGCTGGA ATGAATGCGT TTCTCCTTTT
1601  CTTTTGTTGA TGGCCTGAGG AACTATGATG GCTATATTTC TTTCCACTCT
1651  CTTTGAATGG CCTGAAATGT GTGCTTTCTG TATGGTCGTC CCTCTCAATT
1701  TCTTGGATGG CTTGTGATGT GATATACCAT CTCTCGTCAT AGGTGAATGA
1751  ATGATTTGTT TAGTAGTTCT TATGTATGTA TTTTGTATGT TCCCACGTCT
1801  CTATTCCTTG GATGGCTTGT GATGTGATAT ACCATCTCTC GTCATAGATG
1851  AATGAATATT TGTTGAGTA GCTCTTATGT CTGTATGGTG GCCCTTGCAG
1901  TGCTGATCGA TATTTATGTG GAAGAAATGT TGATGATAG ATTTTTTTG
1951  TATGCTCCCT TTCGCTAAT CAAGCCTTTG TGCTTGCAAG GTGCAACTGT
2001  TATTTATTA TTGAATTTCC TGTTCTACTA CTCCATTTAG TTCTGTCTCT
2051  ATTTGTCAG TGTGAAGAAA TACTAGACGA TGAATGGTGT GTTTGTACGT
2101  GCATAGTTAT TTATAAATTC TTGACTTTCC AAGAAGTTAT TATTTCTATA
2151  ACTGCTACAC CTTTGTGGAT GGCAGAACAA ATGCATCTGA TTGTGGTGAC
2201  ATAAACACTT TGATCGCGG TTGAATGTAC TAGATTCCAT ACAACTCTTT
2251  CTTCAGCCTT GTGAAATATT ATTATGTTAG GTGGTGCAAA CATATGGAAG
2301  GAACCTGATT GTTTTAGTTT CTTAGAATAG TTTCTGATGT TAATACAGCA
2351  TGTTGACTTC ACTCTCTTGC CCTTGATCAA TCAGCATCAG GCAGGGGCCT
2401  AATTATGTAT TACATGAAGC AATCGTATTC TTTTCTGAAT TAGATTTTTT
2451  TCCAATGAGT TATCTTGCCC ATAACTGTAG TTCTTTATTT GAAGTCTTCA
2501  AATGCTTGAT GTATGGTGAC GAAAATGTGT ATATGTTTTG GTTTTGATTA
2551  TCCGCTACTC ATCAATTATT GAGATTCTTA CATACTGAAT CCGTTACTTT
2601  GGACCTATAG TTATGTTTTA TGTTGCTAAT TAACTTGTAC ATGTTTCTAG
2651  ATTTTCTTTC AAATGGATCC TGCTTGGACA AATGCAGCCA CCCTTTGTCT
2701  GAAAGGCCCT CTTGTAGATA TGTTATCTGC AGATACTGAC TGTGTTCAAT
2751  TTTTTAATAT TGTTTTTGC CATATTCTCC ATTTGAAGAC ATTAATTTAT
```

Figure 3 Continued

```
2801 TCTCTCCAAC AACTTTACAT CAATATTTAA GTGGAGGCTG TCAGACATGT
2851 CTTATGATTT TCCTACTGAA CTTATGTGCT TTGAGTAGTA CATCTTGTTA
2901 CTAGTACAAT TTGATGGTAG AAGGAAAAGT TGAACCCTGA AACAGATAGC
2951 TTAAGTATCA GTCTTTAATG CAGGCTGTTG TTTTGTAAAA TATGCAACTT
3001 CGAAAGATGC GGATAGAGCC ATCAGAGCAC TGCACAATCA GATCACTCTT
3051 CCTGGGGGAA CTGGTCCTGT TCAAGTTCGA TATGCTGACG GGAGAGAGA
3101 ACGCATAGGC ACCCTAGAGT TTAAGCTTTT TGTTGGTTCA CTAAACAAGC
3151 AAGCCACTGA AAAGAAGTT GAGGAGATCT TTTTACAATT TGGTCATGTG
3201 GAAGATGTCT ATCTCATGCG GGATGAATAT AGACAGAGTC GTGGATGTGG
3251 GTTTGTTAAA TATTCAAGCA AAGAGACGGC AATGGCAGCT ATCGATGGTC
3301 TCAACGGAAC TTATACCATG AGAGGTTGCA ATCAGCCATT GATTGTTCGG
3351 TTTGCTGAGC CAAAGAGGCC TAAACCTGGC GAGTCAAGGG ACATGGCACC
3401 TCCTGTTGGA CTTGGTTCAG GGCCTCGTTT TCAAGCTTCA GGACCAAGGC
3451 CTACCTCTAA CTTTGGTGAC TCTAGTGGGG ATGTAAGCCA CACAAATCCT
3501 TGGCGTCCAG CTACTTCACG AAACGTAGGC CCACCTAGTA ACACTGGGAT
3551 CCGTGGTGCC GGTAGTGACT TTTCCCCTAA ACCAGGTCAA GCAACATTGC
3601 CTTCAAATCA GGGTGGCCCG TTAGGTGGTT ATGGTGTTCC TCCCCTTAAC
3651 CCTCTCCCAG TCCCTGGAGT TTCATCTTCT GCCACATTGC AACAGGAAAA
3701 TCGGGCAGCT GGCCAGCATA TAACACCATT AAAAAAACCT CTTCACAGTC
3751 CACAGGGTCT CCCTCTCCCC CTCCGTCCGG AAACTAATTT CCCTGGGGGC
3801 CAGGCACCCT TGCAGAATCC TTATGCTTAT AGCAGCCAGT TGCCTACCTC
3851 TCAGCTGCCA CCACAGCAAA ACATCAGTCG TGCAACTGCT CCTCAAACTC
3901 CTTTGAACAT TAATCTACGG CCAACAACTG TGTCTTCTGC AACTGTTCAA
3951 TTTCCCCCTC GTTCCCAGCA GCAACCGCTA CAAAAGATGC AACATCCTCC
4001 TTCTGAGCTA GCTCAGCTCT TGTCGCAGCA AACTCAGAGT CTACAAGCAA
4051 CATTCCAATC GTCTCAGCAA GCAATTTCTC AGCTGCAGCA GCAGGTGCAG
4101 TCTATGCAGC AACCAAACCA AAATTTACCA CTCTCACAGA ATGGCCGAGC
4151 TGGTAAACAA CAGTGGGCTG GATCTGCAAT TCCAAGAGTG GCTAGCACCA
```

Figure 3 Continued

```
4201  CTGGTTCGAC ACCAGTGAGC TATGTGCAAA CAGCTGCACC TGCAGTAAGT
4251  CAGAGCGTAG GTTCTGTCAA ATGTACCTGG ACCGAGCATA CCTCGCCTGA
4301  TGGATTTAAA TATTATTACA ATGGTCTAAC GGGTGAAAGC AAGTGGGAAA
4351  AACCTGAGGA AATGATAGTG TTCGAACGAG AGCAACAGAA ACAGCAACAA
4401  CATCAAGAGA AGCCAACTAT ACAGCAGTCC CAGACCCAAT TACAGCCGTT
4451  GCAGCAACAA CCACAACAAG TTCAGCAGCA ATATCAGGGC CAGCAATTAC
4501  AGCAGCCGTT TTATTCTTCA CTGTATCCAA CTCCAGGGGC CAGCCATAAT
4551  ACTCAGTATC CATCATTGCC AGTTGGTCAA AATAGCCAGT TTCCTATGTC
4601  AGGAATTGGT CAGAATGCTC AGGATTATGC TCGGACACAT ATACCCGTGG
4651  GAGCTGCTTC AATGAATGAT ATATCAAGAA CTCAACAGAG CCGTCAATCT
4701  CCCCAAGAAC TCATGTGGAA GAATAAAACT TGAGGTACAT GAGACGAGGA
4751  GCTAAACTAT CTCAGTAGCT AGATAGAAAT TTCTGGAACT AATTAGTCAA
4801  GGAGAGGAAA AGCAGCAATG GTAGTGTCCT TAGTCTCTGA TTTTTTTAGT
4851  TAACCCCTTC AGTTATAATA GATAGGCGAT CGTAGACCAT CTGCATTCTA
4901  TCTTTCTCT AATCAGATAT CTCCTCCTTT TTCATTTTAA GAGCTGCCAA
4951  ACAATGGCCT GTTGTAACAT AACTAGCGCA AGTTATGTCT CATGTTGTGT
5001  TACTAGTAGT AACTTAGCTG GGTAAACCAA ACTTTGATCC AGATTAGGAG
5051  TCATATATAA TTATATAAAT AGAATATGTA CATTCATAGA TAAAAAAAAA
5101  AAAAAAAAAA AAA
```

Figure 4

RNA Binding Domain

```
Protein  Domain                       RNP 2                                                    RNP 1
fca      1       DVSDRSSTVK   LFVGSV  PRTATEEIRPYFEQHGNVLEVALIKDKRTGQQ  QGCCFVKY  ATSKDADRAIRALHNQITLPG
fca      2       RERIGTLEFK   LFVGSL  NKQATEKEVEEIFLQFGHVEDVYLMRDEYRQS  RGCGFVKY  SSKETAMAAID    GLNQ
Sex lethal 1     MNDPRASNTN   LIVNYL  PQDMTDRELYALFRAIGPINTCRIMRDY      KTGYSFGY  AFVDFTSEMDSQRAIKVLNG
         2       PGGESIKDTN   LYVTNL  PRTITDDQLDTIFGKYGSIVQKNILRDKLTGRP RQVAFVRY  NKREEAQEAISALNNVIPEGG
cra-2    1       SREHPQASRC   IGVFGL  NTNTSQHKVRELFNKYGPIERIQMVIDAQTQRS RGFCFIYF  EKLSDARAAKD  SCSQIEVDG LFVGNL                             B   Y   F  FG  I  K  RGFGFVXF  A            L G
                             IYIKG                              D          Y   Y  R  R  XA   Y                I
```

Homology in C-terminal region

```
fca          HTEHTSPDGFKYYYNGLTGESKNEKPEEMIVFEREQ
Yeast        WKEAKDASGRIYYYNTLTKKSTWEKPKELISQEELL
C.elegans    WKEFMSDDGKFYYYNTLTKKTQHVKPDGEEITKGEQ

W E     G   YYYN LT       W  KP
```

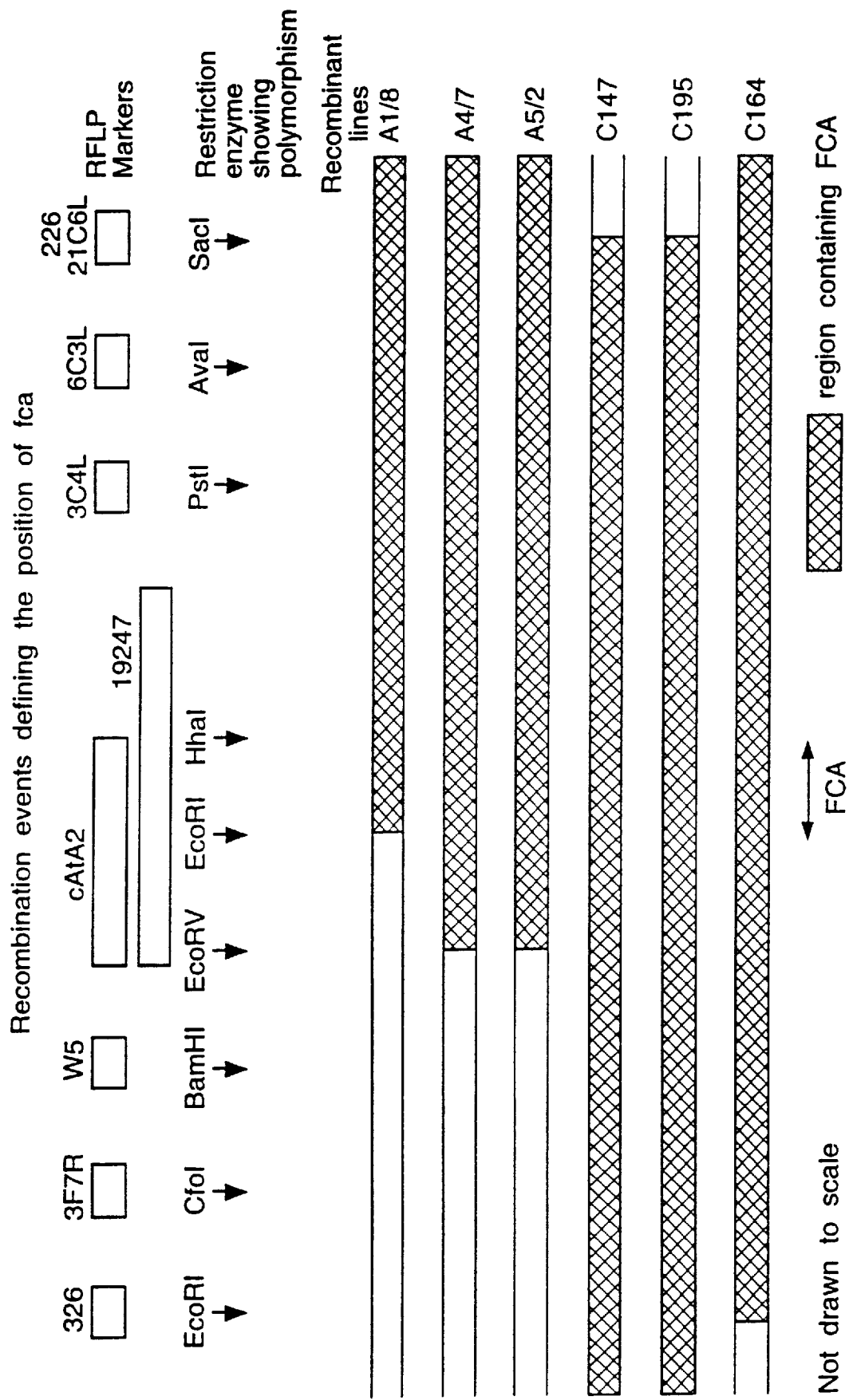

COMPLEMENTING COSMIDS IN FCA REGION

| Cosmid | No. transformants complementing | No. transformants generated |
|---|---|---|
| cAtB1 | 5 | 5 |
| cAtA2 | 3 | 4 |
| CL44B23 | 7 | 8 |
| CL58I16 | 6 | 11 |
| CL13E22 | 0 | 4 |
| CL46I1 | 0 | 1 |
| CL32J12 | 0 | 4 |
| CL18F7 | 0 | 4 |
| CL59F17 | 0 | 2 |
| CL26C17 | 0 | 2 |
| CL56K7 | 0 | 4 |

Figure 8a

```
   1  GTTAACGGAT CACACAGTAT AATATAAAAC TAGGTGTTTT GCCCGCACAT
  51  GCGAGCATAA TTTTCTCATC AATACTTATT AGTTTATATC TTATTAATCT
 101  AAAACCAGCA TGATAAGTTA TTATTTATGT TTTCAGATAG TTAAATCAAA
 151  CATCAAAGTA TTTATATATG TCAAATATTT TATCAAAAAT ATATACTTAT
 201  TATTGTGTTA AATTTTTTAA AACACTCATA TCTTAGAAAT AGTTTAGAAA
 251  ATATCTTTAT ATAAATGTTT TTTAACTTTT ATAATAAAAA TATTGTTTTC
 301  AGATAGCAAC AAAATATATA TAGAATTAAC TTATTTTTAA ATTTTTTGAT
 351  AATTTTATTA TATTATTTAA GAATCAATTA TTTATATTAA TATAACATAT
 401  AATTTTCACT GATTAAATAA AATTCGTTTT TAATTATATA AATTCATTAA
 451  GAGTATTGTT TTAATAACAC ATTAGCGAAC ATCAGCTAGA AATTAATAAT
 501  AAATCAATAA CCTAGCTAAA AGTCTAAAAC CTAATAAAAT ATGACAAATA
 551  AGAAAAATTA ACTAAATTTT AATATAAAAT ATAAATTTAA TATTACTAAA
 601  ATAAAATTCA TTTTTAATAT ATATAAGATT CTTAAGGGTA TTTTTTAAAT
 651  TAATAAATTA GTGACTTAGC TAAAAATAAA TAATAAATCA ATGATTTAGC
 701  TAAAACCTAA TAAAAACATG ACAAATAAGC AAATTTACTA AAATTATTGA
 751  TAATATAAAA TATGATTGAT TCTTTAATAC AAAATTAAAA TAAGAGTTTT
 801  TTTAAATCAA ACATAAGTCT GCCGTATCGG TGTTAAAAAA AAAATCATTA
 851  ATAGTGTCGT AGGAATTATG TATTTCCATT AGCGAATAAA ATTGAAGCAG
 901  AGTGTTGGAG GATAGCTCAA CGTATAGGCG AGATTATGGA GATTGATATG
 951  GGAGTTGCCG TAACGGACAC AACTGTTCCT CTGCAAAGAA ACGCTCCTAC
1001  TAGATGGACA TGTCAAGTTG ATGCATCCTG GATAAATGAA AGAAACATAT
1051  CTGGACTTGG CTTTGTGTTA ATGGATGGTG ACTTCCCAAT ACTGTTTGTA
1101  TCAACGGCCG ATATACACGC ACCAAATCAC CACTGCAAGC GGAACGTGAA
1151  GGTTTGCTAT GGGCAATGCA AGAGATACTG AAGTTTGGAC GCAGAGTGAT
1201  GGTCTTTCAA TCGACTATGA CAACTGGTT ATACTCATTC AAAAGGAGGA
1251  AGATGGCCTG CTTGGACTCG GAGCTCGACG AAATACAAGT TGTATCAAAG
1301  AATTTTCTGA AATTTCTATT GCTTATATTC CTAGATCTTT AAAATTCCGT
1351  ACGAATAGCC TAGCAAAAGG TGTCGATCAC CCGCATCACG ATCAGCTTTT
```

Figure 8a Continued

```
1401  GTAACCCTTT GCACCAGTGG CTAGCCCACA GCTAGCATGA GGGTGCAAAA
1451  GAGAATAAGT CGAAACAAGC TAGCATGAGG GTGCCAAAAA AGAGAATAAA
1501  GTCGAAAGTA AAACTGAATA TCCAATGAAC AAAATTATCA GAAATCCATA
1551  TTTATGTGGA TGTCTATATG GGACAAACAA TTTTTTTAGA TCAATCCTAA
1601  AATATATAAT TTAAAAAAAC CATTTAAACA AACCATCAAA ATTTTGAATA
1651  TTACACCAAA AAAAAATATA AAGACCAACT ATATTATATT CATGTATAAT
1701  GTGTAGTGGT AAGATTCAAA AAAATTAACT TACTTTACAG TAAGGGAAAA
1751  TTAGATTTTT TATTCCATAT TTACAGTAAA AACATAACAT TTTATAAAAC
1801  TAAACAATTG ACATAATAGT ACAAAATATG AAAAAAAAAT CAAAATACTA
1851  AGAACCTACT ATTAGTTAAA TTAAGTACAG TCAAGTCAAC TAGTATGTGA
1901  ATGAGATTTA ACTTACAAAT TCATTACGAG ACAATAGCAC ATTTAGAAGA
1951  ATAACATGTA GATTGATGTG CACACAAAAA AAAACCAACG GGTACAAATG
2001  TTAACCGCTC CACCGGTCGA ACCATAATCC AGACCGGTTT TGCTATTTAA
2051  ACCGCTCAAA TCGCAAAGTA CGTTTCGCTT ACTTCCAGCA AACCACCATT
2101  GATCTCTCCT CCAATTCACA AATCCAATTT CTCTAGGGTT TGATTTCTTC
2151  GACTTGAATT GCATTTCCAT CCGAATTTCC CCAAATTCGT CAAGCTGGAT
2201  AGGCACCGAG GGGATCGCCA CGAGAGTGCC TTACGACGAT TCCTACCGTA
2251  ACCACCGAGC TCACCTAGAG GTCCCCCTCT ACTCTCAGAT TCACCCTCCA
2301  TGTCACGTTT CGGCGAGGAT GACGAAGGTT TCAGCCGCCG TCGTCGCCGT
2351  GGAAACAGCC TAGCAATTAT CAGTTGGATG GGACAGAGGA GGTGGCGATC
2401  GACGCTGGGA AGATGACGGC CACGATCGTA TTTCACAGAG AGGCGTGGGA
2451  GAGTAGAATT TCAGCCTATG GGTTATGGCT TCGACGGAGG TTTTCCGCCG
2501  ATGAGTCGCG ACGGAGGATT TTGGCCTAAC GTGCCAGTGA ATTTTCCGCC
2551  ATCGGAAAGT CCAGATGCAG GGGGATATTC CGGCGGCAGG GGATTTCAAT
2601  CAACGGGGCC TGCTTACTCT GTGAGATTGA CTTCACCGCC GATCCAGCAG
2651  CCTCTTTCTG GTCAGAAAAG AGGTCGTCCT CTCTCGGAGC AGAGTAGCTT
2701  TACTGGAACT GGTAAGCTTG GGCTCACTCT ACTGTAATCG AGTTGTTTAG
2751  AGTTAACAGT GGTTCATTTT ATACTTGTAT GTGATAATCA GGCTATTTCC
2801  AAACTAAATT ACCTTTACTG GATCATTCGT TTTGCAGATT TACTGATAGT
```

Figure 8a Continued

```
2851 AGCAGTATGG TGAAGCTTTT TGTTGGCTCT GTACCAAGGA CAGCTACAGA
2901 AGAAGAAGTG AGTTCATCTT TTTCTTATTT TCCTAATTTC TTCTCAATAT
2951 ATATGCACTT TCTTGAGGCA ATCTAAACCA CGAAGCTCGT AGACTCTGTT
3001 CATAAGCCGT TCTTGTTTAT CATTTTGGTT TTCATAGGTC CGTCCCTTTT
3051 CGAACAACAC GGTAAATGTT CTTGAGGTTG CTTTTATCAA GGACAAGAGA
3101 ACAGGACAGC AGCAAGGTAT GTTTATCTCC ATTTTACTAG GAACAGTCGT
3151 GATTTATGCT TCTAAATTTT TCAGGTCTCC TGAAAAGGCT GATGGGAACG
3201 AACCCCAGTC TCATCATTGG CCTCCATTAG TTTTCAACAA TTTTCGGGCT
3251 TTTGCTTATG CTAGCGAGCG TCTTATCTGT GTTGCTTTGG CACAGAAGAA
3301 GGCTGCCTGT TTAGTTTACT AAGAAAGGGT TTTTGTATTG ACCTTGGTAA
3351 AATAGTTTTT GCGACTTGTG TCCATCCTAG AACCTTAGTT GTGTTTGAAC
3401 AGTGTAGCAG ACTTTATCAT GTTTTAGAGT TGGAGTTAAT GTACATAAAA
3451 TTGAACAGAT GTTTTACTGT TGCCTTTTAG TTGGCACTGG TTTAAAGAAC
3501 GTTGTTTTCT CCTTTCCTAT TGAATTCAGT ATCTCTTTAC TCTTCCTTTC
3551 GATGAATGAA AATGGTGTAT ATGGTCTTGA CTGGATGAAT GTATTTTTAC
3601 TTGGTAGTCT TACAACGTTC ATAAAATGGT TTGATTGATA AACCACCCCT
3651 GCTAGTCAAT ATTTGGCAGT TTCTTAGTGA TTATATCATG TTGGATGTTT
3701 TGTTTCTTTA GTTTCTTTAA TATCAACTTT GGATGTACCG TCTCTATTGG
3751 TTGATGATGA AATTATTTTT TACCATTTTG GATGCTTGAT GCCTTAATGA
3801 ATGGATCTTT CCTTTTTTTC TTATTGTGGA TGGCCGAGGA ACTATAATGA
3851 ATGTTCTCTT CGCTTTTTTT GAATGGCCTG GGATGTGGAC TTCTTGTATG
3901 TTCTCACTTT CATTGATGAA TGACTGTTTC GTTGAGTAGC TCTATTGTTC
3951 TGTATGGTAA CGCTAACACT GCTGATCTAC ATTATGTGGA AGAGATCATA

4001 TGTCTAATGA TATTTTTTTT CTATGTACCT TTCACCAACC AAGCTCAAAA
4051 GCTTGGTTTC AGTTTTTAGT GGTCTTATTC TATATAGAGC TTGGTTTCAG
4101 TTTTTAGTGG TCTTATTCTA TATATTGAGA TTGCTCTTGA AAAATTCCAT
4151 CAAAGTCTG TCTTTATGAT GCAAGTGTGA AGAATTACTA GATGATGAGT
4201 GATGTATTAT TTAATAATTC GGGACTTTCC AAGAAGTTAT TGTACGGTGA
```

Figure 8a Continued

```
4251  CATAAAAGCT TTTACTCATC CCGTTATCAC GGTTTGACTG TAGTAGATTT
4301  GACACATTCC TTGGTTTGAA ATGTTACATG GTGCTAAGAT ATGGAAGGCA
4351  ACGATTATTA TAATTTCTTA GAAATACGTC TTAGCTTTCA CTCGCTCTCA
4401  TTGCTTCGAT CAGCATCAGG CATGAGCCGC CTTAGTATGT ATTTAATGAA
4451  GCAAGTGTCA TTCTTCTCTA TATGCAACTA TTACCAATGA ATTGACGTTG
4501  GGTTGTGGTT ATGTCTCTCA GAACTGTAAT TCTTTTTGTG AATGTCGTCA
4551  AATGTGTGGT GTATGTTGTA TGGTGTATGG TGACGAAAAT GTGATGTATG
4601  GCTCTAGTTT TAATTATATC ATTTGTTACT TAGCAGTGAT TGAGAACTCT
4651  TAACTTGTAA TTTTATCTAA TTTTTTTTTG CAGTGATTGG ATTCTTTTTG
4701  CGTAATATAT ATTTATTTG CAAATACCGA CTGTGTTCTT TTTAAATAGT
4751  TTAAAGGCAT ATGCTTTATT TGAAGCACAT TAGTTTATTA TTCTCTCCAT
4801  CAAATCTACT ACAGTAATGT AAGTCGAGGC TGTCAGGACA TGTCTTATGA
4851  TTTTCGTACT GAAACTTATG TGCTTTCAAT GTGGTCGTGG CTTGTACATT
4901  TGTAAAGAAA CTATTTACTA GTATCTCTTG ATGTTTGATG GAGGGACAAG
4951  TGGAACCTTG AACAGAAGCT TATGTAGCAG TCTTTAATGC AGGCTGTTGT
5001  TTTGTAAAAT ATGCAACTTC TGAAGATGCG GATAGGGCCA TTAGAGCATT
5051  GCACAATCAG ATCACTCTTC CTGGGGTAAC TACCATTGAT GCCTTCTCTT
5101  ATCAAGGACA GGAAAATACA GGTTAACTCT ATCTTTACAA TTTGCTGATT
5151  CCCAGGGAAC TGGCCTTGTT CAAGTTCGAT ATGCTGATGG GGAGAGAGAA
5201  CGCATAGGTA ATCAACTTTC GCGCCATATT ATCTGAATCT GGCCTTCATT
5251  GTCTGGTATA CATAGGGTGA CCATACGCTG TACAAATTCA AATTACGAGA
5301  ATTGAGATAA TGTGGGAAAC TATATGAATC TTAAGGAAGT GGATCCTTTT
5351  TTCTGTGGTC CTTGCCTCAC TCTCAAGTAT TAACTGATTG AATTTACTTC
5401  TTCTGAAGGT GCGGTAGAGT TTAAGCTTTT TGTTGGTTCC TTAAACAAGC
5451  AAGCCACTGA AAACGAGGTT GAGGAGGTAT GTCTCATATC CTACTTTTTG
5501  ATGGAAAGTA ATTACTTATG TCTGATTTAC AAAGAGGGAA GCGTTCTAAA
5551  TTTAGATATT ACAGTATCCC CTGTCGCCTT AGCTGGTAAT TTTAGTGATT
5601  ATATGACAAT TTAGTAGTCC TCTTGGAAGG GTCAGCGGCT TGAAATTTTG
5651  TGTCAACTAT TCGAGCGCTT ACACATTTTA CTAACTGAGT GATCTCTTCT
```

Figure 8a Continued

```
5701  TTCAAATGGA CTGACTGAGT GATCTCTTCT TCCAAATGGA TGTAACTTTT
5751  TGGCTGTCAG CTTTCTTTTC TCAGTAAATA TGATGAAGAT GTGAACGGCT
5801  ACTTTGTCCT GTTGTTGCTT TAACAGCTCT TTTTGCAATT TGGTCGCGTG
5851  GAGGATGTCT ATCTCATGCG TGATGAATAT AGACAGAGTC GTGGTATGTC
5901  TGGTAACTGC CACTAGACTC TATAACTCGT TTGATGGTGT TGATATGGTC
5951  AAACTGTTTT TGACACTCAT TTAGGATGCG GGTTTGTTAA ATATTCAAGC
6001  AAAGAGACGG CCATGGCAGC TATCGATGGT CTCAATGGAA CTTATACCAT
6051  GAGAGTAAGC TGTGAAATCA CATGAGTATC TCACTTTCTC TCATTATCCC
6101  CTCTAGACCT GTTTTGTTTA CTGGCCTCTT TCCCTTCTCC AGGGTTGCAA
6151  TCAGCCATTG ATTGTTCGGT TTGCTGATCC AAAGAGGCCT AAACCGGGCG
6201  AGTCAAGGTA TTGCCTTGGA GACTATATTT TGAATTCATT ATAATGCTAA
6251  TATCAAAAAA ATTGTGTCTA CTGTCATTGT TTGTTCTATT GAGTTACATT
6301  TATGAGAATC TTTTGGGGCA TGGGTGGAGG AGAGCTGCGA ACCTTATTCC
6351  TTCTCCAGTT ATTACTTGAA TGCGATGAAT TTCTTTCTAT ATATCCTTAA
6401  CTAGTTTCTG TTTCCAGGGA AGTGGCACAT CCTGTTGGAC TTTGTTCAGG
6451  GCCTCGTTTT CAAGCTTCAG GACCAAGGTG ACTGGGGTGA AAGGAGATCG
6501  TTGTTTTTGT CATCAATTAA TTATATATTT TGACTAAACG TGGTCTCCTT
6551  ATCTTCATTT GTTAGGCCTA CATCTAACCT TGGTGACCTT AGTGTGGATG
6601  TGAGCCACAC AAATCCTTGG CGTCCTATGA ATTCACCAAA CATGGGGCCA
6651  CCTGGTAACA CTGGGATCCG TGGTACCGGA AGTGACTTGG CTCCTAGGCC
6701  AGGTCAAGCC ACATTACCTT CAAATCAGGT AAGAACAGCT TGATGATCAT
6751  GTATATTATC TTATATGTAC ACACCCAATC ACACATAAAG TAATCGGGCA
6801  TAAGGTTTTA CATGTATTGT GTGAGTAGGA CGAACATAAT TTATATGCTG
6851  CACATATATG AGCGTATGGA CTCTTGAAAA GAAGCATGAA GTTCCGACCT
6901  TCCAGCTTTT CATATGATGC AGCAAACTTG ATGTGTTTTG CATTGAAATG
6951  ATATGGCTTT GATTTGCATT TTGTCAGTTT CTAAGGAGTT TTTTCTTCA
7001  ATAATTTCTA CTTCTGATGT TAGCTTTATT TGTGGCATTC TATAATGTTA
7051  GGGAGGTCCA TTGGGTGGTT ATGTTGTTCC TGCCATTAAC CCTCTACCAG
7101  TCTCATCCTC TGCCACATCG CAACAGGTAC TTCAGCTGAA TTTTTCCAAT
```

Figure 8a Continued

```
7151  AAAGAAAATC TGAAAATGTT GTGTTGATCA GTTAATTTCA ACTGTTTCTA
7201  TTCCATAGCA AAACCGGGGA GCTGGCCAGC ATATGTCACC ATTACAAAAA
7251  CCTCTTCACA GTCCACAGGA TGTGCCCCTT CGACCACAAA CTAATTTCCC
7301  TGGGGCCCAA GCATCCTTGC AGAATCCTTA TGGTTATAGC AGCCAGTTGC
7351  CTACTTCTCA GCTGCGGCCA CAACAAAACG TCACTCCTGC AACAGCTCCT
7401  CAAGCTCCTT TGAACATCAA CCTACGGCCA ACACCTGTAT CTTCTGCAAC
7451  TGATCAATTG CGCCCTCGTG CTCAGCAGCC ACCGCCACAA AAGATGCAAC
7501  ATCCTCCTTC TGAGCTAGTT CAGCTCTTGT CACAACAGAC TCAGACTCTA
7551  CAAGCAACCT TCCAATCATC TCAGCAAGCA TTTTCTCAAC TGCAGGAGCA
7601  GGTGCAGTCC ATGCAGCAAC CAAACCAAAA ATTACCAGGC TCACAGACTG
7651  GCCATGGTAA ACAGCAGGTA CAAACATAGT TCCCTGTTGC ATCTGTCCAG
7701  TCCAGTTCCT CAGCTGTTTT TGTTGTTTTA ACTTACAATT ATTTCCTGAT
7751  GTCTAAGTAT TCAATCCTTC ATATATTTTA GTAGTCCCTC TTTTTTATTA
7801  TGTTTTTCTC GGTTGCTTCT CTATCAGTGG GCTGGATCTG CAATTCCGAC
7851  AGTTGTTAGC ACCACTGCTT CTACACCAGT TAGCTATATG CAAACAGCTG
7901  CACCTGCAGC AACTCAGAGT GTTGTTTCTC GCAAATGTAA CTGGACCGAG
7951  CATACCTCGC CTGATGGATT TAAGTATTAT TACAACGGTC AAACCGGTGA
8001  AAGCAAGGTG AGAAACGTGG TTCCTCTTTA GTTATGTTCT CTTGTGAGTT
8051  TCAGGAGGAT TCCTTGTATT TGCTGTGCTA TTTATTATCC TTGAACATGT
8101  ATATGTATAG ATTTCATATT TGAAGTTCAT CAATACGTGT CGTAATATAA
8151  TTGACTTTTG CAGTGGGAAA AACCTGAGGA AATGGTATTG TTCGAACGTC
8201  AGCAACAGCA GCCAACTATA AATCAGCCCC AGACCCAATC ACAGCAGGCT
8251  CTTTATTCCC AGCCGATGCA GCAACAACCA CAACAGGTTC ACCAGCAATA
8301  TCAGGGCCAA TATGTACAGC AGCCTATTTA TTCTTCAGTG GTTGGTTCTG
8351  TTTTCTTGCT GCTTACATCC ATATAGTTTT CTCACATGGT CTCTAACTTG
8401  AATATGTATT CTTTTCCATT TGGAGTTGCA GTATCCAACT CCAGGGGTCA
8451  GCCAGAATGC TCAGGTGTAT ATTTAGTTAA ATTATTTGCT TATCTTTCAT
8501  TTCAGAATTT GATCATTGAG TTACCAATCT AGTGGGTATA AGGAGACGGG
8551  CCACTTTATG CAATAAACCA TGGTTTTACA AGCGTTTTGA ATATACAGAT
```

Figure 8a Continued

```
8601  ACAAACATCT AAATTTGATC ATTTCAAAAT TTGATCATCG AGTTCCCTTT
8651  TCAATGCAGT ATCCGCCGCC ATTGGGAGTT AGTCAAAATA GCCAGGTACA
8701  TATTTGAACC TTATTTCACG TGGGACTAAT TGAAATTCGA TTTTGATATG
8751  CATTTCATAA ATGTGAAGAT TTGATGAGTG GTCGTTTTGG TAGCGTTTTA
8801  GAAAACGATA TGCATATATT CTCTAGTTGA ATATTTCTTT TTTCTGGAAC
8851  ATGCAGTTTC CTATGTCAGG CACCGGTCAA AATGCTCAGG TACATATTAT
8901  ATCATGCATC ATATCTTCTG ATTAACTTCA AATTTAATCA GAAACATAC
8951  GTGAGATTCC AGTAGAAACA AAATCGATAT GACTGTATTG GTTGGAAATG
9001  GTTAAGGCAG AGCTCATGTT CTAATGTGTT AAAATTTTCT AGGAATTT
```

Figure 8b

```
  1  MGYGFDGGFP PMSRDGGFWP NVPVNFPPSE SPDAGGYSGG RGFQSTGPAY
 51  SVRLTSPPIQ QPLSGQKRGR PLSEQSSFTG TGLLIVAVMV KLFVGSVPRT
101  ATEEEVRPFS NNTVNVLEVA FIKDKRTGQQ QGCCFVKYAT SEDADRAIRA
151  LHNQITLPGG TGLVQVRYAD GERERIGAVE FKLFVGSLNK QATENEVEEL
201  FLQFGRVEDV YLMRDEYRQS RGCGFVKYSS KETAMAAIDG LNGTYTMRGC
251  NQPLIVRFAD PKRPKPGESK EVAHPVGLCS GPRFQASGPK PTSNLGDLSV
301  DVSHTNPWRP MNSPNMGPPG NTGIRGTGSD LAPRPGQATL PSNQGGPLGG
351  YVVPAINPLP VSSSATSQQQ NRGAGQHMSP LQKPLHSPQD VPLRPQTNFP
401  GAQASLQNPY GYSSQLPTSQ LRPQQNVTPA TAPQAPLNIN LRPTPVSSAT
451  DQLRPRAQQP PPQKMQHPPS ELVQLLSQQT QTLQATFQSS QQAFSQLQEQ
501  VQSMQQPNQK LPGSQTGHGK QQWAGSAIPT VVSTTASTPV SYMQTAAPAA
551  TQSVVSRKCN WTEHTSPDGF KYYYNGQTGE SKWEKPEEMV LFERQQQQPT
601  INQPQTQSQQ ALYSQPMQQQ PQQVHQQYQG QYVQQPIYSS VYPTPGVSQN
651  AQYPPPLGVS QNSQFPMSGT GQNAQ
```

Figure 9

```
    MGFAYDDGFRPMGPNGGVGGEGTRSIVGARYNYPAKYPPSESPDRRRFIG  61
    ||:::|:||.||:..:||.            : | |..:|||||||    : |
    MGYGFDGGFPPMSRDGGF..........WPNVPVNFPPSESPDAGGYSG  39

62 ....KAMESDYSVRPTTPPVQQPLSGQKRGYPISDHGSFTGTDVSDRSST 107
        .. :...||||  |.||:|||||||||||  |:|:::|||||::
 40 GRGFQSTGPAYSVRLTSPPIQQPLSGQKRGRPLSEQSSFTGTGLLIVAVM  89

108 VKLFVGSVPRTATEEEIRPYFEQHGNVLEVALIKDKRTGQQQGCCFVKYA 157
    |||||||||||||||||:||:  :.  |||||||:|||||||||||||||
 90 VKLFVGSVPRTATEEEVRPFSNNTVNVLEVAFIKDKRTGQQQGCCFVKYA 139

158 TSKDADRAIRALHNQITLPGGTGPVQVRYADGERERIGTLEFKLFVGSLN 207
    ||.+|||||||||||||||||| ||||||||||||||.:|||||||||i
140 TSEDADRAIRALHNQITLPGGTGLVQVRYADGERERIGAVEFKLFVGSLN 189

208 KQATEKEVEEIFLQFGHVEDVYLMRDEYRQSRGCGFVKYSSKETAMAAID 257
    |||||.||||:|||||:|||||||||||||||||||||||||||||||||
190 KQATENEVEELFLQFGRVEDVYLMRDEYRQSRGCGFVKYSSKETAMAAID 239

258 GLNGTYTMRGCNQPLIVRFAEPKRPKPGESRDMAPPVGLGSGPRFQASGP 307
    ||||||||||||||||||||:|||||||||:::|.||||.|||||||||
240 GLNGTYTMRGCNQPLIVRFADPKRPKPGESKEVAHPVGLCSGPRFQASGP 289

308 RPTSNFGDSSGDVSHTNPWRPATSRNVGPPSNTGIRGAGSDFSPKPGQAT 357
    :||||:|| |.|||||||||| .|.|:|||:|||||.|||:.|:|||||
290 KPTSNLGDLSVDVSHTNPWRPMNSPNMGPPGNTGIRGTGSDLAPRPGQAT 339

358 LPSNQGGPLGGYGVPPLNPLPVPGVSSSATLQQENRAAGQHITPLKKPLH 407
    ||||||||||||.||::||||     ||||||  ||:||:||||..||||
340 LPSNQGGPLGGYVVPAINPLP...VSSSATSQQQNRGAGQHMSPLQKPLH 386

408 SPQGLPLPLRPETNFPGGQAPLQNPYAYSSQLPTSQLPPQQNISRATAPQ 457
    |||:  :|||||:||||:||.|||||:|||||||||||||.||||:...|||||
387 SPQD..VPLRPQTNFPGAQASLQNPYGYSSQLPTSQLRPQQNVTPATAPQ 434

458 TPLNINLRPTTVSSATVQFPPRSQQQPLQKMQHPPSELAQLLSQQTQSLQ 507
    .||||||||.|||||  |:.||.||.| ||||||||||.||||||||.||
435 APLNINLRPTPVSSATDQLRPRAQQPPPQKMQHPPSELVQLLSQQTQTLQ 484

508 ATFQSSQQAISQLQQQVQSMQQPNQNLPLSQNGRAGKQQWAGSAIPRVAS 557
    ||||||||||:||||:|||||||||.|| ||.|: |||||||||||| |.|
485 ATFQSSQQAFSQLQEQVQSMQQPNQKLPGSQTGH.GKQQWAGSAIPTVS 533

558 TTGSTPVSYVQTAAPAVSQSVGSVKCTWTEHTSPDGFKYYYNGLTGESKW 607
    ||:|||||||:||||||..||| .| ||.|||.|||||||||||||||||
534 TTASTPVSYMQTAAPAATQSVVSRKCNWTEHTSPDGFKYYYNGQTGESKW 583

608 EKPEEMIVFEREQQKQQQHQEKPTIQQSQTQ......LQPLQQQPQQVQQ 651
    ||||||::|||:||          |||.|.|||     ||:|||||||:|
584 EKPEEMVLFERQQQ.......QPTINQPQTQSQQALYSQPMQQQPQQVHQ 626

652 QYQGQQLQQPFYSSLYPTPGASHNTQY.PSLPVGQNSQFPMSGIGQNAQ 699
    |||||  :|||:|||:|||||.|:|.||  |.|.|||||||||||||
627 QYQGQYVQQPIYSSVYPTPGVSQNAQYPPPLGVSQNSQFPMSGTGQNAQ 675
```

GENETIC CONTROL OF FLOWERING

This invention relates to the genetic control of flowering in plants and the cloning and expression of genes involved therein. More particularly, the invention relates to the cloning and expression of the FCA gene of *Arabidopsis thaliana*, and homologues from other species, and manipulation and use of these genes in plants.

Efficient flowering in plants is important, particularly when the intended product is the flower or the seed produced therefrom. One aspect of this is the timing of flowering: advancing or retarding the onset of flowering can be useful to farmers and seed producers. An understanding of the genetic mechanisms which influence flowering provides a means for altering the flowering characteristics of the target plant. Species for which flowering is important to crop production are numerous, essentially all crops which are grown from seed, with important examples being the cereals, rice and maize, probably the most agronomically important in warmer climatic zones, and wheat, barley, oats and rye in more temperate climates. Important seed products are oil seed rape, sugar beet, maize, sunflower, soybean and sorghum. Many crops which are harvested for their roots are, of course, grown annually from seed and the production of seed of any kind is very dependent upon the ability of the plant to flower, to be pollinated and to set seed. In horticulture, control of the timing of flowering is important. Horticultural plants whose flowering may be controlled include lettuce, endive and vegetable brassicas including cabbage, broccoli and cauliflower, and carnations and geraniums.

*Arabidopsis thaliana* is a facultative long day plant, flowering early under long days and late under short days. Because it has a small, well-characterized genome, is relatively easily transformed and regenerated and has a rapid growing cycle, Arabidopsis is an ideal model plant in which to study flowering and its control.

One of the genes required for rapid floral induction is the FCA gene (Koornneef et al 1991). Plants carrying mutations of this gene flower much later than wild-type under long photoperiods and short photoperiods. There is a considerable range in flowering time within different mutant fca alleles. The most extreme (fca-1) flowers under long photoperiods with up to 40 leaves whereas fca-3, fca-4 flower with ~20 rosette leaves compared to 9 for wild-type Landsberg erecta). The late flowering of all the fca mutants can be overcome to early flowering in both long and short photoperiods if imbibed seeds, or plants of different developmental ages, are given 3–8 weeks at 4° C.—a vernalization treatment (Chandler and Dean 1994).

We have cloned and sequenced the FCA gene of *Arabidopsis thaliana*, a homologue from Brassica and mutant sequences.

According to a first aspect of the present invention there is provided a nucleic acid molecule comprising a nucleotide sequence encoding a polypeptide with FCA function. Those skilled in the art will appreciate that "FCA function" refers to the ability to influence the timing of flowering phenotypically like the FCA gene of *Arabidopsis thaliana*, especially the ability to complement an fca mutation in *Arabidopsis thaliana*.

Nucleic acid according to the invention may encode a polypeptide comprising the amino acid sequence shown in FIG. 2 SEQ ID NO:3, or an allele, variant, derivative or mutant thereof. Particular variants include those wherein the amino acid residues up-stream of the third methionine and/or up-stream of the second methionine in the amino acid sequence of FIG. 2 SEQ ID NO:3 are not included. Variants, mutants and derivatives of nucleic acid encoding such shorter polypeptide are of course provided by various embodiments of the present invention.

Nucleic acid according to the present invention may have the sequence of an FCA gene of *Arabidopsis thaliana*, or be a mutant, variant (or derivative) or allele of the sequence provided. Preferred mutants, variants and alleles are those which encode a protein which retains a functional characteristic of the protein encoded by the wild-type gene, especially the ability to promote flowering as discussed herein. Promotion of flowering may advance, hasten or quicken flowering. Other preferred mutants, variants and alleles encode a protein which delays flowering compared to wild-type or a gene with the sequence provided. Changes to a sequence, to produce a mutant or variant, may be by one or more of insertion, deletion or substitution of one or more nucleotides in the nucleic acid, leading to the insertion, deletion or substitution of one or more amino acids. Of course, changes to the nucleic acid which make no difference to the encoded amino acid sequence are included. Particular variants, mutants, alleles and variants are discussed further below.

A preferred nucleic acid sequence covering the region encoding the FCA gene is shown in FIG. 1 SEQ ID NO:1 and the predicted amino acid sequence encoding the FCA ORF is shown in FIG. 2 SEQ ID NO:30. Nucleic acid may be subject to alteration by way of subsitution of nucleotides and/or a combination of addition, insertion and/or substitution of one or more nucleotides with or without altering the encoded amino acids sequence (by virtue of the degeneracy of the genetic code).

Nucleic acid according to the present invention may comprise an intron, such as an intron shown in FIG. 1 SEQ ID NO:1, for instance intron 3 (as in various embodiments e.g. as illustrated herein), whether or not the encoded amino acid sequence is altered. For example, the variant FCA $\alpha_B$, whose nucleic acid sequence is shown in FIG. 3 SEQ ID NO:2, comprises intron 3 of the sequence of FIG. 1 SEQ ID NO:1, such that translation of the sequence results in a different amino acid sequence from that of FIG. 2 SEQ ID NO:3 (intron 3 of FIG. 1 SEQ ID NO:1 contains a stop codon at 3026–3028 that is potentially used in transcripts).

The present invention also provides a vector which comprises nucleic acid with any one of the provided sequences, preferably a vector from which polypeptide encoded by the nucleic acid sequence can be expressed. The vector is preferably suitable for transformation into a plant cell. The invention further encompasses a host cell transformed with such a vector, especially a plant cell. Thus, a host cell, such as a plant cell, comprising nucleic acid according to the present invention is provided. Within the cell, the nucleic acid may be incorporated within the chromosome. There may be more than one heterologous nucleotide sequence per haploid genome. This, for example, enables increased expression of the gene product compared with endogenous levels, as discussed below.

A vector comprising nucleic acid according to the present invention need not include a promoter, particularly if the vector is to be used to introduce the nucleic acid into cells for recombination into the genome.

Nucleic acid molecules and vectors according to the present invention may be provided isolated and/or purified from their natural environment, in substantially pure or homogeneous form, or free or substantially free of nucleic acid or genes of the species of interest or origin other than the sequence encoding a polypeptide able to influence flowering, eg in *Arabidopsis thaliana* nucleic acid other than the FCA sequence. Nucleic acid according to the present invention may comprise cDNA, RNA, genomic DNA and may be wholly or partially synthetic. The term "isolate" may encompass all these possibilities.

The present invention also encompasses the expression product of any of the nucleic acid sequences disclosed and methods of making the expression product by expression from encoding nucleic acid therefore under suitable conditions in suitable host cells, e.g. *E. coli* (see Example 7). Those skilled in the art are well able to construct vectors and design protocols for expression and recovery of products of recombinant gene expression. Suitable vectors can be chosen or constructed, containing one or more appropriate regulatory sequences, including promoter sequences, terminator fragments, polyadenylation sequences, enhancer sequences, marker genes and other sequences as appropriate. For further details see, for example, Molecular Cloning: a Laboratory Manual: 2nd edition, Sambrook et al, 1989, Cold Spring Harbor Laboratory Press. Transformation procedures depend on the host used, but are well known. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., John Wiley & Sons, 1992. The disclosures of Sambrook et al. and Ausubel et al. are incorporated herein by reference.

Purified FCA protein, or a fragment, mutant or variant thereof, e.g. produced recombinantly by expression from encoding nucleic acid therefor, may be used to raise antibodies employing techniques which are standard in the art, as exemplified in Example 7. Antibodies and polypeptides comprising antigen-binding fragments of antibodies may be used in identifying homologues from other species as discussed further below.

Methods of producing antibodies include immunising a mammal (eg human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80–82). Antibodies may be polyclonal or monoclonal.

As an alternative or supplement to immunising a mammal, antibodies with appropriate binding specificity may be obtained from a recombinantly produced library of expressed immunoglobulin variable domains, eg using lambda bacteriophage or filamentous bacteriophage which display functional immunoglobulin binding domains on their surfaces; for instance see WO92/01047.

Antibodies raised to a polypeptide or peptide can be used in the identification and/or isolation of homologous polypeptides, and then the encoding genes. Thus, the present invention provides a method of identifying or isolating a polypeptide with FCA function (in accordance with embodiments disclosed herein), comprising screening candidate polypeptides with a polypeptide comprising the antigen-binding domain of an antibody (for example whole antibody or a fragment thereof) which is able to bind an FCA polypeptide or fragment, variant or variant thereof or preferably has binding specificity for such a polypeptide, such as having the amino acid sequence shown in FIG. 2 SEQ ID NO:3 or FIG. 8b SEQ ID NO:5. Specific binding members such as antibodies and polypeptides comprising antigen binding domains of antibodies that bind and are preferably specific for a FCA polypeptide or mutant, variant or derivative thereof represent further aspects of the present invention, as do their use and methods which employ them.

Candidate polypeptides for screening may for instance be the products of an expression library created using nucleic acid derived from an plant of interest, or may be the product of a purification process from a natural source.

A polypeptide found to bind the antibody may be isolated and then may be subject to amino acid sequencing. Any suitable technique may be used to sequence the polypeptide either wholly or partially (for instance a fragment of the polypeptide may be sequenced). Amino acid sequence information may be used in obtaining nucleic acid encoding the polypeptide, for instance by designing one or more oligonucleotides (e.g. a degenerate pool of oligonucleotides) for use as probes or primers in hybridisation to candidate nucleic acid, or by searching computer sequence databases, as discussed further below.

The present invention further encompasses a plant comprising a plant cell comprising nucleic acid according to the present invention e.g. as a result of introduction of the nucleic acid into the cell or an ancestor thereof, and selfed or hybrid progeny and any descendent of such a plant, also any part or propagule of such a plant, progeny or descendant, including seed.

The FCA gene encodes a large protein (796 amino acids shown in FIG. 2 SEQ ID NO:3) with homology to a class of proteins identified as RNA-binding proteins (Burd and Dreyfuss 1994). These proteins contain 80 amino acid, RNA recognition motifs (RRMs) and have a modular structure—they can contain several RNA binding domains and auxiliary domains rich in amino acids such as glycine, glutamine and proline. The RRM proteins can be divided into subfamilies based on homology within and around the RRM domains. The FCA protein is most homologous to a subfamily of RNA-binding proteins (cluster 1028.16; identified using the BEAUTY database search, Worley et al., 1995) exemplified by the *Drosophila elav* gene (Robinow et al., 1988). Other members of this family include the Drosophila sexlethal protein; the human nervous system proteins HuD, HuC, Hel-N1, and Hel-N2; and the Xenopus proteins elrA, elrB, elrC, elrD and etr-1. FCA has two RNA-binding domains while most of the members of *elav* gene family have three RNA-binding domains. The first two RNA-binding domains of *elav* family (and the spacing between the domains) is similar to the RNA-binding domains in the FCA protein. In common with the FCA protein the *elav* has a region with high glutamine content. There is also a 20 amino acid region near the C terminus of the FCA protein which shows strong homology to ORFs from two genes of unknown function from yeast and *C. elegans*.

The FCA transcript is alternatively spliced. Five forms of the transcript are generated in cells. One, herein called FCA transcript β is ~2 kb and represents premature termination and polyadenylation within intron 3. FCA $\alpha_A$ and $\alpha_B$ has 19 of 20 introns spliced out but intron 3 (2 kb) remaining. FCA $\alpha_A$ is the same as $\alpha_B$ except at intron 13 where different 5' and 3' exon/intron junctions are used. FCA $\alpha_A$ uses the 5' exon/intron junction at 7055 bp (genomic sequence FIG. 1) and 3' exon/intron junction at 7377 bp. FCA $\alpha_B$ uses the 5' exon/intron junction at 7130 bp (genomic sequence FIG. 1) and 3' exon/intron junction at 7295 bp. FCA transcripts $\gamma_A$ and $\gamma_B$ both have intron 3 removed and $\gamma_A$ and $\gamma_B$ use the same junctions around intron 13 as $\alpha_A$ and $\alpha_B$, respectively. Only $\gamma_B$ encodes both RNA-binding domains and the conserved C-terminal domain (FIG. 10).

RNA-binding proteins have been shown to be involved in several facets of post-transcriptional regulation. The RNP motif forms a β sheet RNA binding surface engaging the RNA as an open platform for interaction with either other RNA molecules or other proteins. One of the most well characterized genes encoding an RNP motif-containing protein is the Drosophila SEX-LETHAL gene (Bell et al 1988). The SEX-LETHAL protein is involved in altering the splicing of its own and other transcripts within the pathway that determines sex in Drosophila. Only the alternatively spliced product gives an active protein. Thus this gene product is responsible for determining and maintaining the female state. Other RNA-binding proteins have been shown to function by localizing specific transcripts in the nucleus or preventing translation of specific transcripts. Six independently isolated fca mutants have been described, and we have identified the sequence changes causing a reduction in FCA activity in three cases. The fca-1 mutation converted a C nucleotide at position 6861 (FIG. 1 SEQ ID NO:1) into a T. Thus a glutamine codon (CAA) is changed into a stop codon (TAA). The fca-3 mutation converted a G nucleotide at position 5271 into an A. The effect of this mutation is to alter the 3' splice junction of intron 7 such that a new 3' splice junction is used 28 nucleotides into exon 8. The fca-4 mutation is the result of a rearrangement (an inversion taking the 3' end of the gene 250 kb away) with the break-point at position 4570 (within intron 4).

A further aspect of the present invention provides a method of identifying and cloning FCA homologues from plant species other than *Arabidopsis thaliana* which method employs a nucleotide sequence derived from that shown in FIG. 1 SEQ ID NO:1. Nucleic acid libraries may be screened using techniques well known to those skilled in the art and homologous sequences thereby identified then tested. The provision of sequence information for the FCA gene of *Arabidopsis thaliana* enables the obtention of homologous sequences from Arabidopsis and other plant species. In Southern hybridization experiments a probe containing the FCA gene of *Arabidopsis thaliana* hybridises to DNA extracted from *Brassica rapa, Brassica napus* and *Brassica oleraceae*. In contrast to most Arabidopsis genes, which are normally present on the *B. napus* genome in 6 copies, the FCA gene is present twice, on only one pair of chromosomes. An FCA homologue from *Brassica napus* has been isolated and sequenced and shows 86.1% average nucleotide sequence homology within the exons, 65.8% within introns and 78% identity at the amino acid level (87% similarity). This Brassica gene fully complements a mutation in the Arabidopsis FCA gene and can thus be considered as a fully functional homologue. Homologues have also been detected by Southern blot analysis from Antirrhinum, tobacco, sugarbeet, tomato, pea, wheat, maize, rice, rye, Lolium and oats.

The Brassica FCA homologue whose nucleotide sequence is given in FIG. 8*a* SEQ ID NO:4, including the coding sequence, and whose amino acid sequence encoded by the sequence of FIG. 8*a* is shown in FIG. 8*b* SEQ ID NO:5, represents and provides further aspects of the present invention in accordance with those disclosed for the Arabidopsis FCA gene. For example, mutants, alleles and variants are included, e.g. having at least 80% identity with the sequence of FIG. 8*b* SEQ ID NO:5, though high levels of amino acid identity may be limited to functionally significant domains or regions as discussed.

The present invention also extends to nucleic acid encoding an FCA homologue obtained using a nucleotide sequence derived from that shown in FIG. 1 SEQ ID NO:1, or the amino acid sequence shown in FIG. 2 SEQ ID NO:3. Preferably, the nucleotide sequence and/or amino acid sequence shares homology with the sequence encoded by the nucleotide sequence of FIG. 1 SEQ ID NO:1, preferably at least about 50%, or at least about 60%, or at least about 70%, or at least about 75%, or at least about 78%, or at least about 80% homology, most preferably at least about 90% homology, from species other than *Arabidopsis thaliana* and the encoded polypeptide shares a phenotype with the *Arabidopsis thaliana* FCA gene, preferably the ability to influence timing of flowering. These may promote or delay flowering compared with *Arabidopsis thaliana* FCA and mutants, variants or alleles may promote or delay flowering compared with wild-type. "Homology" may be used to refer to identity.

In certain embodiments, an allele, variant, derivative, mutant or homologue of the specific sequence may show little overall homology, say about 20%, or about 25%, or about 30%, or about 35%, or about 40% or about 45%, with the specific sequence. However, in functionally significant domains or regions the amino acid homology may be much higher. Comparison of the amino acid sequences of the FCA polypeptides of the *Arabidopsis thaliana* and *Brassic napus* genes, as in FIG. 9, reveals domains and regions with functional significance, i.e. a role in influencing a flowering characteristic of a plant, such as timing of flowering. Deletion mutagenesis, for example, may be used to test the function of a region of the polypeptide and its role in or necessity for influence of flowering timing.

The nucleotide sequence information provided herein, or any part thereof, may be used in a data-base search to find homologous sequences, expression products of which can be tested for ability to influence a flowering characteristic. These may have FCA function or the ability to complement a mutant phenotype, which phenotype is delayed flowering, where the delay can be reversed by a vernalization treatment.

Vernalization is well known in the art and appropriate conditions are at the disposal of skilled artisans. Plants may be vernalized at the seed stage, immediately after sowing. It may be carried out for 8 weeks, in an 8 hour photoperiod (e.g may be fluorescent light, PAR 9.5 mmol $m^{-2}s^{-1}$, R/FR ratio 3.9) at a temperature of 5° C.+/−1° C.

In public sequence databases we recently identified several Arabidopsis cDNA clone sequences that were obtained in random sequencing programmes and share homology with FCA within both the RRM domains and in the C-terminal regions. BLAST and FASTA searches of databases have identified 23 Arabidopsis expressed sequence tags (ESTs) identified. These clones have been obtained and used in low stringency hybridization experiments with different regions of the FCA gene (central and 3'). Eight clones show good homology to the 3' part of the FCA gene, two clones show good homology to the central part and one clone shows good homology to both (42 A 4—another RNA-binding protein). Similarly, among randomly sequenced rice cDNAs we have identified 10 rice ESTs. These hybridise to FCA genomic and cDNA clones under low stringency conditions. Five clones show good hybridization to FCA, particularly C1480.

By sequencing homologues, studying their expression patterns and examining the effect of altering their expression, genes carrying out a similar function to FCA in regulating flowering time are obtainable. Of course, mutants, variants and alleles of these sequences are included within the scope of the present invention in the same terms as discussed above for the *Arabidopsis thaliana* FCA gene.

The high level of homology between the FCA genes of *Arabidopsis thaliana* and *Brassica napus*, as disclosed herein, may also be exploited in the identification of further homologues, for example using oligonucleotides (e.g. a degenerate pool) designed on the basis of sequence conservation.

According to a further aspect, the present invention provides a method of identifying or a method of cloning a FCA homologue from a species other than *Arabidopsis thaliana*, the method employing a nucleotide sequence derived from that shown in FIG. 1 SEQ ID NO:1 or that shown in FIG. 8a SEQ ID NO:4. For instance, such a method may employ an oligonucleotide or oligonucleotides which comprises or comprise a sequence or sequences that are conserved between the sequences of FIGS. 1 and 8a to search for homologues. Thus, a method of obtaining nucleic acid whose expression is able to influence a flowering characteristic of a plant is provided, comprising hybridisation of an oligonucleotide or a nucleic acid molecule comprising such an oligonucleotide to target/candidate nucleic acid. Target or candidate nucleic acid may, for example, comprise a genomic or cDNA library obtainable from an organism known to contain or suspected of containing such nucleic acid. Successful hybridisation may be identified and target/candidate nucleic acid isolated for further investigation and/or use.

Hybridisation may involve probing nucleic acid and identifying positive hybridisation under suitably stringent conditions (in accordance with known techniques) and/or use of oligonucleotides as primers in a method of nucleic acid amplification, such as PCR. For probing, preferred conditions are those which are stringent enough for there to be a simple pattern with a small number of hybridisations identified as positive which can be investigated further. It is well known in the art to increase stringency of hybridisation gradually until only a few positive clones remain.

As an alternative to probing, though still employing nucleic acid hybridisation, oligonucleotides designed to amplify DNA sequences may be used in PCR reactions or other methods involving amplification of nucleic acid, using routine procedures. See for instance "PCR protocols; A Guide to Methods and Applications", Eds. Innis et al, 1990, Academic Press, New York.

Preferred amino acid sequences suitable for use in the design of probes or PCR primers are sequences conserved (completely, substantially or partly) between at least two FCA polypeptides able to influence a flowering characteristic, such as timing of flowering, e.g. with the amino acid sequences of FIGS. 2 and 8b herein.

On the basis of amino acid sequence information oligonucleotide probes or primers may be designed, taking into account the degeneracy of the genetic code, and, where appropriate, codon usage of the organism from the candidate nucleic acid is derived.

Preferably an oligonucleotide in accordance with the invention, e.g. for use in nucleic acid amplification, has about 10 or fewer codons (e.g. 6, 7 or 8), i.e. is about 30 or fewer nucleotides in length (e.g. 18, 21 or 24).

Assessment of whether or not such a PCR product corresponds to resistance genes may be conducted in various ways. A PCR band from such a reaction might contain a complex mix of products. Individual products may be cloned and each one individually screened. It may be analysed by transformation to assess function on introduction into a plant of interest.

Generally, nucleic acid according to the invention may comprise a nucleotide sequence encoding a polypeptide able to complement a mutant phenotype which is delayed in flowering, where that delay can be corrected by a vernalization treatment. Also the present invention provides nucleic acid comprising a nucleotide sequence which is a mutant or variant of a wild-type gene encoding a polypeptide with ability to influence the timing of flowering, the mutant or variant phenotype being delayed in flowering with the timing of flowering being corrected by vernalization. These are distinguished from the CO gene reported by Putterill et al 1995, Putterill et al 1993 and the LD gene reported by Lee et al 1994. LD shows similar characteristics to the FCA gene in that a mutation in the gene confers late flowering that is corrected by a vernalization treatment, but LD requires a second gene product to influence flowering time in the *Arabidopsis thaliana* Landsberg erecta ecotype (Lee et al 1994, Koornneef et al 1994). Thus in many plant species manipulation of the LD gene alone may not influence flowering time. The action of FCA is opposite in action to that of phytochromeB, in that mutations in PHYB (hy3) confer early flowering and introduction of an intact PHYB gene into hy3 mutants restores normal flowering time (Wester] et al 1994). LD and CO are excluded from the ambit of the present invention. FCA and mutants, variants and alleles thereof may not complement an LD mutation. LD and mutants, variants and alleles thereof may not complement an FCA mutation.

The FCA amino acid sequence is totally different from those of CO and LD.

The action of FCA can also be distinguished from ectopic expression of meristem identity or MADS box genes that alter flowering time (Weigel and Nilsson 1995, Chung et al 1994, Mandel and Yanofsky 1995, Mizukama and Ma 1992). Apart from an early flowering phenotype, ectopic or overexpression of meristem identity or MADS box genes produces many additional perturbations to both the vegetative and floral phenotype of the plant (eg. short stature, reduced apical dominance, sterile flowers).

Also according to the invention there is provided a plant cell having incorporated into its genome a sequence of nucleotides where different introns have been removed. A further aspect of the present invention provides a method of making such a plant cell involving introduction of a vector comprising the sequence of nucleotides into a plant cell and causing or allowing recombination between the vector and the plant cell genome to introduce the sequence of nucleotides into the genome.

Plants which comprise a plant cell according to the invention are also provided, along with any part or propagule thereof, seed, selfed or hybrid progeny and descendants and any part or propagate thereof.

The invention further provides a method of influencing the flowering characteristics of a plant comprising expression of a heterologous FCA gene sequence (or mutant, allele, variant or homologue thereof, as discussed) within cells of the plant. The term "heterologous" indicates that the gene/sequence of nucleotides in question have been introduced into said cells of the plant or an ancestor thereof, using genetic engineering, ie by human intervention. The gene may be on an extra-genomic vector or incorporated, preferably stably, into the genome. The heterologous gene may replace an endogenous equivalent gene, ie one which normally performs the same or a similar function in control of flowering, or the inserted sequence may be additional to the endogenous gene. An advantage of introduction of a heterologous gene is the ability to place expression of the gene under the control of a promoter of choice, in order to be able to influence gene expression, and therefore flowering, according to preference. Furthermore, mutants and variants of the wild-type gene, eg with higher or lower activity than wild-type, may be used in place of the endogenous gene.

The principal flowering characteristic which may be altered using the present invention is the timing of flowering. Under-expression of the gene product of the FCA gene leads to delayed flowering (as indicated by the fca mutant phenotype and Example 3, antisense experiments) that can be overcome to early flowering by a vernalization treatment; over-expression may lead to earlier flowering (Examples 2, 4 and 5). This degree of control is useful to ensure synchronous flowering of male and female parent lines in hybrid production, for example. Another use is to advance or retard the flowering in accordance with the dictates of the climate so as to extend or reduce the growing season. This may involve use of anti-sense or sense regulation.

The nucleic acid according to the invention, such as a FCA gene or homologue, may be placed under the control of an externally inducible gene promoter thus placing the timing of flowering under the control of the user. This is advantageous in that flower production, and subsequent events such as seed set, may be timed to meet market demands, for example, in cut flowers or decorative flowering pot plants. Delaying flowering in pot plants is advantageous to lengthen the period available for transport of the product from the producer to the point of sale and lengthening of the flowering period is an obvious advantage to the purchaser.

In a further aspect the present invention provides a gene construct comprising an inducible promoter operatively linked to a nucleotide sequence provided by the present invention, such as the FCA gene or *Arabidopsis thaliana*, a homologue from another plant species, e.g. a Brassica such as *Brassica napus*, or any mutant, variant or allele thereof. As discussed, this enables control of expression of the gene. The invention also provides plants transformed with said gene construct and methods comprising introduction of such a construct into a plant cell and/or induction of expression of a construct within a plant cell, by application of a suitable stimulus, an effective exogenous inducer.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype.

Suitable promoters include the Cauliflower Mosaic Virus 35S (CaMV 35S) gene promoter that is expressed at a high level in virtually all plant tissues (Benfey et al, 1990a and 1990b); the cauliflower meri 5 promoter that is expressed in the vegetative apical meristem as well as several well localised positions in the plant body, eg inner phloem, flower primordia, branching points in root and shoot (Medford, 1992; Medford et al, 1991) and the *Arabidopsis thaliana* LEAFY promoter that is expressed very early in flower development (Weigel et al, 1992).

When introducing a chosen gene construct into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Plants transformed with the DNA segment containing the sequence may be produced by standard techniques which are already known for the genetic manipulation of plants. DNA can be transformed into plant cells using any suitable technology, such as a disarmed Ti-plasmid vector carried by Agrobacterium exploiting its natural gene transfer ability (EP-A-270355, EP-A-0116718, NAR 12(22) 8711–87215 1984), particle or microprojectile bombardment (U.S. Pat. No. 5,100,792, EP-A-444882, EP-A-434616) microinjection (WO 92/09696, WO 94/00583, EP 331083, EP 175966), electroporation (EP 290395, WO 8706614) or other forms of direct DNA uptake (DE 4005152, WO 9012096, U.S. Pat. No. 4,684,611). Agrobacterium transformation is widely used by those skilled in the art to transform dicotyledonous species. Although Agrobacterium has been reported to be able to transform foreign DNA into some monocotyledonous species (WO 92/14828), microprojectile bombardment, electroporation and direct DNA uptake are preferred where Agrobacterium is inefficient or ineffective. Alternatively, a combination of different techniques may be employed to enhance the efficiency of the transformation process, eg bombardment with Agrobacterium coated microparticles (EP-A-486234) or microprojectile bombardment to induce wounding followed by co-cultivation with Agrobacterium (EP-A-486233).

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention.

In the present invention, over-expression may be achieved by introduction of the nucleotide sequence in a sense orientation. Thus, the present invention provides a method of influencing a flowering characteristic of a plant, the method comprising causing or allowing expression of the polypeptide encoded by the nucleotide sequence of nucleic acid according to the invention from that nucleic acid within cells of the plant.

Under-expression of the gene product polypeptide may be achieved using anti-sense technology or "sense regulation".

The use of anti-sense genes or partial gene sequences to down-regulate gene expression is now well-established. Double-stranded DNA is placed under the control of a promoter in a "reverse orientation" such that transcription of the "anti-sense" strand of the DNA yields RNA which is complementary to normal mRNA transcribed from the "sense" strand of the target gene. The complementary antisense RNA sequence is thought then to bind with mRNA to form a duplex, inhibiting translation of the endogenous mRNA from the target gene into protein. Whether or not this is the actual mode of action is still uncertain. However, it is established fact that the technique works. See, for example, Rothstein et al, 1987; Smith et al, 1988; Zhang et al, 1992, English et al 1996. The complete sequence corresponding to the coding sequence in reverse orientation need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A suitable fragment may have about 14–23 nucleotides, e.g. about 15, 16 or 17.

Anti-sense regulation may itself be regulated by employing an inducible promoter in an appropriate construct.

Thus, the present invention also provides a method of influencing a flowering characteristic of a plant, the method comprising causing or allowing anti-sense transcription from nucleic acid according to the invention within cells of the plant.

When additional copies of the target gene are inserted in sense, that is the same, orientation as the target gene, a range of phenotypes is produced which includes individuals where over-expression occurs and some where under-expression of protein from the target gene occurs. When the inserted gene is only part of the endogenous gene the number of under-expressing individuals in the transgenic population increases. The mechanism by which sense regulation occurs, particularly down-regulation, is not well-understood. However, this technique is also well-reported in scientific and patent literature and is used routinely for gene control. See, for example, van der Krol, 1990; Napoli et al, 1990; Zhang et al, 1992.

Thus, the present invention also provides a method of influencing a flowering characteristic of a plant, the method comprising causing or allowing expression from nucleic acid according to the invention within cells of the plant to suppress activity of a polypeptide with ability to influence a flowering characteristic. Here the activity of the polypeptide is preferably suppressed as a result of under-expression within the plant cells.

Modified version of FCA may be used in influencing a flowering characteristic of a plant. For example a mutant identified herein as fca-1, fca-3 or fca-4 may be employed. The sequence changes resulting in these mutants and the resulting phenotypes are discussed above.

Promotion of FCA activity to cause early flowering

Mutations that reduce FCA activity cause late flowering under both long and short day conditions, indicating FCA involvement in promoting flowering constitutively. Double mutant experiments have also indicated that FCA function may be required both upstream and downstream of the gene products involved in conferring inflorescence/floral meristem identity eg. LEAFY, APETALA1 and TERMINAL FLOWER. Thus FCA function may be involved in the ability of meristems to respond to LEAFY, APETALA1 and TERMINAL FLOWER gene products.

The fully spliced FCA transcript is present at very low abundance in all conditions so far analysed. Although the fca mutation is recessive transgenic fca plants homozygous for an introduced wild-type FCA gene flowered slightly earlier than plants carry one copy (Example 2), suggesting that under some conditions the level of the FCA transcript is limiting to flowering time. This indicates that flowering may be manipulated by using foreign promoters to alter the expression of the gene. In addition, the majority of the transcript is present in a form that cannot make active protein. Thus alternative splicing may be a specific control mechanism to maintain relatively low levels of the FCA protein. Alteration of this splicing pattern, for example by introducing an FCA gene lacking introns into plants, may give much higher levels of the FCA protein which in turn would give accelerated flowering.

Causing early flowering under non-inductive or inductive conditions

Wild-type Arabidopsis plants flower extremely quickly under inductive conditions and the FCA gene is expressed prior to flowering, although at a low level. The level of the FCA product may be increased by introduction of promoter, eg CaMV35S or meri 5, fusions. In addition, introduction of an FCA gene lacking introns may increase the level of FCA protein and cause early flowering in all conditions.

Inhibition of FCA activity to cause late flowering fca mutations cause late flowering of Arabidopsis. Transgenic approaches may be used to reduce FCA activity and thereby delay or prevent flowering in a range of plant species. A variety of strategies may be employed. This late flowering can then be overcome, if so desired, by giving the imbibed seed or plants of different ages, a vernalization treatment.

Expression of sense or anti-sense RNAs

In several cases the activity of endogenous plant genes has been reduced by the expression of homologous antisense RNA from a transgene, as discussed above. Similarly, the expression of sense transcripts from a transgene may reduce the activity of the corresponding endogenous copy of the gene, as discussed above. Expression of an antisense transcript from the FCA gene has been shown reduce activity of the endogenous gene and cause late flowering (Example 3).

Expression of modified versions of the FCA protein

RNA binding proteins have a modular structure in which amino acid sequences required for binding different RNA molecules are separate domains of the protein (Burd and Dreyfuss 1994). This permits the construction of truncated or fusion proteins that display only one of the functions of the RNA binding protein. In the case of FCA, modification of the gene in vitro and expression of modified versions of the protein may lead to dominant inhibition of the endogenous, intact protein and thereby delay flowering. This may be accomplished in various ways, including the following:

Expression of a truncated FCA protein.

Some multi-RNP motif proteins can bind different RNA sequences simultaneously. U1 A for example, binds to U1 small nuclear RNA through its first RNA-binding domain and to pre-mRNA sequences through its second, thus controlling splicing (Burd and Dreyfuss 1994). Expression of an FCA protein with only one of these RNP motifs may dominantly block FCA action, by preventing binding of the full size FCA protein. Also expression of a mutant FCA protein not encoding the C terminal sequences may prevent the correct alignment of the binding of the RNA molecule and so again block wild-type FCA binding.

Aspects and embodiments of the present invention will now be illustrated, by way of example, with reference to the accompanying figures. Further aspects and embodiments will be apparent to those skilled in the art. All documents mentioned in this text are incorporated herein by reference.

In the Figures:

FIG. 1 SEQ ID NO:1 shows a nucleotide sequence according to one embodiment of the invention, being the sequence of the genomic region encoding FCA obtained from *Arabidopsis thaliana*. Introns are shown in small letters, exons in capitals. Features: ▼(1118)—transcription start; □(1532–1534, 1568–70, 1601–1603)—putative translation start ATG; ₁β(2753)—Poly A site of β-transcript; ⊃ ⊂(7056–7377)—alternative splicing around intron 13; _(8771–73)—translation stop TAA; ₁(9256)—Poly A site. Additional translational stop codon at 3026–3028 within intron 3.

FIG. 2 SEQ ID NO:3 shows the predicted amino acid sequence derived from the nucleotide sequence encoding the FCA ORF.

FIG. 3 SEQ ID NO:2 shows the nucleotide sequence of the FCA α$_B$ gene, including 5' and 3' flanking sequences. The sequence within the ORF is that of one of the abundant transcripts, that is 19 introns have been spliced out but intron 3 remains. The position of termination of the other abundant transcript is indicated. Primer sequences are given in Table 2. Restriction sites: SalI—352; HindIII—776; XbaI—1157; HindIII—3125; BglII—3177; ClaI—3293; BamHI—3549; HindIII—4728; SpeI—5003. Other important landmarks: 1293-poly A tail added after this nucleotide in cDNA clone 77B or FCA transcript α; 897-5' splice site of intron 3: 2973 3' splice site of intron 3.

FIG. 4 SEQ ID NOs:6–8, 27–31 compares the FCA RRM motifs with those from the Drosophila SEX-LETHAL and TRA-2 genes. Also shown are the C-terminal amino acids with homology to yeast and *C. elegans* proteins.

FIG. 5 shows the recombination analysis to position the FCA gene.

FIG. 8 shows the nucleotide sequence of the *Brassica napus* FCA homologue and encoded polypeptide: FIG. 8*a* SEQ ID NO:4—Brassica FCA nucleotide sequence including coding sequence; FIG. 8*b* SEQ ID NO:5—polypeptide amino acid sequence encoded by coding sequence of FIG. 8*a*.

FIG. 9 shows an alignment of the Arabidopsis and Brassica FCA amino acid sequences. Topline is Arabidopsis; SEQ ID NO:26 bottom line is Brassica.

Figure 10:
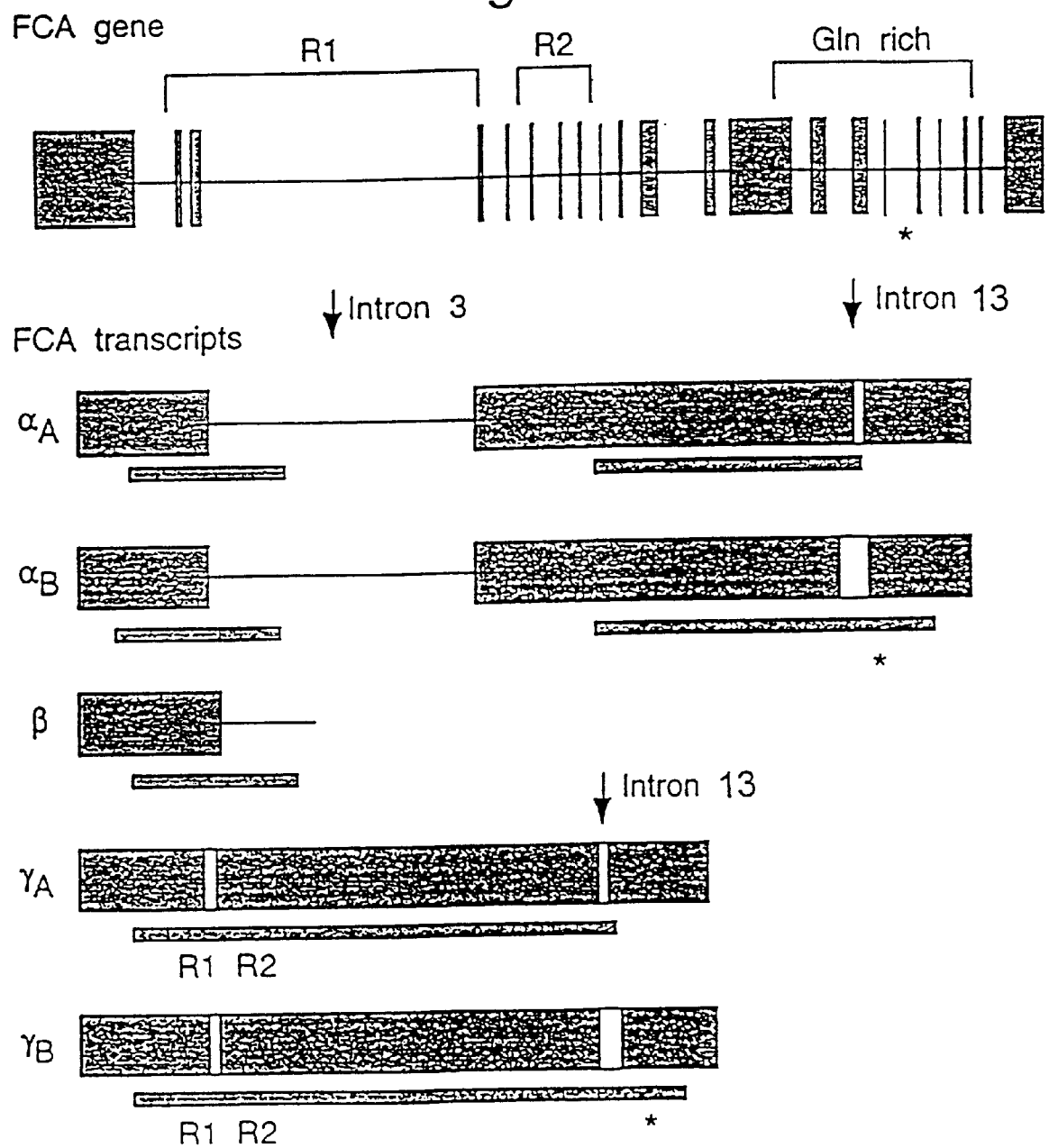

FIG. 10 shows the different transcripts produced from the FCA gene. _ open reading frame; * conserved region in *C. elegans* and yeast ESTs; R1, R2 RNA-binding domains 1 and 2.

EXAMPLE 1

Cloning and Analysis of the FCA Gene

Identification of a 300 kb genomic region carrying the FCA gene of *Aribidopsis thaliana*.

The fca mutation had been mapped relative to visible markers to 29 cM on chromosome 4. In order to map the locus relative to molecular markers as a starting point for cloning by chromosome walking, the segregation pattern of RFLP markers mapping to the top half of chromosome 4 was analysed in 171 late (homozygous recessive class) flowering individuals from the F2 of a cross between the late flowering mutant fca-1 (in a Landsberg erecta background) and the polymorphic early flowering ecotype Columbia. This analysis positioned the FCA locus in a 5.2 cM interval between markers m326 and m226.

These markers were then used as the starting points for the chromosome walk. YAC clones containing these RFLP markers were identified by colony hybridization experiments. In the initial experiments, the YAC libraries used were the EG, EW and ABI libraries but as another became available (yUP-May 1992) they were incorporated into the analysis. Positively hybridizing YAC clones were confirmed using Southern blot analysis. They were sized using PFGE and Southern blot analysis and then end-probes were generated using either inverse PCR or left-end rescue for use in chromosome walking experiments. In the majority of cases, each step in the walk was covered by two independent YAC clones to avoid false linkages generated by chimaeric YAC clones. These constituted a significant fraction of the EG, EW and yUP libraries and complicated the assembly of the YAC contig. The result of the generation and analysis of 65 end-probes was a YAC contig covering the m326-m226 interval that included 57 YAC clones.

Polymorphisms between Landsberg erecta and Columbia were determined for the left end-probe of EG9D2, right end-probe of YAC clone yUP13C7, right end-probe of YAC clone yUP3F7 and right end-probe of YAC clone EW20B3. Analysis of the segregation pattern of these markers on pooled progeny of recombinants with cross-over points mapping in the m326-m226 interval defined the region carrying the FCA gene to between the polymorphisms identified by yUP3F7RE and m226. This interval was covered by two overlapping YAC clones EW20B3 and ABI10C10.

In order to further define the position of the FCA gene, more probes were required that mapped within the two overlapping YAC clones. This was achieved by using end-probes from YAC clones ABI3C4, ABI6C3, a random Sau3A fragment from YAC clone EW20B3 (W5) and two cosmids cAtA2 and g19247. Restriction maps for SmaI, MluI and PacI were constructed and used to position the probes within the YAC clones.

Additional recombinants, where the cross-over point mapped close to the FCA locus, were generated by selecting individual plants that were arabinose resistant and had an early/intermediate flowering from the F2 generation of a cross between fca (in Landsberg erecta) and ara1 (in Columbia). Progeny of these were checked to confirm that they were homozygous for the arabinose resistance allele and heterozygous for the fca mutation. Three of these individuals (A2/7, A1/8 and A4/7) were analysed with the RFLP markers 3F7RE, W5, cAtA2, 19247, 3C4LE, 6C3LE and 226. This defined the north end of the genomic region carrying the FCA gene as within the cosmids cAtA2 and 19247. This information is summarized in FIG. 5.

Complementation analysis to define the FCA gene.

The two YAC clones EW20B3 and ABI10C10 were gel-purified and hybridized to filters carrying 25500 cosmid clones that contained 15–20 kb of *Arabidopsis thaliana* Landsberg erecta genomic DNA. This cosmid library was constructed in a new vector (04541) by cloning a 1.6 kb BglII fragment from pHC79 carrying the lambda cos fragment into in the vector pSLJ1711. The resulting highly stable cosmid cloning vehicle carries Agrobacterium border sequences for transfer of DNA into plant chromosomes, a 35S-NPTII plant selectable marker, lacz-laci sequences for the blue/white insert selection in *E.coli* and a polylinker with 7 cloning sites.

Positively hybridizing colonies were analysed by hybridizing each clone to Southern blots carrying all the cosmid clones digested with a HindIII, EcoRI and BamHI. This generated a restriction map for the insert of each cosmid and indicated which clones carried overlapping inserts. The cosmids were also run alongside plant DNA and hybridized with the cosmid to confirm that the cosmid insert was colinear with the plant DNA. The two cosmid clones, cAtA2 and cAtB1, mapping to this interval were isolated from a different cosmid library (Olszewski and Ausubel 1988). The result of this analysis was a cosmid contig covering the 300 kb interval in which the FCA locus had been defined.

Six mutant fca alleles were available, two of which had been generated by FN irradiation and one by X-ray irradiation. Irradiation-induced mutations are frequently associated with genomic rearrangements or deletions. In case this would further refine the location of the FCA gene, the genomic region covered by the YAC clones EW20B3 and ABI10C10 was examined in all six alleles. The two YAC clones were hybridized to PFGE Southern blots carrying DNA from the different alleles digested with SmaI and MluI. A ~50 kb MluI fragment was found to be slightly smaller in the fca-4 allele. Further analysis by hybridization of cosmid clones, corresponding to the region showing the difference, indicated that part of the alteration had occurred in a 1.9 kb BamHI fragment carried in cosmids cAtA2 and 19247. This focused our efforts in the first complementation experiments to cosmid clones at the north end of the contig.

Figure 6:
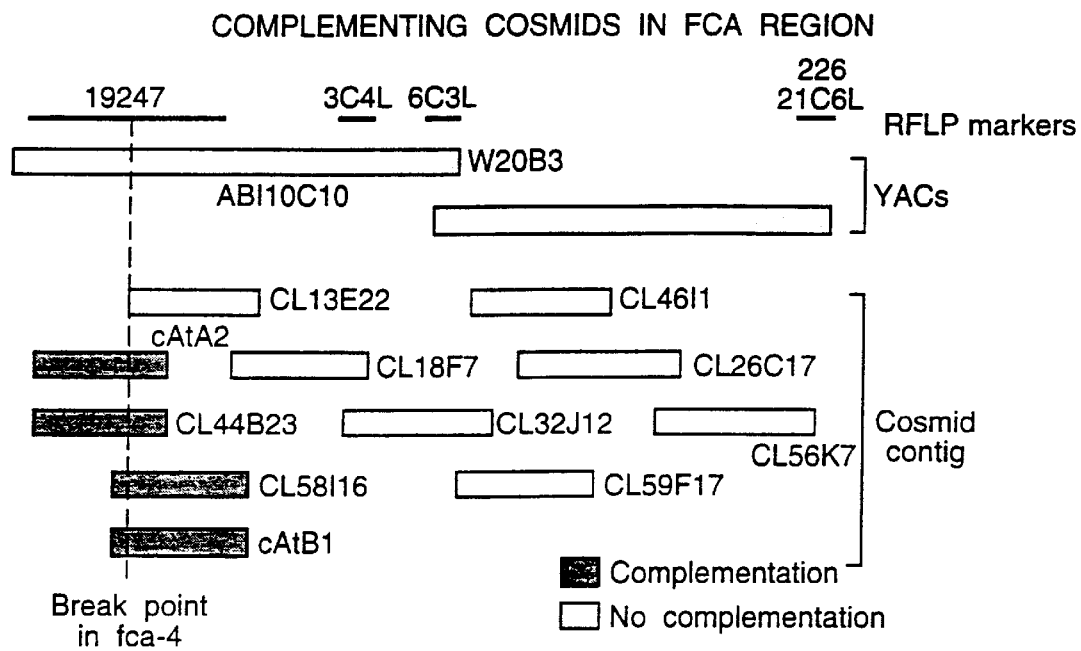
FIG. 6 shows the complementation analysis to localize the FCA gene.

Eleven cosmid clones shown in FIG. 6, starting with those at the left end, were introduced into the Arabidopsis fca-1 mutant using the root explant transformation procedure (Valvekens et al 1988). Seed were collected from self-fertilized kanamycin resistant individuals and analysed with respect to their kanamycin segregation and flowering time. The number of transformants showing complementation to early flowering for each cosmid is shown in FIG. 6. The four cosmids that resulted in complementation mapped to the end of the genomic region where the inversion in the fca-4 allele mapped.

Identification of the FCA gene.

The complete genomic sequence of Columbia allele corresponding to the genomic region within the complementing cosmid clones was obtained through the efforts of the Arabidopsis sequencing initiative centred within this department (G. Murphy pers. comm.). The majority of the genomic region contained in the complementing cosmids is carried on three BamHI restriction fragments, 4, 1.9 and 2 kb. These were isolated and hybridized either separately or pooled to $1 \times 10^6$ phage clones of the PRL-2 cDNA library. This library had been made from pooled RNA samples and was made available by Tom Newman (Michigan). Four clones hybridizing to the 2 kb BamHI fragment and 3 to the 4 and 1.9 kb fragments were isolated and characterized. They identified two cDNA clones with insert sizes ~1700 bp and 1350 bp. Analysis of the sizes of the transcripts hybridizing to these two cDNA clones showed that one (in fca-4) was reduced in size relative to the other alleles and wild-type and so this cDNA clone was assigned to the FCA gene. The other clone showed no differences and was termed 77B The transcript size of the putative FCA gene was >3 kb indicating that the cDNA clone was not full length. The cDNA clone was sequenced and found to encode an insert of 1811 bp. Primers were designed from the genomic sequence (marked BamX primer on FIG. 3) and the 5' end of the cDNA sequence (marked IanRT1 and IanRT2 on FIG. 3). First strand cDNA was made using the IanRT2 primer to prime RNA isolated from wild-type seedlings (2 leaf stage). This was used with primers BamX and IanRT2 to PCR amplify a fragment detected as a faint band on an ethidium bromide stained gel. The PCR product was diluted 1/300 and reamplified using primers BamX and IanRT1. The product from this reaction was end-filled using T4 DNA polymerase and cloned into the EcoRV site of the general cloning vector Bluescript KSII (Stratagene). The product was sequenced and found to be colinear with the genomic sequence and extend the sequence of the cDNA clone by 735 bp.

The sequence was compared to all available sequences using BlastX, BlastN and TBlastN. Significant homologies were detected in the TBlastN search to a class of proteins previously defined as RNA binding proteins. The characteristic of these proteins is the presence of one or more RRM motifs made up of conserved amino acids covering an 80 amino acid region (shown in FIG. 4). The positioning of sub-motifs RNP2 and RNP1 and individual conserved amino acids is always maintained within the whole RRM motif. Translation of the sequence of the FCA cDNA clone extended in the RT-PCR experiments showed the presence of multiple translation stop codons in the 5' region of the sequence. The first methionine residue downstream of the last translation stop codon and in frame with the rest of the FCA protein was located in the middle of the RRM motif, splitting RNP2 and RNP1. The strong homology of the RRM motif to other RNA binding proteins suggested that this MET residue was not the beginning of the FCA protein. In addition, the transcripts of a large number of RNA-binding proteins are alternatively spliced to yield active and inactive products. The splicing is then regulated, often in an autoregulatory fashion, to control the production of the active protein. These facts suggested that the FCA transcript generated in the RT-PCR experiments contained an intron, just upstream of the RRM motif.

In order to test this hypothesis, several primers were designed from the genomic sequence for use in further RT-PCR experiments. First strand cDNA was made from RNA isolated from seedlings (4 leaf stage), primed with random hexamers (Boehringer). Primers lying within the sequence 5' to the FCA cDNA up to the 3' end of the 77B cDNA (the other cDNA clone hybridizing to the complementing cosmid clones), together with IanRT1 gave amplification products of the expected size from the genomic sequence but did not yield smaller products as would be expected from a transcript in which an intervening intron had been spliced out. A primer lying is within the 77B cDNA clone marked as cDNAII-BamHI (in FIG. 3) was then used in conjunction with the IanRT1 primer. No band was visible on an ethidium bromide stained agarose gel after 30 cycles of amplification. The PCR reaction was then diluted 1/300 and re-amplified using primers cDNAII-1 and RevEx4 (shown in FIG. 3). The PCR product was digested with SalI and BglII restriction enzymes and cloned into SalI and BamHI digested BluescriptKSII plasmid. Sequence analysis of the 760 bp product and comparison to the genomic sequence revealed that a 2 kb intron had been spliced out to join the ORF within the 77B cDNA to that carrying the RRM motif in the FCA gene. This splicing revealed the presence of a second intact RRM motif interrupted by intron 3.

Direct comparison of the FCA sequence with that of LUMINIDEPENDENS and CO, the other flowering time genes cloned from Arabidopsis (Lee et al, 1994, Putterill et al 1995), detected no significant homology.

Mutations in the fca mutant alleles.

cDNA was made from RNA isolated from the mutant alleles. This was amplified using cDNAII-BamHI and cDNA-3'a: BamX and IanRT1; fca5'-1 and fca3'-a (positions indicated on FIG. 3). The resulting PCR fragments were cloned and sequenced and compared to the sequence of the wild-type Landsberg erecta transcript. The fca-1 mutation converted a C nucleotide at position 6861 into a T. Thus a glutamine codon (CAA) is changed into a stop codon (TAA). The fca-3 mutation converted a G nucleotide at position 5271 into an A. The effect of this mutation is to alter the 3' splice junction of intron 7 such that a new 3' splice junction is used 28 nucleotides into exon 8. The fca-4 mutation is the result of a rearrangement with the breakpoint at position 4570 (within intron 4).

EXAMPLE 2

Isolation and Sequence Analysis of the *Brassica napus* Homologue

A *Brassica napus* genomic library constructed from Sau3A partially digested DNA cloned into lambda DASH$^R$II/BamHI vector (stratagene) was obtained. The library was screened using the 1811 bp FCA cDNA clone. A clone carrying a 12 kb insert was isolated which hybridized to the FCA cDNA clone and the 77B cDNA clone. The lambda clone was digested with SalI which released the full length 12 kb Brassica insert and this was cloned into Bluescript KSII. Restriction fragments of this clone (a combination of EcoRI, SacI and BamHI) were subcloned into BluescriptKSII and sequenced.

The 12 kb Brassica fragment was also subcloned into the XhoI restriction site of the Agrobacterium binary vector pSLJ1714 (Jones et al 1992), for transformation into the fca mutant. When introduced into the fca-4 mutation, using root explant transformation, progeny of the transformant segregated early flowering plants. These flowered with a mean of 8.3 leaves compared to wild-type Landsberg erecta grown alongside with 9.1 leaves and fca-4 with 24.1 leaves. Thus the Brassica FCA gene fully complements the fca-4 mutation.

Expression of FCA mRNA

PolyA mRNA was isolated from a range of developmental stages: 2 leaf, 4 leaf, 6 leaf and 10 leaf, roots and inflorescences, fractionated on Northern blots and hybridized with the 1811 bp FCA cDNA clone. The combined FCA transcript γ was present at approximately the same amount in all tissues examined except for the inflorescences where expression was slightly lower. The prematurely polyadenylated transcript β was detected using 77B cDNA clone as a probe. The β transcript was ~20-fold more abundant than $\gamma_{A+B}$. Transcripts $\alpha_{A+B}$ containing intron 3 were not detected on a northern blot and could only be found using RT-PCR.

FCA expression has also been analysed using RNase protection assays. Using a probe (725 bp to 1047 bp from $\gamma_B$ construct) the $\gamma_{A+B}$ transcripts were detected at similar levels in a range of developmental stages in both long and short day photoperiods, and at lower levels in rosettes and inflorences of mature plants. The β transcript was at a higher level in these tissues consistent with the northern blot analysis.

METHODS FOR EXAMPLES 1 AND 2

Growth Conditions and Measurement of Flowering Time

Flowering time was measured under defined conditions by growing plants in Sanyo Gallenkamp Controlled Environment rooms at 20° C. Short days comprised a photoperiod of 10 hours lit with 400 Watt metal halide power star lamps supplemented with 100 watt tungsten halide lamps. This provided a level of photosynthetically active radiation (PAR) of 113.7 μmoles photons m-2s-1 and a red:far red light ratio of 2.41. A similar cabinet and lamps were used for the long day. The photoperiod was for 10 hours under the same conditions used for short days and extended for a further 8 hours using only the tungsten halide lamps. In this cabinet the combination of lamps used for the 10 hour period provided a PAR of 92.9 μmoles photons m-2 s-1 and a red:far red ratio of 1.49. The 8 hour extension produced PAR of 14.27 μmoles m-2 s-1 and a red:far-red ratio of 0.66.

The flowering times of large populations of plants were measured in both greenhouse and cabinet conditions. Flowering time was measured by counting the number of leaves, excluding the cotyledons, in the rosette and on the inflorescence. Leaf numbers are shown with the standard error at 95% confidence limits. The number of days from sowing to the appearance of the flower bud was also recorded, but is not shown. The close correlation between leaf number and flowering time was previously demonstrated for Landsberg erecta and fca alleles (Koorneef et al, 1991).

Cosmid and RFLP markers.

DNA of lambda clones m210, m326, m580, m226 were obtained from Elliot Meyerowitz (Caltech, Pasadena). Total DNA was used as radiolabelled probe to YAC library colony filters and plant genomic DNA blots. Cosmids g10086, g4546, g4108, g19247 were obtained from Brian Hauge and Howard Goodman (MGH, Boston), cultured in the presence of 30 mg/l kanamycin, and maintained as glycerol stocks at −70° C. Total cosmid DNA was used as radiolabelled probe to YAC library colony filters and plant genomic DNA blots. Cosmid clones cAtA2 and cATB1 were obtained from Chris Cobbett (University of Melbourne) and cultured in the presence of 10 mg/l tetracycline. Cosmid pCITd23 was provided by Elliot Meyerowitz (Caltech, Pasadena), cultured in the presence of 100 μg/ml streptomycin/ spectinomycin and maintained as a glycerol stock at −70° C. pCIT30 vector sequences share homology to pYAC4 derived vectors, and therefore YAC library colony filters were hybridised with insert DNA extracted from the cosmid. Total DNA of pCITd23 was used as radiolabelled probe to plant genomic DNA blots.

YAC libraries.

The EG and ABI libraries were obtained from Chris Somerville (Michigan State University). The EW library was obtained from Jeff Dangl (Max Delbruck Laboratory, Cologne) and the yUP library from Joe Ecker (University of Pennsylvania). Master copies of the libraries were stored at −70° C. (as described by Schmidt et al. Aust. J. Plant Physiol. 19: 341–351 (1992)). The working stocks were maintained on selective Kiwibrew agar at 4° C. Kiwibrew is a selective, complete minimal medium minus uracil, and containing 11% Casamino acids. Working stocks of the libraries were replated using a 96-prong replicator every 3 months.

Yeast colony filters.

Hybond-N (Amersham) filters (8 cm×11 cm) containing arrays of yeast colony DNA from 8–24 library plates were produced and processed (as described by Coulson et al. Nature 335:184–186 (1988) and modified (as described by Schmidt and Dean Genome Analysis, vol.4: 71–98 (1992)). Hybridisation and washing conditions were according to the manufacturer's instructions. Radiolabelled probe DNA was prepared by random-hexamer labelling.

Yeast chromosome preparation and fractionation by pulsed field gel electrophoresis (PFGE).

Five milliliters of Kiwibrew was inoculated with a single yeast colony and cultured at 30° C. for 24 h. Yeast spheroplasts were generated by incubation with 2.5 mg/ml Novozym (Novo Biolabs) for 1 h at room temperature. Then 1 M sorbitol was added to bring the final volume of spheroplasts to 50 μl. Eighty microliters of molten LMP agarose (1% InCert agarose, FMC) in 1 M sorbitol was added to the spheroplasts, the mixture was vortexed briefly and pipetted into plug moulds. Plugs were placed into 1.5 ml Eppendorf tubes and then incubated in 1 ml of 1 mg/ml Proteinase K (Boehringer Mannheim) in 100 mMEDTA, pH 8, 1% Sarkosyl for 4 h at 50° C. The solution was replaced and the plugs incubated overnight. The plugs were washed three times for 30 min each with TE and twice for 30 min with 0.5×TVBE. PFGE was carried out using the Pulsaphor system (LKB). One-third of a plug was loaded onto a 1% agarose gel and electrophoresed in 0.5×TBE at 170 V,20 s pulse time, for 36 h at 4° C. DNA markers were concatemers of lambda DNA prepared as described by Bancroft and Wolk, Nucleic A Res. 16:7405–7418 (1988). DNA was visualised by staining with ethidium bromide.

Yeast genomic DNA for restriction enzyme digestion and inverse polymerase chain rection (IPCR).

Yeast genomic DNA was prepared essentially as described by Heard et al. (1989) except that yeast spheroplasts were prepared as above. Finally, the DNA was extracted twice with phenol/chloroform, once with chloroform and ethanol precipitated. The yield from a 5 ml culture was about 10 μg DNA.

Isolation of YAC left-end probes by plasmid rescue.

Plasmid rescue of YAC left-end fragments from EG, ABI and EW YACs was carried out as described by Schmidt et al. (1992). IPCR was used to generate left and right end fragments using the protocol and primers described in Schmidt et al (1992).

Gel blotting and hybridisation conditions.

Gel transfer to Hybond-N, hybridisation and washing conditions were according to the manufacturer's instructions, except that DNA was fixed to the filters by UV Stratalinker treatment and/or baked at 80° C. for 2 h.

Hybridization protocol:

1) Make up a pre-hydridization solution as follows (for 25 ml)

| Solution | Volume | Final concentration |
| --- | --- | --- |
| 20 × SSPE | 6.25 ml | 5 × SSPE |
| 100 × Denhardt's solution | 1.25 ml | 5 × Denhardt's solution |
| 10% (w/v)SDS | 1.25 ml | 0.5% (w/v)SDS |

Make up to 25 ml with sterile water. Add to the membrane in a hybridization box or bag.

2) Denature 0.5 ml of a 1 mg/ml solution of sonicated non-homologous DNA by heating to 100° C. for 5 minutes. Chill on ice and add to prehybridization solution.
3) Prehybridize in a shaking water bath at 65° C. for 1 hour.
4) Denature labelled probe (unless using an RNA or ssDNA probe) by heating to 100° C. for 5 minutes. Add the probe to the prehybridization solution.
5) Incubate for at least 12 hours at 65° C. (Amersham supply a rapid hybridization system that allows hybridization to take place in 1–2 hours with no loss in sensitivity).
6) Following hybridization, wash the filters by incubating them in 2×SSPE, 0.1% (w/v) SDS at room temperature for 10 minutes. Repeat.
7) Replace the solution with 1×SSPE, 0.1% (w/v) SDS. Incubate at 65° C. for 15 minutes.
8) Replace the solution with 0.1×SSPE, 0.1% (w/v) SDS. Incubate at 65° C. for 10 minutes. Repeat if necessary. Note: This is a high stringency wash and should be omitted if related sequences are to be probed.
9) Remove filter, wrap in SaranWrap and carry out autoradiography. SaranWrap should not be used if the probe is labelled with sulphur-35.

Other published protocols may also be successfully used with Hybond N+. Detailed protocols for ECL probe labelling and hybridization can be found in the appropriate ECL system handbook. Radiolabelled DNA was prepared by random hexamer labelling.

RFLP analysis.

Two to three micrograms of plant genomic DNA was prepared from the parental plants used in the crosses and cleaved in a 300 μl volume. The digested DNA was ethanol precipitated and separated on 0.7% agarose gels and blotted onto Hybond-N filters. Radiolabelled cosmid, lambda or YAC end probe DNA was hybridised to the filters to identify RFLPs.

RNA extractions

RNA was extracted using a method described by Dean et al (1985) polyA RNA was isolated using the polyAtract$^R$ mRNA isolation system (Promega).

DNA extractions

Arabidopsis DNA was performed by a CTAB extraction method described by Dean et al (1992).

Isolation of cDNA by RT-PCR

Total RNA was isolated from whole seedlings at the 2–3 leaf stage growing under long days in the greenhouse. For first strand cDNA synthesis, 10 μg of RNA in a volume of 10 μl was heated to 65° C. for 3 minutes, and then quickly cooled on ice. 10 μl of reaction mix was made containing 1 μl of RNAsin, 1 μl of standard dT17-adapter primer (1 μg/μl; Frohman et al, 1988), 4 μl of 5× reverse transcriptase buffer (250 mM TrisHCl pH8.3, 375 mM KCl, 15 mM MgCl2), 2 μl DTT (100 mM), 1 μl dNTP (20 mM), 1 μl reverse transcriptase (200 units, M-MLV Gibco). This reaction mix was then added to the RNA creating a final volume of 20 μl. The mixture was incubated at 42° C. for 2 hours and then diluted to 200 μl with water.

10 μl of the diluted first strand synthesis reaction was added to 90 μl of PCR mix containing 4 μl 2.5 mM dNTP, 10 μl 10×PCR buffer (Boehringer plus Mg), 1 μl of a 100 ng/μl solution of each of the primers, 73.7 μl of water and 0.3 μl of 5 units/μl Taq polymerase (Boehringer or Cetus Amplitaq). The reaction was performed at 94° C. for 1 minute, 34 cycles of 55° C. for 1 minute, 72° C. for 2 minutes and then finally at 72° C. for 10 minutes.

DNA sequencing

The Sanger method was used to sequence fragments of interest inserted in a Bluescript plasmid vector. Reactions were performed using a Sequenase kit (United States Biochemical Corporation).

Screening the Landsberg erecta cosmid library and the PRL-2 cDNA library.

26000 clones arrayed in microtitre plates were screened by gridding offsets from 16 microtitre plates onto LB-tet (10 μg/ml) plates and then taking colony lifts onto Hybond N filters. 1×106 plaques of the CD4-71-PRL2 library (supplied by the Arabidopsis Biological Resource Center at Ohio State University) were screened by plating 20 plates of 50000 plaques and then taking plaque lifts onto Hybond N filters.

Transformation of Arabidopsis

The cosmids containing DNA from the vicinity of FCA were mobilised into *Agrobacterium tumefaciens* C58C1, and the T-DNA introduced into Arabidopsis plants as described by Valvekens et al, 1988. Roots of plants grown in vitro were isolated and grown on callus-inducing medium (Valvekens et al, 1988) for 2 days. The roots were then cut into short segments and co-cultivated with *Agrobacterium tumefaciens* carrying the plasmid of interest. The root explants were dried on blotting paper and placed onto callus-inducing medium for 2–3 days. The Agrobacterium were washed off, the roots dried and placed onto shoot inducing medium (Valvekens et al, 1988) containing vancomycin to kill the Agrobacterium and kanamycin to select for transformed plant cells. After approximately 6 weeks green calli on the roots start to produce shoots. These are removed and placed in petri dishes or magenta pots containing germination medium (Valvekens et al, 1988). These plants produce seeds in the magenta pots. These are then sown on germination medium containing kanamycin to identify transformed seedlings containing the transgene (Valvekens et al, 1988).

EXAMPLE 3

Plants Homozygous for the T-DNA Insertion Carrying FCA Flower Earlier than Heterozygotes Two transformants of each of the four cosmid clones that complemented the fca mutant phenotype were selfed and seed of late and early flowering individuals were collected and plated on kanamycin-containing medium. All the late flowering progeny were kanamycin sensitive whilst progeny from the early flowering individuals were either homozygous or heterozygous for kanamycin resistance. This demonstrates that the kanamycin marker on the T-DNA carrying the region containing the FCA gene completely co-segregated with the early flowering phenotype. Thus, complementation to early flowering was due to sequences within the insert of the cosmid. LN was counted for the early flowering individuals either homozygous or heterozygous for the T-DNA insert.

TABLE 1

| cosmid | K/K | K/- |
|---|---|---|
| CL58I16 | 10.3 (9) | 13 (4) |
|  | 9.7 (4) | 10.4 (10) |
| CL44B23 | 9,5 (2) | 11.8 (6) |
|  | 12 (2) | 11.1 (6) |
| cAtA1 | 14.2 (5) | 15 (3) |
|  | 9.6 (3) | 10.8 (5) |
| cAtA2 | 9.1 (7) | 9.3 (3) |
|  | 12.5 (3) | 14.4 (7) |

Analysis of flowering time (as measured by total LN) in transformants showing complementation of the fca mutant phenotype. For each cosmid two independent transformants were analysed. The leaf number was counted on F2 individuals (the number of which is shown in the bracket) which were then selfed and progeny sown on kanamycin-containing medium to establish whether the plant was homozygous (K/K) or heterozygous (K/-) for the T-DNA insert.

The results, shown in Table 1 above, indicate that the homozygotes flowered significantly earlier than the heterozygotes in all 8 transformants analysed. Thus increasing the FCA gene dosage and therefore most likely the amount of gene product causes earlier flowering.

EXAMPLE 4

Antisense Experiments

A 1184 bp BamHI (bp3547, FIG. 3)/HindIII (bp4731 FIG. 3) restriction fragment from the FCA cDNA clone was subcloned into the BamHI/HindIII restriction sites of pBluescriptKSII. The insert was released with the enzymes BamHI and XhoI and subcloned into an Agrobacterium binary vector pSLJ6562 (J. Jones, Sainsbury Laboratory). The resulting plasmid contains the CaMV 35S promoter transcribing the FCA cDNA fragment to produce antisense RNA, terminated with 3' sequences from the nopaline synthase gene. This plasmid also carries LB and RB Agrobacterium sequences for delivery into plant cells and and a nos5'-kan-ocs3' fusion to allow kanamycin selection for transformants. The construct was introduced into *Arabidopsis thaliana* ecotype Landsberg erecta using the root explant transformation procedure of Valvekens et al (1988).

Selfed seed from five transformants were collected, sown on kanamycin-containing medium and and 10 kanamycin resistant individuals transplanted to soil. Three of the transformants segregated for a single T-DNA insertion, the other had two or more. Flowering time, assayed as rosette leaf number was measured. Progeny from four of the five transformants were late flowering, producing 12 rosette leaves, compared to 4 for the fifth transformant. Grown alongside, in these particular conditions, non-transformed Landsberg erecta and fca-1 plants flowered with ~4 and 11 rosette leaves respectively. Thus the antisense construct (as a single locus) effectively reproduced the late flowering phenotype of the fca-1 mutation.

EXAMPLE 5

Construction of Promoter Fusions to the FCA Open Reading Frame

A genomic SalI-XhoI fragment carrying the whole FCA gene plus 64 bp upstream of the putative start of translation and 500 bp downstream of the site of polyadenylation was cloned into the XhoI site of the Agrobacterium binary vector pSLJ 6562 (described above). This resulted in a vector carrying a nos-kan fusion for transformant selection and a fusion where the 35S promoter is driving the FCA genomic region (21 exons, 20 introns). Tranformants have been made using this construct.

This construct when introduced into fca-4 plants corrected the late flowering phenotype causing the plants to flower with 6.4 leaves under a long-day photoperiod. This was similar to wild-type Landsberg erecta which flowered with 6.2 leaves when grown alongside.

EXAMPLE 6

Construction of an FCA Gene Lacking Introns—Transcripts $\gamma_A$ and $\gamma_B$ The $\gamma_A$ construct was created by cloning together seven fragments:

i. an EcoRI (a site present to the insert junction in the multiple cloning site of the vector)—SalI fragment from the cosmid CL43B23. This fragment contains the 5' promoter and untranslated region of FCA and the 5' region of the ORF.

ii. a 425 bp SalI-HindIII restriction fragment from cDNA clone 77B.

iii. the region of the spliced transcript covering the 5' splice site of intron 3 was generated using RT-PCR with primers cDNAII-BamHI and IanRT1. The product was reamplified using cDNAII-1 and RevEx4, digested with SalI and BglII and cloned into pBluescriptKSII digested with SalI and BamHI. A 270 bp HindIII fragment from this plasmid was then used in the reconstruction of the fully spliced transcript.

iv. a region of the spliced transcript was amplified using RT-PCR and primers BamX and IanRT1. This was digested with HindIII and BglII and the 52 bp fragment used in the reconstruction of the fully spliced transcript.

v. a region of the spliced transcript was amplified using RT-PCR and primers BamX and Rev404 (position indicated on FIG. 3). A 256 bp ClaI-BamHI fragment was released and gel-purified for use in the reconstruction of the fully spliced transcript.

vi. a ClaI-SpeI fragment was excised from the FCA cDNA clone (the 1811 bp clone isolated from the PRL-2 library)

vii. a SpeI-XhoI fragment, carrying the last ~140 bp of 3' untranslated region plus ~500 bp of 3' genomic sequence, was isolated from the FCA genomic clone.

The seven fragments used to construct the FCA gene lacking introns were assembled in two parts, 5' region and then 3' region, which were then combined.

A. 5' region. Fragment iv was cloned into pBluescriptKSII as a HindIII/ClaI insert. Fragment ii was then cloned into this as an EcoRI/HindIII fragment (the EcoRI site coming from the multi-cloning site in the cDNA cloning vector). Fragment iii was then cloned into the HindIII site between fragments ii and iv, the correct orientation being determined using an asymmetrically positioned RsaI site. Fragment i was then cloned into the EcoRI/SalI sites.

B. 3' region. Fragment vii was cloned into the SpeI/XhoI sites present in fragment vi (the XhoI site coming from the multiple cloning site in the vector). Fragment v was then cloned into the BamHI site, the correct orientation being determined using an asymmetrically positioned ClaI site.

The 3' region containing fragments v, vi and vii was then cloned into the plasmid containing the 5' fragments as a ClaI/XhoI fragment.

The $\gamma_B$ construct was generated by replacing the EcoNI fragment (1503 bp to 2521 bp of spliced transcript) with an EcoNI fragment from a clone derived from RT-PCR from Ler RNA that contained the alternatively spliced form encoding the full length protein.

The resulting constructs were released from the vector using EcoRI and XhoI and cloned into the EcoRI/XhoI sites of the Agrobacterium binary vector pSLJ1714 (Jones et al 1992). Transformants carrying this construct have been generated.

Construct $\gamma_A$ when introduced into Landsberg erecta caused it to flower with 5.6 leaves under a long-day photoperiod. This was slightly earlier than wild-type Landsberg erecta which flowered with 6.2 leaves when grown alongside. When grown under short-day photoperiod ¼ of the progeny from the tranformant flowered early (with an average of 8.7 leaves). This is significantly earlier than wild-type Landsberg erecta which flowers with 23.5 leaves under these conditions.

EXAMPLE 7

Expression in E. coli

The $\gamma_B$ construct, described in Example 6, was digested with SalI and KpnI and cloned into the XhoI-KpnI sites of the E. coli expression vector pRSETC (Invitrogen Corp.). The resulting vector has the FCA cDNA cloned in frame with a polyhistidine metal binding domain, which enables the recombinant protein to be purified away from native E.coli proteins using a metal affinity resin (ProBond™ Ni$^{2+}$, Invitrogen Corp.). The FCA protein did not bind well to the affinity columns and so was separated from the E.coli proteins by excision from an SDS-polyacrylamide gel. Protein was extracted from the gel slice and used to inject rabbits. A booster jab was given and then two bleeds taken. The antibodies produced detect the FCA protein dot blotted onto nylon membrane at >1/10,000 dilution.

EXAMPLE 8

Primers Designed to Amplify Genes Containing RRM Domains with High Homology to FCA Based on the homology between etr-1, an EST derived from a human brain mRNA (dbest H1995); the Drosophila sexlethal protein; the human nervous system proteins HuD, HuC, Hel-N1, and Hel-N2; and the Xenopus proteins elrA, elrB, elrC, elrD a set of degenerate PCR primers were designed containing two regions of very high homology.

```
Amino acid   F   V   G   S   L   N   K           (SEQ ID NO:9)

OLIGO 1 5'  TTT GTG GGG AGG CTG AAC AAG  C 3'   (SEQ ID NO:10)
                C   A   ATCAT A   T   A
                T   T   T   T
                C   C   C   C

Amino acid   R   G   C   F   V   K   Y           (SEQ ID NO:11)

OLIGO 1 3'  TCC GAC GCC GAA GCA GTT TAT  5'     (SEQ ID NO:12)
                A   A   A   A   C
                T       T       T
                C       C       C
```

EXAMPLE 9

Construction of FCA Derivatives to Generate Dominant Negative Mutations and to Analyse the Expression and Splicing Pattern of the FCA Gene A construct expressing the second open reading frame of transcript $\alpha_B$ under the control of the FCA promoter, was constructed by deleting the first open reading frame (from 450 bp to 1206 bp). This was done using oligo mutagenesis to introduce a SphI site at the two positions, digesting and religating the vector.

To examine FCA expression FCA promoter-GUS fusion constructs have been made. FCA promoter+exons 1–4 of FCA fused to the β-glucuronidase (GUS) gene have been constructed to monitor the splicing within intron 3. The entire FCA spliced cDNA ($\gamma_B$) with GUS fused in frame at the C-terminus has been made to monitor FCA protein localization within the cell.

EXAMPLE 10

Identification of FCA Homologues within the Arabidopsis Genome

Figure 7:
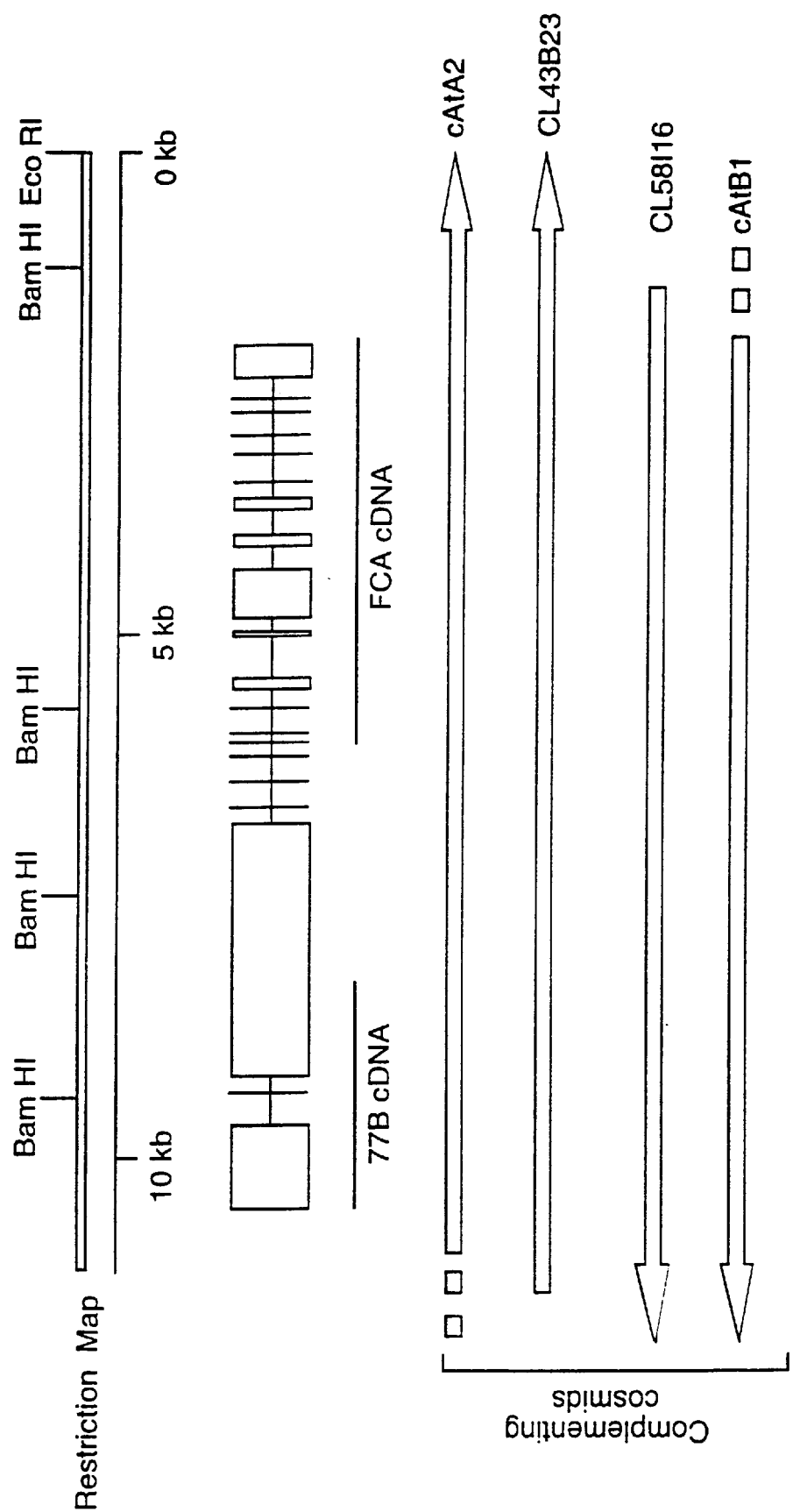
FIG. 7 shows the complexity and position of the FCA gene on the complementing cosmids.

A four genome equivalent Landsberg erecta cosmid library was screened using low stringency conditions (40° C. overnight, 1% SDS, 5×SSC, 0.5% milk powder) with the complete FCA genomic clone. The filters were washed 2×20 min at 45° C. in 2×SSC, 0.5% SDS. After exposure they were then rewashed 2×20 min, 50° C. in 2×SSC, 0.5% SDS. 61 cosmid clones were picked, plus two negative control cosmids. Five of these were additional FCA clones, leaving 56 putative FCA homologues. Minipreps were prepared from 10 ml o/n cultures of cosmids, digested with EcoRI, run on 0.8% gels with positive and negative controls on each gel and Southern blotted. The blots were hybridised separately to 77B and FCA cDNA (originally called 61A) (FIG. 7) using the conditions described above and then washed at 45° C. only.

Of the putative homologues:
(a)—2 cosmids hybridized only to 77B
(b)—11 cosmids hybridized only to 61A
(c)—31 cosmids hybridized to both cDNAs
(d)—13 cosmids difficult to score or showed no detectable hybridized (a) 2 cosmids appear not to be related
(b)
   49 C 22 and 67 I 3 share common EcoRI fragments
   18 G 16 and 7 L 2
(c)
   39 G 10, 46 H 15, 56 F 2 and 59 A 8 share common EcoRI fragments,
   39 G 10 and 56 F 2 share additional frag
   4 H 4 and 45 K 24 share two frags
   at least nine other pairs of cosmids may have at least one EcoRI fragment in common.

TABLE 2

SEQ ID NOS:13-25

| Primers | Sequence | bp start FIG. 3 |
| --- | --- | --- |
| cDNAII-BamHI | 5' CAGGATCCTTCATCATCTTCGATACTCG 3' | 25 |
| cDNAII-1 | 5' GTCCCTCAGATTCACGCTTC 3' | 228 |
| cDNAII-3'a | 5' CACTTTTCAAACACATC 3' | 1167 |
| cDNAII-3'b | 5' GTTCTCTGTACATTAACTC 3' | 1213 |
| BamX | 5' ATTGAGATTCTTACATACTG 3' | 2568 |
| RevEx1A | 5' TAAGACATGTCTGACAG 3' | 2838 |
| RevEx1B | 5' GTGATCTGATTGTGCAG 3' | 3030 |
| RevEx4 | 5' TAGACATCTTCCACATG 3' | 3145 |
| IanRT1 | 5' CAATGGCTGATTGCAACCTCTC 3' | 3320 |
| IanRT2 | 5' TCTTTGGCTCAGCAAACCG 3' | 3348 |
| Rev404 | 5' CAATGTGGCAGAAGATG 3' | 3673 |
| fca-3'a | 5' AGGCCATTGTTTGGCAGCTC 3' | 4941 |
| fca-3'b | 5' CCCAGCTAAGTTACTACTAG 3' | 5003 |

REFERENCES

Bancroft et al. (1988) Nucl. Acids Res. 16:7405–7418
Benfey et al. EMBO J 9: 1677–1684 (1990a).
Becker, et al. (1994) The Plant Journal 5, 299–307.
Bell et al. (1988) Cell 55, 1037–1046.
Benfey et al. EMBO J 9: 1685–1696 (1990b).
Bower et al. (1992) The Plant Journal 2, 409–416.
Burd et al. (1994) Science 265, 615–621.
Cao et al. (1992) Plant Cell Reports 11, 586–591.
Chandler et al. (1994) J. Exp. Bot. 45, 1279–1288.
Chang et al. (1988) Proc Natl Acad Sci USA 85:6856–6860
Christou et al. (1991) Bio/Technol. 9, 957–962.
Chung et al. (1994) Plant Mol. Biol. 26, 657–665.
Coulson et al. (1988) Nature 335:184–186
Dale et al. (1994) Murphy D. J. VCH, Weinheim, Germany.
Datta et al. (1990) Bio/Technol. 8, 736–740.
Dean et al. (1985) EMBO.J. 4, 3055–3061.
Dean et al. (1992) Plant Journal 2, 69–82.
English et al. (1996) The Plant Cell. 8, 179–188.
Frohman et al. (1988) Proc Natl Acad Sci USA 85, 8998–9002.
Gordon-Kamm et al. Plant Cell 2, 603–618.
Heard et al. (1989) Nucl Acids Res 17:5861
Jones et al. (1992) Transgenic Research 1, 285–297.
Koornneef et al. (1991) Mol Gen Genet 229, 57–66.
Koornneef et al. (1983) Heredity 74, 265–272.
Koornneef et al. (1994) The Plant J. 6, 911–919.
Koziel et al. (1993) Bio/Technol. 1, 194–200.
Lee et al. (1994) The Plant Cell 6, 75–83.
Lee et al. (1994) The Plant J. 6, 903–909.
Mandel et al. (1995) Nature 377, 522–524.
Medford, J. I. (1992) Plant Cell 4, 1029–1039.
Medford et al. (1991) Plant Cell 3, 359–370.
Mitzukama et al. (1992) Cell 71, 119–131.
Moloney et al. (1989) Plant Cell Reports 8, 238–242.
Napoli et al. (1990) The Plant Cell 2, 279–289.
Olszewski et al. (1988) Nucleic Acids Res. 16, 10765–10782.
Potrykus (1990) Bio/Technology 8, 535–542.
Putterill et al. (1993) Mol Gen. Genet. 239, 145–157.
Putterill et al. (1995) Cell 80, 847–857.
Radke et al. (1988) Theoretical and Applied Genetics 75, 685–694.
Rhodes et al. (1988) Science 240, 204–207.
Robinow et al. (1988) Science 242: 1570–1572.
Rothstein et al. (1987) Proc. Natl. Acad. Sci. USA 84, 8439–8443.
Sambrook et al. (1989). Molecular Cloning: A laboratory Manual. (Cold Spring Harbor, N.Y.: Cold Spring Harbor Laboratory).

Schmidt et al. (1992) Physical mapping of the *Arabidopsis thaliana* genome. Genome Analysis Vol.4 Strategies for physical mapping Cold Spring Harbour Laboratory Press 71–98

Schmidt et al. (1992) Aust J Plant Physiol 19: 341–351

Shimamoto et al. (1989) Nature 338, 2734–2736.

Smith et al. (1988) Nature 334, 724–726.

Somers et al. (1992) Bio/Technol. 10, 1589–1594.

Stiekema et al. (1988) Plant Molecular Biology 11, 255–269.

van der Krol et al. (1990) The Plant Cell 2, 291–299.

Vasil et al. (1992) Bio/Technol. 10, 667–674.

Valvekens et al. (1988). Proc. Natl. Acad. Sci. USA 87, 5536–5540.

Weigel et al. (1992) Cell 69, 843–859.

Weigel et al. (1995) Nature 377, 495–500.

Wester et al. (1994) Plant J. 5, 261–272.

Worley et al. (1995) Genome Research 5: 173–184

Zhang et al. (1992) The Plant Cell 4, 1575–1588.

What is claimed is:

1. An isolated nucleic acid comprising a nucleotide sequence coding for a polypeptide comprising the amino acid sequence shown in FIG. 2 (SEQ ID NO:3).

2. An isolated nucleic acid according to claim 1 wherein the coding sequence comprises a sequence shown as an exon in FIG. 1 (SEQ ID NO:1).

3. An isolated nucleic acid according to claim 2 wherein the coding sequence comprises the sequences shown as exons in FIG. 1 (SEQ ID NO:1).

4. An isolated nucleic acid according to claim 1 comprising an intron.

5. An isolated nucleic acid according to claim 4 comprising an intron as shown in FIG. 1 (SEQ ID NO:1).

6. An isolated nucleic acid according to claim 5 wherein said intron is intron 3 of FIG. 1 (SEQ ID NO:1).

7. An isolated nucleic acid according to claim 1 further comprising a regulatory sequence for expression of said polypeptide.

8. An isolated nucleic acid according to claim 7 comprising an inducible promoter.

9. An isolated nucleic acid comprising a nucleotide sequence complementary to a coding sequence of claim 1 or a fragment of said coding sequence, wherein said nucleic acid is DNA and said nucleotide sequence is under control of a regulatory sequence for anti-sense transcription.

10. An isolated nucleic acid according to claim 9 comprising an inducible promoter.

11. A nucleic acid vector suitable for transformation of a plant cell and comprising nucleic acid according to claim 1.

12. A host cell containing a nucleic acid according to claim 11, which nucleic acid is heterologous to the host cell.

13. A host cell according to claim 12 which is bacterial.

14. A host cell according to claim 12 which is a plant cell.

15. A plant cell according to claim 14 having said nucleic acid, which nucleic acid is heterologous to the host cell, within its genome.

16. A plant cell according to claim 15 having more than one said nucleic acid per haploid genome.

17. A plant part comprising a plant cell according to claim 16.

18. A plant comprising a plant cell according to claim 14.

19. A method of influencing timing of flowering of a plant, the method comprising causing or allowing expression of the polypeptide encoded by the heterologous nucleic acid according to claim 1 within cells of the plant, wherein said polypeptide influences timing of flowering of said plant.

20. A method of influencing timing of flowering of a plant, the method comprising causing or allowing transcription from the heterologous nucleic acid according to claim 1 within cells of the plant, wherein said transcription influences timing of flowering of said plant.

21. A method of influencing timing of flowering of a plant, the method comprising causing or allowing anti-sense transcription from the nucleic acid according to claim 9 within cells of the plant, wherein said anti-sense transcription influences timing of flowering of said plant.

22. An isolated nucleic acid comprising a nucleotide sequence coding for a polypeptide which on expression in a transgenic plant advances flowering time of the plant, wherein the nucleic acid positively hybridizes in a Southern hybridization experiment to an *Arabidopsis thaliana* FCA probe of which the coding strand nucleotide sequence is shown in SEQ ID NO:1, and said polypeptide comprises an RNA recognition motif encoded by a nucleic acid amplified by PCR using the following pair of degenerate primers:

```
Primer 1:  TTT GTG GGG AGG CTG AAC AAG C
           TTC GTA GGA TCA TTA AAT AAA C
           TTT GTT GGT AGT CTG AAC AAG C
           TTC GTC GGC AGC CTG AAC AAG C
Primer 2:  TAT TTG ACG AAG CCG CAG CCT
           TAC TTA ACA AAA CCA CAA CCT
           TAT TTT ACG AAT CCG CAT CCT
           TAT TTC ACG AAC CCG CAC CCT.
```

23. An isolated nucleic acid according to claim 22 that has the nucleotide sequence of intron 3 of FIG. 1 (SEQ ID NO:1) and all the exons of FIG. 1 (SEQ ID NO:1) except for the exon nucleotides indicated in FIG. 1 (SEQ ID NO:1) to be within the alternative intron splicing sites around intron 13.

24. An isolated nucleic acid according to claim 22 that has the nucleotide sequence of all the exons of FIG. 1 (SEQ ID NO:1) except for the exon nucleotides indicated in FIG. 1 (SEQ ID NO:1) to be within the alternative intron splicing sites around intron 13.

25. An isolated nucleic acid according to claim 22 that has the nucleotide sequence of all the exons of FIG. 1 (SEQ ID NO:1) including the exon nucleotides indicated in FIG. 1 (SEQ ID NO:1) to be within the alternative intron splicing sites around intron 13.

26. An isolated nucleic acid according to claim 22 which has the nucleotide sequence of an *Arabidopsis thaliana* FCA homologue of a species of Brassica.

27. An isolated nucleic acid according to claim 26 wherein said homologue comprises the amino acid sequence shown in FIG. 8b (SEQ ID NO:5).

28. An isolated nucleic acid according to claim 27 comprising the coding sequence shown in FIG. 8a (SEQ ID NO:4).

29. An isolated nucleic acid comprising a nucleotide sequence complementary to a coding sequence of claim 22 or a fragment of said coding sequence, wherein said nucleic acid is DNA and said nucleotide sequence is under control of a regulatory sequence for anti-sense transcription.

30. An isolated nucleic acid according to claim 29 comprising an inducible promoter.

31. A method of influencing timing of flowering of a plant, the method comprising causing or allowing anti-sense transcription from the nucleic acid according to claim 29 within cells of the plant, wherein said anti-sense transcription influences timing of flowering of said plant.

32. An isolated nucleic acid comprising a nucleotide sequence coding for a polypeptide which on expression in a transgenic plant delays flowering time of the plant, which delay is corrected by vernalization, wherein the nucleic acid positively hybridizes in a Southern hybridization experiment to an *Arabidopsis thaliana* FCA probe of which the coding strand nucleotide sequence is shown in SEQ ID NO:1, and said polypeptide comprises an RNA recognition motif encoded by nucleic acid amplified by PCR using the following pair of degenerate primers:

```
Primer 1:  TTT GTG GGG AGG CTG AAC AAG C
           TTC GTA GGA TCA TTA AAT AAA C
           TTT GTT GGT AGT CTG AAC AAG C
           TTC GTC GGC AGC CTG AAC AAG C
Primer 2:  TAT TTG ACG AAG CCG CAG CCT
           TAC TTA ACA AAA CCA CAA CCT
           TAT TTT ACG AAT CCG CAT CCT
           TAT TTC ACG AAC CCG CAC CCT.
```

33. An isolated nucleic acid according to claim 22 or claim 32 comprising an intron.

34. An isolated nucleic acid according to claim 33 comprising an intron as shown in FIG. 1 (SEQ ID NO:1).

35. An isolated nucleic acid according to claim 34 wherein said intron is intron 3 of FIG. 1 (SEQ ID NO:1).

36. An isolated nucleic acid according to claim 35 comprising the nucleotide sequence of FIG. 3 (SEQ ID NO:2).

37. An isolated nucleic acid according to claim 22 or claim 32 further comprising a regulatory sequence for expression of said polypeptide.

38. An isolated nucleic acid according to claim 37 comprising an inducible promoter.

39. A nucleic acid vector suitable for transformation of a plant cell and comprising nucleic acid according to claim 22 or claim 32.

40. A host cell containing a nucleic acid according to claim 22 or claim 32, which nucleic acid is heterologous to the host cell.

41. A host cell according to claim 40 which is bacterial.

42. A host cell according to claim 40 which is a plant cell.

43. A plant cell according to claim 42 having said nucleic acid, which nucleic acid is heterologous to the host cell, within its genome.

44. A plant cell according to claim 43 having more than one said nucleic acid per haploid genome.

45. A plant comprising a plant cell according to claim 42.

46. A plant part comprising a plant cell according to claim 42.

47. A method of influencing timing of flowering of a plant, the method comprising causing or allowing expression of the polypeptide encoded by the heterologous nucleic acid according to claim 22 or claim 32 within cells of the plant, wherein said polypeptide influences timing of flowering of said plant.

48. A method of influencing timing of flowering of a plant, the method comprising causing or allowing transcription from the heterologous nucleic acid according to claim 22 or claim 44 within cells of the plant, wherein said transcription influences timing of flowering of said plant.

49. A pair of degenerate oligonucleotide primers with the following sequences:

```
Primer 1: TTT GTG GGG AGG CTG AAC AAG C
          TTC GTA GGA TCA TTA AAT AAA C
          TTT GTT GGT AGT CTG AAC AAG C
          TTC GTC GGC AGC CTG AAC AAG C
Primer 2: TAT TTG ACG AAG CCG CAG CCT
          TAC TTA ACA AAA CCA CAA CCT
          TAT TTT ACG AAT CCG CAT CCT
          TAT TTC ACG AAC CCG CAC CCT.
```

50. A method of amplifying a FCA homologue from a species of plant other than *Arabidopsis thaliana*, the method comprising generating amplification products by subjecting nucleic acid of said species to PCR employing a pair of degenerate oligonucleotide primers with the following sequences:

```
Primer 1: TTT GTG GGG AGG CTG AAC AAG C
          TTC GTA GGA TCA TTA AAT AAA C
          TTT GTT GGT AGT CTG AAC AAG C
          TTC GTC GGC AGC CTG AAC AAG C
Primer 2: TAT TTG ACG AAG CCG CAG CCT
          TAC TTA ACA AAA CCA CAA CCT
          TAT TTT ACG AAT CCG CAT CCT
          TAT TTC ACG AAC CCG CAC CCT
``` and analyzing said amplification products to identify said FCA homologue.

51. A method according to claim 50 further comprising isolating a nucleic acid that has been amplified employing said primers.

* * * * *

SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
      (A) LENGTH: 9763 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Arabidopsis thaliana
      (B) STRAIN: Columbia (xi) SEQUENCE DESCRIPTION: SEQ ID NO: 1:

```
GATCTAGGTG AAATTAATCT GAAGTTTAGA AATAGATTTT CTTGGAACTT CGGAGAAAAT      60

ATGCTTCACT CAACTTTTTT TTGGTGCTAT ATGAACAAAG ATAATGGTCA TATGAATGTA     120

AACGTGTTTT GGGATGATGT TATCTTGTTC CATAGATGCG GTTGGAAGAA TTGCATTTGG     180

ACTGCAAAAA CTGATGGCCT TTATCTTTGG AATTCAGCGA GCGGTGAAGA TGTATTGTCA     240

AGAAAATGGG AAGTTGGATG GTGAAGCCAT ATTTTTGCTT TTGGGTAATT TTTTAGTACA     300

TGTATCTTGT TGTTTTTGGC AAAAAAAAAA TTGAAATAAT AAAAAACATT TGTTTTAACT     360

TTCTCTCTTA TTTTGTGTAT TTTTCATCAA TGATAGATTT TTTGTTTTAG TTCTTTATTT     420

ATAGGTCATT TAATTATTAG ATTAATTTCC TGAGATAATA AGATCATAGA TTAAATAACA     480

ATATTGTGTT TGTGATATAT AGAGATTACA TTTTACACTT ATATATAGTG GTAAGATTTC     540

TTTTTGCTTT CAAACCATTA AAAACCTGTT AAACGATTAA CTTGACTCAA GACAAAGCCA     600

TTGATTATTG ACTCATGAAT CTAGTGACTC ATGATGAAGG AGACGAACAG TAAATATTCA     660

TTTGATTATT TTAGGTAAAA GGTAGTTCAG ACCTAGTCAT ATATCCTCTA AATTCATATA     720

GTGATGCAAG TATTTTGCAT TACTTAGAAC TTTATATTAT TGATCACCCA ACACATGATT     780

TAATAAACGC CATGAAATGC ATGTACTATA TCAAAATGTT TCTGAAGCAT ATAGTTGACA     840

TGAGAATTTT GGATTGGACT TAAGAATGTG AGAGTTACCT GAAATGTCAA TTTTTTTCCC     900

TTTGTTAACG AAAACTCATT GGAACAATTG TATCCCCCTT TTGGCAGTAT ATAAATATAT     960

TGATGGCCCA AGTAGCTGTA TTTTCCGTTA TCAGCCAAGA CTCAATAAAG TCTACCGGTC    1020

CAAATTTCAA CTGAATCACC GGTCCAACCA CTATTACCGT AACTAGACCG CTTTTTCTTT    1080

TTTACATTCG GACAAAAAAA TCAAAATTTC GAGCAACTAA ATTGATCTCA TCTTCAATCA    1140
```

```
AATTCATCAT CTTCGATACT CGTTTCTTCT CTCTTTGGTT TCATACAGAT CCCAAATTTC    1200

TAGGGCTCCT AGTCCTTTGA TTTCTTCGAC TGGAATCGCA ATTCCCCACT ACGTCAAGCT    1260

GGACAGACAC CGAAGGGATC GCCATGAGAG TGGCGGCTAC GAGGATTCCT ACCATAACCA    1320

CCGAGCCCAT CCCAGAGGTC CATCTCGTCC CTCAGATTCA CGCTTCGAAG AGGATGATGA    1380

TGATTTTCGC CGCCACCGTC GTCGTCGTGG AAGCAGCCCT AGCAATTATC GAATTGGAAT    1440

TGGGGGCGGA GGAGGAGGTA ATGGTGGTCG ACGCTGGGAA GATGACACTC CTAAGGATTT    1500

TGATGGTCCC GGAGATGGAG GTTTCCGGCA GATGAATGGT CCCCCAGATA GAGTAGATTT    1560

TAAGCCTATG GGTCCTCACC ATGGTGGAAG TTTTCGGCCT ATGGGGTTTG CCTACGATGA    1620

TGGTTTTCGT CCAATGGGTC CTAACGGTGG TGTGGGAGGA GAAGGGACAC GGTCAATTGT    1680

TGGAGCTCGG TATAACTATC CCGCGAAGTA TCCTCCTTCA GAGAGTCCAG ACAGGAGGAG    1740

ATTTATCGGT AAAGCAATGG AGTCTGATTA TTCTGTAAGA CCGACTACAC CGCCGGTCCA    1800

GCAGCCTCTT TCCGGTCAGA AAAGAGGGTA TCCTATCTCA GACCATGGCA GCTTTACTGG    1860

AACTGGTAAG CATGAGTTCA CTCTTCTTTC TTCTATGTAT ATTTATTCTT GTAGTCTGTT    1920

AAGGTTCCTG AGTGTCTCTT ATTTTTGTGG GAATCAATGA TTAGAGTATT GAAAGGTAGT    1980

ATGGTTGTTA TGTTACTGTA TTGTTGAAGG TTTTTCATGG GATCGACTCT AGAGGATCCT    2040

TTCGATTTTC CCATGTATGT GATAATCAAA ACTATATGCC ATCTTCATGT GTATCCTTAT    2100

CTGGTTAATT TGATTTGCAG ATGTCTCTGA TCGTAGCAGT ACAGTCAAGC TTTTTGTTGG    2160

ATCTGTACCA AGGACAGCTA CAGAAGAAGA AGTGAGTTAA TCTTGGAAAT CATTGTTATC    2220

TATATACTCA TTACTGAGAA CCTTTTCTAA ATTTTTTCTG TTGGTTTTCA TATTGTAGAT    2280

CCGTCCCTAT TTCGAACAGC ATGGAAATGT TCTGGAGGTT GCTCTGATCA AGGACAAGAG    2340

AACTGGACAG CAGCAAGGTA TGTCAATCTC CATTTTATTA GGAAATAGTC GTGAATTATA    2400

CTTTTTAAAA TTTCAGGTCT CCCTGAAAAG GCTGATGGGA AGCAACCCCA GTCTCATCAT    2460

TGGCCTCCAA TTGTTTGCAA CAATTTTCGG GCTTATTGCT TATGCTTGCC AGCGTCTTAT    2520

CTGTGTTCGA TTCTGTCACA GAAGAAGGCT ACCTGTGCTA AGAAAGGGTT TATGTACTTA    2580

TGTTGGGCAA ATAGATTTCG CTACTTGTGT GTATTCTAGA ACTTTAGATG TGTTTGAAAA    2640

GTGTAGAATT TATTGAGGGT GTTTTAGAGT TGGAGTTAAT GTACAGAGAA CTGAATTTTG    2700

CTGTTGCCTT TATAGTGGGA ATTGGTTATA AGAACATCGC TATTTTCCTC TCCTATTGAA    2760

ATTCATTTTC TTTACTCTTC CTCTAGATGG ATTGAAGATG TTGTGTATGG TCTTGACAGG    2820

ATGAATGTAT TTTTTTAAGT TGGTAGTTTG ATAAGGACAT GAGGTTCAAA AGATGGTTTC    2880

TTGATTTGCC ACTCCTGCTG GTCAAAGATT TGGCCGTCTT TCTAATTTTA TCATGTTGGA    2940

GGTTTGGCGT CTTCATTTTC TTTCATATCA ATTTATGGGT GTGCTGTCTA TTGGTTAATG    3000

ATGGCATTCC TTTTACCTTT TTGGATGAGT GATGCTGGAA TGAATGCGTT TCTCCTTTTC    3060

TTTTGTTGAT GGCCTGAGGA ACTATGATGG CTATATTTCT TTCCACTCTC TTTGAATGGC    3120

CTGAAATGTG TGCTTTCTGT ATGGTCGTCC CTCTCAATTT CTTGGATGGC TTGTGATGTG    3180

ATATACCATC TCTCGTCATA GGTGAATGAA TGATTTGTTT AGTAGTTCTT ATGTATGTAT    3240

TTTGTATGTT CCCACGTCTC TATTCCTTGG ATGGCTTGTG ATGTGATATA CCATCTCTCG    3300

TCATAGATGA ATGAATATTT TGTTGAGTAG CTCTTATGTC TGTATGGTGG CCCTTGCAGT    3360

GCTGATCGAT ATTTATGTGG AAGAAATGTT TGATGATAGA TTTTTTTTGT ATGCTCCCTT    3420

TTCGCTAATC AAGCCTTTGT GCTTGCAAGG TGCAACTGTT ATTTTATTAT TGAATTTCCT    3480
```

```
GTTCTACTAC TCCATTTAGT TCTGTCTCTA TTTTGTCAGT GTGAAGAAAT ACTAGACGAT    3540

GAATGGTGTG TTTGTACGTG CATAGTTATT TATAAATTCT TGACTTTCCA AGAAGTTATT    3600

ATTTCTATAA CTGCTACACC TTTGTGGATG GCAGAACAAA TGCATCTGAT TGTGGTGACA    3660

TAAACACTTT TGATCGCGGT TGAATGTACT AGATTCCATA CAACTCTTTC TTCAGCCTTG    3720

TGAAATATTA TTATGTTAGG TGGTGCAAAC ATATGGAAGG AACCTGATTG TTTTAGTTTC    3780

TTAGAATAGT TTCTGATGTT AATACAGCAT GTTGACTTCA CTCTCTTGCC CTTGATCAAT    3840

CAGCATCAGG CAGGGGCCTA ATTATGTATT ACATGAAGCA ATCGTATTCT TTTCTGAATT    3900

AGATTTTTTT CCAATGAGTT ATCTTGCCCA TAACTGTAGT TCTTTATTTG AAGTCTTCAA    3960

ATGCTTGATG TATGGTGACG AAAATGTGTA TATGTTTTGG TTTTGATTAT CCGCTACTCA    4020

TCAATTATTG AGATTCTTAC ATACTGAATC CGTTACTTTG GACCTATAGT TATGTTTTAT    4080

GTTGCTAATT AACTTGTACA TGTTTCTAGA TTTTCTTTCA AATGGATCCT GCTTGGACAA    4140

ATGCAGCCAC CCTTTGTCTG AAAGGCCCTC TTGTAGATAT GTTATCTGCA GATACTGACT    4200

GTGTTCAATT TTTTAATATT TGTTTTTGCC ATATTCTCCA TTTGAAGACA TTAATTTATT    4260

CTCTCCAACA ACTTTACATC AATATTTAAG TGGAGGCTGT CAGACATGTC TTATGATTTT    4320

CCTACTGAAC TTATGTGCTT TGAGTAGTAC ATCTTGTTAC TAGTACAATT TGATGGTAGA    4380

AGGAAAAGTT GAACCCTGAA ACAGATAGCT TAAGTATCAG TCTTTAATGC AGGCTGTTGT    4440

TTTGTAAAAT ATGCAACTTC GAAAGATGCG GATAGAGCCA TCAGAGCACT GCACAATCAG    4500

ATCACTCTTC CTGGGGTAAT TACCCTGAGG CTTTCTCTTA TCAAGAACAG GAAACTATAG    4560

GTTGTTTCAC CTTTTATAAT TTTGTTGATT CCCAGGGAAC TGGTCCTGTT CAAGTTCGAT    4620

ATGCTGACGG GGAGAGAGAA CGCATAGGTA ATCAACTTCC ACACAGAGTA TCTAATGTGG    4680

CTGTCATTGT CTAGTGTTCA TAGCCAAGAC CATACGCTGC ATAAGTTCAG ATTACAAAAA    4740

TTAAGAAAAT GTGGGAAATG ATATGAACTT TATGGATGTT GATCCTTTTC TTTCCCTGTT    4800

TTCTTTGCCT TACTATCAAG TGATATAGTT CTCTTCTTCT GAAGGCACCC TAGAGTTTAA    4860

GCTTTTTGTT GGTTCACTAA ACAAGCAAGC CACTGAAAAA GAAGTTGAGG AGGTATGTTT    4920

CGTATCTTAC TTTTTGAAGT TGTTACTTAT GTCAGATTAA CGGAACAGGG AAGAGTTCTA    4980

AACTTGGATA TTATTGTGTC CCCTGTTACC TGAGTTGATA ATTTTAAATG ACTCTTTGAT    5040

AAATTTTGTT AGTCTTACCA AAGGGTGAGT GTCTAGAAAA TCTGTGTCAA TAATGCAAGC    5100

GCTTGGACAT TCTACTTACT GTGTAATCTC TTCTTCCAAT TGATCCAACT GTTTGACTGT    5160

CATAATAGAT AAAATTAATA AATGTGAACG GCTACCTTCC CAGTTCAACT TATGTGTTTC    5220

AATTTCTCAT GTAATCTTTT AACAAACTGT TTTATTGTTA TTGCTTTAAC AGATCTTTTT    5280

ACAATTTGGT CATGTGGAAG ATGTCTATCT CATGCGGGAT GAATATAGAC AGAGTCGTGG    5340

TATGTTTTGT AATTTGTACT AGATTCTATA AATTATTTGT TGTGTGATGA TGTTGAGATG    5400

GTGAAACTGT GTTTTCACT TTGTAGGATG TGGGTTTGTT AAATATTCAA GCAAAGAGAC    5460

GGCAATGGCA GCTATCGATG GTCTCAACGG AACTTATACC ATGAGAGTAA GCTGTGAATC    5520

ACATAAGTAT CTCAGTTTCT CTCATTATCA CCCTTTGGAC CTGTTTTGTT TACTGGCCTC    5580

TATCCTTTCC CCAGGGTTGC AATCAGCCAT TGATTGTTCG GTTGCTGAG CCAAAGAGGC    5640

CTAAACCTGG CGAGTCAAGG TAATGCCTTG GGTACTATAT TTTGATTAAT CCTAATACTC    5700

TTATCAAGTA AATTGTATAT ACCTTCATTC TTTGTTCTGT CTGAGTTATA TTTGTGGAGA    5760

ATCTTTTGGA CATGGTGGAG AGTTGGGAAC CCTGTTCCTT CTCCAGTTAT TACTGGAATG    5820

TGAAGCATTG CTTTCTAGAT ATCCTTAAGT AGTTTCTGTT TCCAGGGAAA TGGCACCTCC    5880
```

```
TGTTGGACTT GGTTCAGGGC CTCGTTTTCA AGCTTCAGGA CCAAGGTAAC TGGTGTGAAA    5940

GGAGATCATG ATTATGCTCA TTAGGTAATT ATATATGTTG ACTTACCCCG GTCTCCTCAT    6000

CTCTATTTGT TAGGCCTACC TCTAACTTTG GTGACTCTAG TGGGGATGTA AGCCACACAA    6060

ATCCTTGGCG TCCAGCTACT TCACGAAACG TAGGCCCACC TAGTAACACT GGGATCCGTG    6120

GTGCCGGTAG TGACTTTCCC CCTAAACCAG GTCAAGCAAC ATTGCCTTCA AATCAGGTGA    6180

GAACAGGTTG ATGATCATGT ATATCATCTT AAATCTGCAC ATTCATATAA GTAAGCGCAT    6240

AGAGTTTGCA TGTATTGTGC GAGACAAATA AAAAGAAAGT ACTTCATATA CTGCACACAT    6300

GGGCTTATGA CAGGTGAAAA GAAGCATGAA GTTCTGACCT TTCAACTTTT CATATAATGC    6360

AACAAACACG ATGTGTGTTG CTCAAATGAT ATGGCCTTAA TTTGCAGTTT GTCAGTTACT    6420

GAGGCAATTT TTTTTTTGAA TAATTTCTAG CCCTGATGTG AGCTTTTTTA AATGTAACAT    6480

TCTATATTGT TAGGGTGGCC CGTTAGGTGG TTATGGTGTT CCTCCCCTTA ACCCTCTCCC    6540

AGTCCCTGGA GTTTCATCTT CTGCCACATT GCAACAGGTA CTTTAGCTAT ATTTTTCCAA    6600

TTAAGCAAAT CTGAAAATGT TGTGATGATT AACTTGGATT TTCAATTGTT TCTATTCCAT    6660

AGCAAAATCG GGCAGCTGGC CAGCATATAA CACCATTAAA AAAACCTCTT CACAGTCCAC    6720

AGGGTCTCCC TCTCCCCCTC CGTCCGCAAA CTAATTTCCC TGGGGCCCAG GCACCCTTGC    6780

AGAATCCTTA TGCTTATAGC AGCCAGTTGC CTACCTCTCA GCTGCCACCA CAGCAAAACA    6840

TCAGTCGTGC AACTGCTCCT CAAACTCCTT TGAACATTAA TCTACGGCCA ACAACTGTGT    6900

CTTCTGCAAC TGTTCAATTT CCCCCTCGTT CCCAGCAGCA ACCGCTACAA AAGATGCAAC    6960

ATCCTCCTTC TGAGCTAGCT CAGCTCTTGT CGCAGCAAAC TCAGAGTCTA CAAGCAACAT    7020

TCCAATCGTC TCAGCAAGCA ATTTCTCAGC TGCAGCAGCA GGTGCAGTCT ATGCAGCAAC    7080

CAAACCAAAA TTTACCACTC TCACAGAATG GCCGAGCTGG TAAACAACAG GTATGAATAT    7140

AGTCTCTCAG TTGCATCTGC CCAGACGGGT TCTTCAGCTG CTATTGTGTT GTTTTAACTT    7200

AAAATTATTT CCTGATAGAC ATCCCGTTTT TTATCCTTCA TGTGTTTTAG TATTCTCCCC    7260

TTTTCTAATG TTCCTCTCGG CTGCTTCTTT ATCAGTGGGC TGGATCTGCA ATTCCAAGAG    7320

TGGCTAGCAC CACTGGTTCG ACACCAGTGA GCTATGTGCA AACAGCTGCA CCTGCAGTAA    7380

GTCAGAGCGT AGGTTCTGTC AAATGTACCT GGACCGAGCA TACCTCGCCT GATGGATTTA    7440

AATATTATTA CAATGGTCTA ACGGGTGAAA GCAAGGTGAG AAACGTGGTT CCTCTTTAAT    7500

ATATTTCCTT GTGAGTTTCA GGAGTATTCC TCCTGGTTTA TTGTGCTATT GATAATCCTT    7560

ACACATGTAT ATTTTATATT TGAAGTCCTT CAGTACGTGC CATATTATGT ATATAATTCA    7620

CTTTTGCAGT GGGAAAAACC TGAGGAAATG ATAGTGTTCG AACGAGAGCA ACAGAAACAG    7680

CAACAACATC AAGAGAAGCC AACTATACAG CAGTCCCAGA CCCAATTACA GCCGTTGCAG    7740

CAACAACCAC AACAAGTTCA GCAGCAATAT CAGGGCCAGC AATTACAGCA GCCGTTTTAT    7800

TCTTCACTGG TTGGTTTCGT TTTCATGCTG GTTACATTCA AATATTTTTG TCACATGGTT    7860

TCTAATTTGC ATATTTACTC TTGTTCATTT GGAGTTGCAG TATCCAACTC CAGGGGCCAG    7920

CCATAATACT CAGGTGTATA TCTGTTTAAT CTGTTTACTT ATTTTTCATT TCAAGATTTG    7980

ATTCTTGATA TGCTAATCTT GTGGTAGAAG GAGATTGACC ACCTTAAAGT AAAATTCAGT    8040

AGCCATGGTT TTGCCAGCAT TTTGAAATAC AGATAACAAA TCTCTAACGT GAATGCCTAT    8100

TTTCCTTTCT AAAATGCAGT ATCCATCATT GCCAGTAGGT CAAAATAGCC AGGTACATAT    8160

CTGAATCTGT GGACTTATTT TTCATTGAAC TGATTGATTC TCAGTTACAA CATTGACTTC    8220
```

```
CTCTGATGCG TAGTTTTTGT AACATATCAG AATAACAAAA ACTTCATCTG ATTCGTATAT    8280

TCTCTGGTTG AAAATCTTTT TTTCTTTTCT GGAAAATGCA GTTTCCTATG TCAGGAATTG    8340

GTCAGAATGC TCAGGTATAT ATCTCATTTT GTATTAACAA TTTCCCATAC CTTCTGTACC    8400

TTTGAATTTA ATCACAGAAC ATAATGAGTT CTTGGATTTA ATGTCATTTT AAAAAGAAAC    8460

ATCAGTGATA TGACTTCCTT CCTTGGTTAA AAATGGTTTA GGCAGAGCTT ATTTTCTATT    8520

CTGTTTGGAT TGTCTAGGAT TATGCTCGGA CACATATACC CGTGGGAGCT GCTTCAATGA    8580

ATGATATATC AAGAACTCCA CAGGTAGTTA TGGTTTTTAT CAGTGATTCA GAACTTCTCT    8640

CTGTTCATAA TTCGTCCTTT GGTATTCAGA TGTTCTTTTT CGTTGAAACC GTTTTTTTCC    8700

TTAATTCTCT TTACAATCAT ATCTCTTTTT CCCAGAGCCG TCAATCTCCC AAGAACTCA     8760

TGTGGAAGAA TAAAGCTTGA GGTTCATATC TACCCTTTCT CTCCTCTCTC TTGTATTTTC    8820

TCCATACCGA AACACATTCC AATGTATGTG GTTTCTTTAG TTGAAGTTAC CTCTGTGTTG    8880

ATCGATACTC TACTTCAGGT ACATGAGACG AGGAGCTAAA CTATCTCAGT AGCTAGATAG    8940

AAATTTCTGG AACTAATTAG TCAAGGAGAG GAAAAGCAGC AATGGTAGTG TCCTTAGTCT    9000

CTGATTTTTT TAGTTAACCC CTTCAGTTAT AATAGATAGG CGATCGTAGA CCATCTGCAT    9060

TCTATCTTTT CTCTAATCAG ATATCTCCTC CTTTTCCATT TTAAGAGCTG CCAAACAATG    9120

GCCTGTTGTA ACATAGCTAG CGCAAGTTAT GTCTCATGTT GTGTTACTAG TAGTAACTTA    9180

GCTGGGTAAA CCAAACTTTG ATCCAGATTA GGAGTCATAT ATAATTATAT AAATAGAATA    9240

TGTACATTCA TAGATAGCTC ATCACTTATA ATGAGACTAG ATCTTAGCAA AATCCAACTC    9300

TAATTGTCAT TTTCAGAGAT CTATCAATTT GTAGTTTCCT GATCTTCATA TATGTGTTCG    9360

CTCTTCTAAT GATTACGTAA AATCAGAGTC CTACGTAGGT GGACTTCTTT AATTTTTATA    9420

TAGATAATTA GATATCATTC AATAAGTCGG GCTTTTATTT TTAGTTAATC ATTCTACAAT    9480

TCTTCCTAAT CTCGCTATTA CTACCACCGG GTATCCCTCC CATTTTAACC ATAGCGTTCT    9540

TAAAATCCTC AAAGAAAACC GACTGATCTG TTGCGTAGGT CTCAACAATC GCCCTTGTCC    9600

CTGGGTCTTG AACCGCTAAA GCCTGGTCTG ATGGAAGCAA TCCCTCACCC GAGAGGAGGT    9660

TTACATAGTA CTGGTTGTCA AATGTTGATG GAGTCACCAA GTCAAGCTGA GTGATACCTA    9720

CACTGGGCCC AACAGTCGAG CATAACTGTT GCAGTGACTC GAG                     9763
```

(2) INFORMATION FOR SEQ ID NO: 2:

(i) SEQUENCE CHARACTERISTICS:
        (A) LENGTH: 5113 base pairs
        (B) TYPE: nucleic acid
        (C) STRANDEDNESS: double
        (D) TOPOLOGY: linear (ii) MOLECULE TYPE: cDNA (iii) HYPOTHETICAL: YES (iv) ANTI-SENSE: NO (vi) ORIGINAL SOURCE:
        (A) ORGANISM: Arabidopsis thaliana
        (B) STRAIN: Columbia (xi) SEQUENCE DESCRIPTION: SEQ ID NO: 2:

```
AAATTGATCT CATCTTCAAT CAAATTCATC ATCTTCGATA CTCGTTTCTT CTCTCTTTGG     60

TTTCATACAG ATCCCAAATT TCTAGGGCTC CTAGTCCTTT GATTTCTTCG ACTGGAATCG    120

CAATTCCCCA CTACGTCAAG CTGGACAGAC ACCGAAGGGA TCGCCATGAG AGTGGCGGCT    180
```

-continued

```
ACGAGGATTC CTACCATAAC CACCGAGCCC ATCCCAGAGG TCCATCTCGT CCCTCAGATT    240

CACGCTTCGA AGAGGATGAT GATGATTTTC GCCGCCACCG TCGTCGTCGT GGAAGCAGCC    300

CTAGCAATTA TCGAATTGGA ATTGGGGGCG GAGGAGGAGG TAATGGTGGT CGACGCTGGG    360

AAGATGACAC TCCTAAGGAT TTTGATGGTC CCGGAGATGG AGGTTTCCGG CAGATGAATG    420

GTCCCCCAGA TAGAGTAGAT TTTAAGCCTA TGGGTCCTCA CCATGGTGGA AGTTTTCGGC    480

CTATGGGGTT TGCCTACGAT GATGGTTTTC GTCCAATGGG TCCTAACGGT GGTGTGGGAG    540

GAGAAGGGAC ACGGTCAATT GTTGGAGCTC GGTATAACTA TCCCGCGAAG TATCCTCCTT    600

CAGAGAGTCC AGACAGGAGG AGATTTATCG GTAAAGCAAT GGAGTCTGAT TATTCTGTAA    660

GACCGACTAC ACCGCCGGTC CAGCAGCCTC TTTCCGGTCA GAAAAGAGGG TATCCTATCT    720

CAGACCATGG CAGCTTTACT GGAACTGATG TCTCTGATCG TAGCAGTACA GTCAAGCTTT    780

TTGTTGGATC TGTACCAAGG ACAGCTACAG AAGAAGAAAT CCGTCCCTAT TTCGAACAGC    840

ATGGAAATGT TCTGGAGGTT GCTCTGATCA AGGACAAGAG AACTGGACAG CAGCAAGGTA    900

TGTCAATCTC CATTTTATTA GGAAATAGTC GTGAATTATA CTTTTTAAAA TTTCAGGTCT    960

CCCTGAAAAG GCTGATGGGA AGCAACCCCA GTCTCATCAT TGGCCTCCAA TTGTTTGCAA   1020

CAATTTTCGG GCTTATTGCT TATGCTTGCC AGCGTCTTAT CTGTGTTCGA TTCTGTCACA   1080

GAAGAAGGCT ACCTGTGCTA AGAAAGGGTT TATGTACTTA TGTTGGGCAA ATAGATTTCG   1140

CTACTTGTGT GTATTCTAGA ACTTTAGATG TGTTTGAAAA GTGTAGAATT TATTGAGGGT   1200

GTTTTAGAGT TGGAGTTAAT GTACAGAGAA CTGAATTTTG CTGTTGCCTT TATAGTGGGA   1260

ATTGGTTATA AGAACATCGC TATTTTCCTC TCCCTATTGA AATTCATTTT CTTTACTCTT   1320

CCTCTAGATG GATTGAAGAT GTTGTGTATG GTCTTGACAG GATGAATGTA TTTTTTTAAG   1380

TTGGTAGTTT GATAAGGACA TGAGGTTCAA AAGATGGTTT CTTGATTTGC CACTCCTGCT   1440

GGTCAAAGAT TTGGCCGTCT TTCTAATTTT ATCATGTTGG AGGTTTGGCG TCTTCATTTT   1500

CTTTCATATC AATTTATGGG TGTGCTGTCT ATTGGTTAAT GATGGCATTC CTTTTACCTT   1560

TTTGGATGAG TGATGCTGGA ATGAATGCGT TTCTCCTTTT CTTTTGTTGA TGGCCTGAGG   1620

AACTATGATG GCTATATTTC TTTCCACTCT CTTTGAATGG CCTGAAATGT GTGCTTTCTG   1680

TATGGTCGTC CCTCTCAATT TCTTGGATGG CTTGTGATGT GATATACCAT CTCTCGTCAT   1740

AGGTGAATGA ATGATTTGTT TAGTAGTTCT TATGTATGTA TTTTGTATGT TCCCACGTCT   1800

CTATTCCTTG GATGGCTTGT GATGTGATAT ACCATCTCTC GTCATAGATG AATGAATATT   1860

TTGTTGAGTA GCTCTTATGT CTGTATGGTG GCCCTTGCAG TGCTGATCGA TATTTATGTG   1920

GAAGAAATGT TGATGATAG ATTTTTTTTG TATGCTCCCT TTTCGCTAAT CAAGCCTTTG   1980

TGCTTGCAAG GTGCAACTGT TATTTTATTA TTGAATTTCC TGTTCTACTA CTCCATTTAG   2040

TTCTGTCTCT ATTTTGTCAG TGTGAAGAAA TACTAGACGA TGAATGGTGT GTTTGTACGT   2100

GCATAGTTAT TTATAAATTC TTGACTTTCC AAGAAGTTAT TATTTCTATA ACTGCTACAC   2160

CTTTGTGGAT GGCAGAACAA ATGCATCTGA TTGTGGTGAC ATAAACACTT TGATCGCGG    2220

TTGAATGTAC TAGATTCCAT ACAACTCTTT CTTCAGCCTT GTGAAATATT ATTATGTTAG   2280

GTGGTGCAAA CATATGGAAG GAACCTGATT GTTTTAGTTT CTTAGAATAG TTTCTGATGT   2340

TAATACAGCA TGTTGACTTC ACTCTCTTGC CCTTGATCAA TCAGCATCAG GCAGGGCCT    2400

AATTATGTAT TACATGAAGC AATCGTATTC TTTTCTGAAT TAGATTTTTT TCCAATGAGT   2460

TATCTTGCCC ATAACTGTAG TTCTTTATTT GAAGTCTTCA AATGCTTGAT GTATGGTGAC   2520

GAAAATGTGT ATATGTTTTG GTTTTGATTA TCCGCTACTC ATCAATTATT GAGATTCTTA   2580
```

-continued

```
CATACTGAAT CCGTTACTTT GGACCTATAG TTATGTTTTA TGTTGCTAAT TAACTTGTAC    2640

ATGTTTCTAG ATTTTCTTTC AAATGGATCC TGCTTGGACA AATGCAGCCA CCCTTTGTCT    2700

GAAAGGCCCT CTTGTAGATA TGTTATCTGC AGATACTGAC TGTGTTCAAT TTTTTAATAT    2760

TTGTTTTTGC CATATTCTCC ATTTGAAGAC ATTAATTTAT TCTCTCCAAC AACTTTACAT    2820

CAATATTTAA GTGGAGGCTG TCAGACATGT CTTATGATTT TCCTACTGAA CTTATGTGCT    2880

TTGAGTAGTA CATCTTGTTA CTAGTACAAT TTGATGGTAG AAGGAAAAGT TGAACCCTGA    2940

AACAGATAGC TTAAGTATCA GTCTTTAATG CAGGCTGTTG TTTTGTAAAA TATGCAACTT    3000

CGAAAGATGC GGATAGAGCC ATCAGAGCAC TGCACAATCA GATCACTCTT CCTGGGGGAA    3060

CTGGTCCTGT TCAAGTTCGA TATGCTGACG GGAGAGAGA ACGCATAGGC ACCCTAGAGT    3120

TTAAGCTTTT TGTTGGTTCA CTAAACAAGC AAGCCACTGA AAAGAAGTT GAGGAGATCT    3180

TTTTACAATT TGGTCATGTG GAAGATGTCT ATCTCATGCG GGATGAATAT AGACAGAGTC    3240

GTGGATGTGG GTTTGTTAAA TATTCAAGCA AAGAGACGGC AATGGCAGCT ATCGATGGTC    3300

TCAACGGAAC TTATACCATG AGAGGTTGCA ATCAGCCATT GATTGTTCGG TTTGCTGAGC    3360

CAAAGAGGCC TAAACCTGGC GAGTCAAGGG ACATGGCACC TCCTGTTGGA CTTGGTTCAG    3420

GGCCTCGTTT TCAAGCTTCA GGACCAAGGC CTACCTCTAA CTTTGGTGAC TCTAGTGGGG    3480

ATGTAAGCCA CACAAATCCT TGGCGTCCAG CTACTTCACG AAACGTAGGC CCACCTAGTA    3540

ACACTGGGAT CCGTGGTGCC GGTAGTGACT TTTCCCCTAA ACCAGGTCAA GCAACATTGC    3600

CTTCAAATCA GGGTGGCCCG TTAGGTGGTT ATGGTGTTCC TCCCCTTAAC CCTCTCCCAG    3660

TCCCTGGAGT TTCATCTTCT GCCACATTGC AACAGGAAAA TCGGGCAGCT GGCCAGCATA    3720

TAACACCATT AAAAAAACCT CTTCACAGTC CACAGGGTCT CCCTCTCCCC CTCCGTCCGG    3780

AAACTAATTT CCCTGGGGGC CAGGCACCCT TGCAGAATCC TTATGCTTAT AGCAGCCAGT    3840

TGCCTACCTC TCAGCTGCCA CCACAGCAAA ACATCAGTCG TGCAACTGCT CCTCAAACTC    3900

CTTTGAACAT TAATCTACGG CCAACAACTG TGTCTTCTGC AACTGTTCAA TTTCCCCCTC    3960

GTTCCCAGCA GCAACCGCTA CAAAAGATGC AACATCCTCC TTCTGAGCTA GCTCAGCTCT    4020

TGTCGCAGCA AACTCAGAGT CTACAAGCAA CATTCCAATC GTCTCAGCAA GCAATTTCTC    4080

AGCTGCAGCA GCAGGTGCAG TCTATGCAGC AACCAAACCA AAATTTACCA CTCTCACAGA    4140

ATGGCCGAGC TGGTAAACAA CAGTGGGCTG GATCTGCAAT TCCAAGAGTG GCTAGCACCA    4200

CTGGTTCGAC ACCAGTGAGC TATGTGCAAA CAGCTGCACC TGCAGTAAGT CAGAGCGTAG    4260

GTTCTGTCAA ATGTACCTGG ACCGAGCATA CCTCGCCTGA TGGATTTAAA TATTATTACA    4320

ATGGTCTAAC GGGTGAAAGC AAGTGGGAAA AACCTGAGGA AATGATAGTG TTCGAACGAG    4380

AGCAACAGAA ACAGCAACAA CATCAAGAGA AGCCAACTAT ACAGCAGTCC CAGACCCAAT    4440

TACAGCCGTT GCAGCAACAA CCACAACAAG TTCAGCAGCA ATATCAGGGC CAGCAATTAC    4500

AGCAGCCGTT TTATTCTTCA CTGTATCCAA CTCCAGGGGC CAGCCATAAT ACTCAGTATC    4560

CATCATTGCC AGTTGGTCAA AATAGCCAGT TTCCTATGTC AGGAATTGGT CAGAATGCTC    4620

AGGATTATGC TCGGACACAT ATACCCGTGG GAGCTGCTTC AATGAATGAT ATATCAAGAA    4680

CTCAACAGAG CCGTCAATCT CCCCAAGAAC TCATGTGGAA GAATAAAACT TGAGGTACAT    4740

GAGACGAGGA GCTAAACTAT CTCAGTAGCT AGATAGAAAT TTCTGGAACT AATTAGTCAA    4800

GGAGAGGAAA AGCAGCAATG GTAGTGTCCT TAGTCTCTGA TTTTTTTAGT TAACCCCTTC    4860

AGTTATAATA GATAGGCGAT CGTAGACCAT CTGCATTCTA TCTTTTCTCT AATCAGATAT    4920
```

```
CTCCTCCTTT TCATTTTAA GAGCTGCCAA ACAATGGCCT GTTGTAACAT AACTAGCGCA    4980

AGTTATGTCT CATGTTGTGT TACTAGTAGT AACTTAGCTG GGTAAACCAA ACTTTGATCC    5040

AGATTAGGAG TCATATATAA TTATATAAAT AGAATATGTA CATTCATAGA TAAAAAAAAA    5100

AAAAAAAAAA AAA                                                       5113
```

(2) INFORMATION FOR SEQ ID NO: 3:

(i) SEQUENCE CHARACTERISTICS:
        (A) LENGTH: 747 amino acids
        (B) TYPE: amino acid
        (C) STRANDEDNESS:
        (D) TOPOLOGY: linear (ii) MOLECULE TYPE: peptide (iii) HYPOTHETICAL: YES (vi) ORIGINAL SOURCE:
        (A) ORGANISM: Arabidopsis thaliana
        (B) STRAIN: Columbia (xi) SEQUENCE DESCRIPTION: SEQ ID NO: 3:

```
Met Asn Gly Pro Pro Asp Arg Val Asp Phe Lys Pro Met Gly Pro His
 1               5                  10                  15

His Gly Gly Ser Phe Arg Pro Met Gly Phe Ala Tyr Asp Asp Gly Phe
                20                  25                  30

Arg Pro Met Gly Pro Asn Gly Gly Val Gly Gly Glu Gly Thr Arg Ser
            35                  40                  45

Ile Val Gly Ala Arg Tyr Asn Tyr Pro Ala Lys Tyr Pro Pro Ser Glu
50                  55                  60

Ser Pro Asp Arg Arg Arg Phe Ile Gly Lys Ala Met Glu Ser Asp Tyr
65                  70                  75                  80

Ser Val Arg Pro Thr Thr Pro Val Gln Gln Pro Leu Ser Gly Gln
                85                  90                  95

Lys Arg Gly Tyr Pro Ile Ser Asp His Gly Ser Phe Thr Gly Thr Asp
            100                 105                 110

Val Ser Asp Arg Ser Ser Thr Val Lys Leu Phe Val Gly Ser Val Pro
        115                 120                 125

Arg Thr Ala Thr Glu Glu Ile Arg Pro Tyr Phe Glu Gln His Gly
    130                 135                 140

Asn Val Leu Glu Val Ala Leu Ile Lys Asp Lys Arg Thr Gly Gln Gln
145                 150                 155                 160

Gln Gly Cys Cys Phe Val Lys Tyr Ala Thr Ser Lys Asp Ala Asp Arg
                165                 170                 175

Ala Ile Arg Ala Leu His Asn Gln Ile Thr Leu Pro Gly Gly Thr Gly
            180                 185                 190

Pro Val Gln Val Arg Tyr Ala Asp Gly Glu Arg Glu Arg Ile Gly Thr
        195                 200                 205

Leu Glu Phe Lys Leu Phe Val Gly Ser Leu Asn Lys Gln Ala Thr Glu
    210                 215                 220

Lys Glu Val Glu Glu Ile Phe Leu Gln Phe Gly His Val Glu Asp Val
225                 230                 235                 240

Tyr Leu Met Arg Asp Glu Tyr Arg Gln Ser Arg Gly Cys Gly Phe Val
                245                 250                 255

Lys Tyr Ser Ser Lys Glu Thr Ala Met Ala Ala Ile Asp Gly Leu Asn
            260                 265                 270

Gly Thr Tyr Thr Met Arg Gly Cys Asn Gln Pro Leu Ile Val Arg Phe
```

```
            275                 280                 285
Ala Glu Pro Lys Arg Pro Lys Pro Gly Glu Ser Arg Asp Met Ala Pro
    290                 295                 300
Pro Val Gly Leu Gly Ser Gly Pro Arg Phe Gln Ala Ser Gly Pro Arg
305                 310                 315                 320
Pro Thr Ser Asn Phe Gly Asp Ser Ser Gly Asp Val Ser His Thr Asn
                325                 330                 335
Pro Trp Arg Pro Ala Thr Ser Arg Asn Val Gly Pro Ser Asn Thr
                340                 345                 350
Gly Ile Arg Gly Ala Gly Ser Asp Phe Ser Pro Lys Pro Gly Gln Ala
                355                 360                 365
Thr Leu Pro Ser Asn Gln Gly Gly Pro Leu Gly Tyr Gly Val Pro
370                 375                 380
Pro Leu Asn Pro Leu Pro Val Pro Gly Val Ser Ser Ala Thr Leu
385                 390                 395                 400
Gln Gln Glu Asn Arg Ala Ala Gly His Ile Thr Pro Leu Lys Lys
                405                 410                 415
Pro Leu His Ser Pro Gln Gly Leu Pro Leu Pro Leu Arg Pro Glu Thr
                420                 425                 430
Asn Phe Pro Gly Gly Gln Ala Pro Leu Gln Asn Pro Tyr Ala Tyr Ser
                435                 440                 445
Ser Gln Leu Pro Thr Ser Gln Leu Pro Pro Gln Gln Asn Ile Ser Arg
    450                 455                 460
Ala Thr Ala Pro Gln Thr Pro Leu Asn Ile Asn Leu Arg Pro Thr Thr
465                 470                 475                 480
Val Ser Ser Ala Thr Val Gln Phe Pro Pro Arg Ser Gln Gln Gln Pro
                485                 490                 495
Leu Gln Lys Met Gln His Pro Pro Ser Glu Leu Ala Gln Leu Leu Ser
                500                 505                 510
Gln Gln Thr Gln Ser Leu Gln Ala Thr Phe Gln Ser Ser Gln Gln Ala
                515                 520                 525
Ile Ser Gln Leu Gln Gln Val Gln Ser Met Gln Pro Asn Gln
                530                 535                 540
Asn Leu Pro Leu Ser Gln Asn Gly Arg Ala Gly Lys Gln Gln Trp Ala
545                 550                 555                 560
Gly Ser Ala Ile Pro Arg Val Ala Ser Thr Thr Gly Ser Thr Pro Val
                565                 570                 575
Ser Tyr Val Gln Thr Ala Ala Pro Ala Val Ser Gln Ser Val Gly Ser
                580                 585                 590
Val Lys Cys Thr Trp Thr Glu His Thr Ser Pro Asp Gly Phe Lys Tyr
                595                 600                 605
Tyr Tyr Asn Gly Leu Thr Gly Glu Ser Lys Trp Glu Lys Pro Glu Glu
    610                 615                 620
Met Ile Val Phe Glu Arg Glu Gln Lys Gln Gln His Gln Glu
625                 630                 635                 640
Lys Pro Thr Ile Gln Ser Gln Thr Gln Leu Gln Pro Leu Gln Gln
                645                 650                 655
Gln Pro Gln Gln Val Gln Gln Tyr Gln Gly Gln Gln Leu Gln Gln
                660                 665                 670
Pro Phe Tyr Ser Ser Leu Tyr Pro Thr Pro Gly Ala Ser His Asn Thr
                675                 680                 685
Gln Tyr Pro Ser Leu Pro Val Gly Gln Asn Ser Gln Phe Pro Met Ser
    690                 695                 700
```

```
Gly Ile Gly Gln Asn Ala Gln Asp Tyr Ala Arg Thr His Ile Pro Val
705                 710                 715                 720

Gly Ala Ala Ser Met Asn Asp Ile Ser Arg Thr Gln Gln Ser Arg Gln
            725                 730                 735

Ser Pro Gln Glu Leu Met Trp Lys Asn Lys Thr
            740                 745
```

(2) INFORMATION FOR SEQ ID NO: 4:

(i) SEQUENCE CHARACTERISTICS:
        (A) LENGTH: 9048 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Brassica (xi) SEQUENCE DESCRIPTION: SEQ ID NO: 4:

```
GTTAACGGAT CACACAGTAT AATATAAAAC TAGGTGTTTT GCCCGCACAT GCGAGCATAA      60

TTTTCTCATC AATACTTATT AGTTTATATC TTATTAATCT AAAACCAGCA TGATAAGTTA     120

TTATTTATGT TTTCAGATAG TTAAATCAAA CATCAAAGTA TTTATATATG TCAAATATTT     180

TATCAAAAAT ATATACTTAT TATTGTGTTA AATTTTTTAA AACACTCATA TCTTAGAAAT     240

AGTTTAGAAA ATATCTTTAT ATAAATGTTT TTTAACTTTT ATAATAAAAA TATTGTTTTC     300

AGATAGCAAC AAAATATATA TAGAATTAAC TTATTTTTAA ATTTTTTGAT AATTTTATTA     360

TATTATTTAA GAATCAATTA TTTATATTAA TATAACATAT AATTTTCACT GATTAAATAA     420

AATTCGTTTT TAATTATATA AATTCATTAA GAGTATTGTT TTAATAACAC ATTAGCGAAC     480

ATCAGCTAGA AATTAATAAT AAATCAATAA CCTAGCTAAA AGTCTAAAAC CTAATAAAAT     540

ATGACAAATA AGAAAAATTA ACTAAATTTT AATATAAAAT ATAAATTTAA TATTACTAAA     600

ATAAAATTCA TTTTTAATAT ATATAAGATT CTTAAGGGTA TTTTTTAAAT TAATAAAATTA     660

GTGACTTAGC TAAAAATAAA TAATAAATCA ATGATTTAGC TAAAACCTAA TAAAAACATG     720

ACAAATAAGC AAATTTACTA AAATTATTGA TAATATAAAA TATGATTGAT TCTTTAATAC     780

AAAATTAAAA TAAGAGTTTT TTTAAATCAA ACATAAGTCT GCCGTATCGG TGTTAAAAAA     840

AAAATCATTA ATAGTGTCGT AGGAATTATG TATTTCCATT AGCGAATAAA ATTGAAGCAG     900

AGTGTTGGAG GATAGCTCAA CGTATAGGCG AGATTATGGA GATTGATATG GGAGTTGCCG     960

TAACGGACAC AACTGTTCCT CTGCAAAGAA ACGTCCTAC TAGATGGACA TGTCAAGTTG     1020

ATGCATCCTG GATAAATGAA AGAAACATAT CTGGACTTGG CTTTGTGTTA ATGGATGGTG    1080

ACTTCCCAAT ACTGTTTGTA TCAACGGCCG ATATACACGC ACCAAATCAC CACTGCAAGC    1140

GGAACGTGAA GGTTTGCTAT GGGCAATGCA AGAGATACTG AAGTTTGGAC GCAGAGTGAT    1200

GGTCTTTCAA TCGACTATGA ACAACTGGTT ATACTCATTC AAAAGGAGGA AGATGGCCTG    1260

CTTGGACTCG GAGCTCGACG AAATACAAGT TGTATCAAAG AATTTTCTGA AATTTCTATT    1320

GCTTATATTC CTAGATCTTT AAAATTCCGT ACGAATAGCC TAGCAAAAGG TGTCGATCAC    1380

CCGCATCACG ATCAGCTTTT GTAACCCTTT GCACCAGTGG CTAGCCCACA GCTAGCATGA    1440

GGGTGCAAAA GAGAATAAGT CGAAACAAGC TAGCATGAGG GTGCCAAAAA AGAGAATAAA    1500
```

-continued

```
GTCGAAAGTA AAACTGAATA TCCAATGAAC AAAATTATCA GAAATCCATA TTTATGTGGA      1560

TGTCTATATG GGACAAACAA TTTTTTTAGA TCAATCCTAA AATATATAAT TTAAAAAAAC      1620

CATTTAAACA AACCATCAAA ATTTTGAATA TTACACCAAA AAAAAATATA AAGACCAACT      1680

ATATTATATT CATGTATAAT GTGTAGTGGT AAGATTCAAA AAAATTAACT TACTTTACAG      1740

TAAGGGAAAA TTAGATTTTT TATTCCATAT TTACAGTAAA AACATAACAT TTTATAAAAC      1800

TAAACAATTG ACATAATAGT ACAAAATATG AAAAAAAAAT CAAAATACTA AGAACCTACT      1860

ATTAGTTAAA TTAAGTACAG TCAAGTCAAC TAGTATGTGA ATGAGATTTA ACTTACAAAT      1920

TCATTACGAG ACAATAGCAC ATTTAGAAGA ATAACATGTA GATTGATGTG CACACAAAAA      1980

AAAACCAACG GGTACAAATG TTAACCGCTC CACCGGTCGA ACCATAATCC AGACCGGTTT      2040

TGCTATTTAA ACCGCTCAAA TCGCAAAGTA CGTTTCGCTT ACTTCCAGCA AACCACCATT      2100

GATCTCTCCT CCAATTCACA AATCCAATTT CTCTAGGGTT TGATTTCTTC GACTTGAATT      2160

GCATTTCCAT CCGAATTTCC CCAAATTCGT CAAGCTGGAT AGGCACCGAG GGGATCGCCA      2220

CGAGAGTGCC TTACGACGAT TCCTACCGTA ACCACCGAGC TCACCTAGAG GTCCCCCTCT      2280

ACTCTCAGAT TCACCCTCCA TGTCACGTTT CGGCGAGGAT GACGAAGGTT TCAGCCGCCG      2340

TCGTCGCCGT GGAAACAGCC TAGCAATTAT CAGTTGGATG GGACAGAGGA GGTGGCGATC      2400

GACGCTGGGA AGATGACGGC CACGATCGTA TTTCACAGAG AGGCGTGGGA GAGTAGAATT      2460

TCAGCCTATG GGTTATGGCT TCGACGGAGG TTTTCCGCCG ATGAGTCGCG ACGGAGGATT      2520

TTGGCCTAAC GTGCCAGTGA ATTTTCCGCC ATCGGAAAGT CCAGATGCAG GGGGATATTC      2580

CGGCGGCAGG GGATTTCAAT CAACGGGGCC TGCTTACTCT GTGAGATTGA CTTCACCGCC      2640

GATCCAGCAG CCTCTTTCTG GTCAGAAAAG AGGTCGTCCT CTCTCGGAGC AGAGTAGCTT      2700

TACTGGAACT GGTAAGCTTG GGCTCACTCT ACTGTAATCG AGTTGTTTAG AGTTAACAGT      2760

GGTTCATTTT ATACTTGTAT GTGATAATCA GGCTATTTCC AAACTAAATT ACCTTTACTG      2820

GATCATTCGT TTTGCAGATT TACTGATAGT AGCAGTATGG TGAAGCTTTT TGTTGGCTCT      2880

GTACCAAGGA CAGCTACAGA AGAAGAAGTG AGTTCATCTT TTTCTTATTT TCCTAATTTC      2940

TTCTCAATAT ATATGCACTT TCTTGAGGCA ATCTAAACCA CGAAGCTCGT AGACTCTGTT      3000

CATAAGCCGT TCTTGTTTAT CATTTTGGTT TTCATAGGTC CGTCCCTTTT CGAACAACAC      3060

GGTAAATGTT CTTGAGGTTG CTTTTATCAA GGACAAGAGA ACAGGACAGC AGCAAGGTAT      3120

GTTTATCTCC ATTTTACTAG GAACAGTCGT GATTTATGCT TCTAAATTTT TCAGGTCTCC      3180

TGAAAAGGCT GATGGGAACG AACCCCAGTC TCATCATTGG CCTCCATTAG TTTTCAACAA      3240

TTTTCGGGCT TTTGCTTATG CTAGCGAGCG TCTTATCTGT GTTGCTTTGG CACAGAAGAA      3300

GGCTGCCTGT TTAGTTTACT AAGAAAGGGT TTTTGTATTG ACCTTGGTAA AATAGTTTTT      3360

GCGACTTGTG TCCATCCTAG AACCTTAGTT GTGTTTGAAC AGTGTAGCAG ACTTTATCAT      3420

GTTTTAGAGT TGGAGTTAAT GTACATAAAA TTGAACAGAT GTTTTACTGT TGCCTTTTAG      3480

TTGGCACTGG TTTAAAGAAC GTTGTTTTCT CCTTTCCTAT TGAATTCAGT ATCTCTTTAC      3540

TCTTCCTTTC GATGAATGAA AATGGTGTAT ATGGTCTTGA CTGGATGAAT GTATTTTAC      3600

TTGGTAGTCT TACAACGTTC ATAAAATGGT TTGATTGATA AACCACCCCT GCTAGTCAAT      3660

ATTTGGCAGT TCTTAGTGA TTATATCATG TTGGATGTTT TGTTTCTTTA GTTTCTTTAA      3720

TATCAACTTT GGATGTACCG TCTCTATTGG TTGATGATGA AATTATTTTT TACCATTTTG      3780

GATGCTTGAT GCCTTAATGA ATGGATCTTT CCTTTTTTTC TTATTGTGGA TGGCCGAGGA      3840
```

-continued

```
ACTATAATGA ATGTTCTCTT CGCTTTTTTT GAATGGCCTG GGATGTGGAC TTCTTGTATG    3900

TTCTCACTTT CATTGATGAA TGACTGTTTC GTTGAGTAGC TCTATTGTTC TGTATGGTAA    3960

CGCTAACACT GCTGATCTAC ATTATGTGGA AGAGATCATA TGTCTAATGA TATTTTTTTT    4020

CTATGTACCT TTCACCAACC AAGCTCAAAA GCTTGGTTTC AGTTTTTAGT GGTCTTATTC    4080

TATATAGAGC TTGGTTTCAG TTTTTAGTGG TCTTATTCTA TATATTGAGA TTGCTCTTGA    4140

AAAATTCCAT CAAAGTTCTG TCTTTATGAT GCAAGTGTGA AGAATTACTA GATGATGAGT    4200

GATGTATTAT TTAATAATTC GGGACTTTCC AAGAAGTTAT TGTACGGTGA CATAAAAGCT    4260

TTTACTCATC CCGTTATCAC GGTTTGACTG TAGTAGATTT GACACATTCC TTGGTTTGAA    4320

ATGTTACATG GTGCTAAGAT ATGGAAGGCA ACGATTATTA TAATTTCTTA GAAATACGTC    4380

TTAGCTTTCA CTCGCTCTCA TTGCTTCGAT CAGCATCAGG CATGAGCCGC CTTAGTATGT    4440

ATTTAATGAA GCAAGTGTCA TTCTTCTCTA TATGCAACTA TTACCAATGA ATTGACGTTG    4500

GGTTGTGGTT ATGTCTCTCA GAACTGTAAT TCTTTTTGTG AATGTCGTCA AATGTGTGGT    4560

GTATGTTGTA TGGTGTATGG TGACGAAAAT GTGATGTATG GCTCTAGTTT TAATTATATC    4620

ATTTGTTACT TAGCAGTGAT TGAGAACTCT TAACTTGTAA TTTTATCTAA TTTTTTTTTG    4680

CAGTGATTGG ATTCTTTTTG CGTAATATAT ATTTTATTTG CAAATACCGA CTGTGTTCTT    4740

TTTAAATAGT TTAAAGGCAT ATGCTTTATT TGAAGCACAT TAGTTTATTA TTCTCTCCAT    4800

CAAATCTACT ACAGTAATGT AAGTCGAGGC TGTCAGGACA TGTCTTATGA TTTTCGTACT    4860

GAAACTTATG TGCTTTCAAT GTGGTCGTGG CTTGTACATT TGTAAAGAAA CTATTTACTA    4920

GTATCTCTTG ATGTTTGATG GAGGGACAAG TGGAACCTTG AACAGAAGCT TATGTAGCAG    4980

TCTTTAATGC AGGCTGTTGT TTTGTAAAAT ATGCAACTTC TGAAGATGCG GATAGGGCCA    5040

TTAGAGCATT GCACAATCAG ATCACTCTTC CTGGGGTAAC TACCATTGAT GCCTTCTCTT    5100

ATCAAGGACA GGAAAATACA GGTTAACTCT ATCTTTACAA TTTGCTGATT CCCAGGGAAC    5160

TGGCCTTGTT CAAGTTCGAT ATGCTGATGG GGAGAGAGAA CGCATAGGTA ATCAACTTTC    5220

GCGCCATATT ATCTGAATCT GGCCTTCATT GTCTGGTATA CATAGGGTGA CCATACGCTG    5280

TACAAATTCA AATTACGAGA ATTGAGATAA TGTGGGAAAC TATATGAATC TTAAGGAAGT    5340

GGATCCTTTT TTCTGTGGTC CTTGCCTCAC TCTCAAGTAT TAACTGATTG AATTTACTTC    5400

TTCTGAAGGT GCGGTAGAGT TTAAGCTTTT TGTTGGTTCC TTAAACAAGC AAGCCACTGA    5460

AAACGAGGTT GAGGAGGTAT GTCTCATATC CTACTTTTTG ATGGAAAGTA ATTACTTATG    5520

TCTGATTTAC AAAGAGGGAA GCGTTCTAAA TTTAGATATT ACAGTATCCC CTGTCGCCTT    5580

AGCTGGTAAT TTTAGTGATT ATATGACAAT TTAGTAGTCC TCTTGGAAGG GTCAGCGGCT    5640

TGAAATTTTG TGTCAACTAT TCGAGCGCTT ACACATTTTA CTAACTGAGT GATCTCTTCT    5700

TTCAAATGGA CTGACTGAGT GATCTCTTCT TCCAAATGGA TGTAACTTTT TGGCTGTCAG    5760

CTTTCTTTTC TCAGTAAATA TGATGAAGAT GTGAACGGCT ACTTTGTCCT GTTGTTGCTT    5820

TAACAGCTCT TTTTGCAATT TGGTCGCGTG GAGGATGTCT ATCTCATGCG TGATGAATAT    5880

AGACAGAGTC GTGGTATGTC TGGTAACTGC CACTAGACTC TATAACTCGT TGATGGTGT    5940

TGATATGGTC AAACTGTTTT TGACACTCAT TTAGGATGCG GGTTTGTTAA ATATTCAAGC    6000

AAAGAGACGG CCATGGCAGC TATCGATGGT CTCAATGGAA CTTATACCAT GAGAGTAAGC    6060

TGTGAAATCA CATGAGTATC TCACTTTCTC TCATTATCCC CTCTAGACCT GTTTTGTTTA    6120

CTGGCCTCTT TCCCTTCTCC AGGGTTGCAA TCAGCCATTG ATTGTTCGGT TTGCTGATCC    6180

AAAGAGGCCT AAACCGGGCG AGTCAAGGTA TTGCCTTGGA GACTATATTT TGAATTCATT    6240
```

-continued

```
ATAATGCTAA TATCAAAAAA ATTGTGTCTA CTGTCATTGT TGTTCTATT GAGTTACATT      6300

TATGAGAATC TTTTGGGGCA TGGGTGGAGG AGAGCTGCGA ACCTTATTCC TTCTCCAGTT      6360

ATTACTTGAA TGCGATGAAT TTCTTTCTAT ATATCCTTAA CTAGTTTCTG TTTCCAGGGA      6420

AGTGGCACAT CCTGTTGGAC TTTGTTCAGG GCCTCGTTTT CAAGCTTCAG GACCAAGGTG      6480

ACTGGGGTGA AAGGAGATCG TTGTTTTTGT CATCAATTAA TTATATATTT TGACTAAACG      6540

TGGTCTCCTT ATCTTCATTT GTTAGGCCTA CATCTAACCT TGGTGACCTT AGTGTGGATG      6600

TGAGCCACAC AAATCCTTGG CGTCCTATGA ATTCACCAAA CATGGGGCCA CCTGGTAACA      6660

CTGGGATCCG TGGTACCGGA AGTGACTTGG CTCCTAGGCC AGGTCAAGCC ACATTACCTT      6720

CAAATCAGGT AAGAACAGCT TGATGATCAT GTATATTATC TTATATGTAC ACACCCAATC      6780

ACACATAAAG TAATCGGGCA TAAGGTTTTA CATGTATTGT GTGAGTAGGA CGAACATAAT      6840

TTATATGCTG CACATATATG AGCGTATGGA CTCTTGAAAA GAAGCATGAA GTTCCGACCT      6900

TCCAGCTTTT CATATGATGC AGCAAACTTG ATGTGTTTTG CATTGAAATG ATATGGCTTT      6960

GATTTGCATT TTGTCAGTTT CTAAGGAGTT TTTTTCTTCA ATAATTTCTA CTTCTGATGT      7020

TAGCTTTATT TGTGGCATTC TATAATGTTA GGGAGGTCCA TTGGGTGGTT ATGTTGTTCC      7080

TGCCATTAAC CCTCTACCAG TCTCATCCTC TGCCACATCG CAACAGGTAC TTCAGCTGAA      7140

TTTTTCCAAT AAAGAAAATC TGAAAATGTT GTGTTGATCA GTTAATTTCA ACTGTTTCTA      7200

TTCCATAGCA AAACCGGGGA GCTGGCCAGC ATATGTCACC ATTACAAAAA CCTCTTCACA      7260

GTCCACAGGA TGTGCCCCTT CGACCACAAA CTAATTTCCC TGGGGCCCAA GCATCCTTGC      7320

AGAATCCTTA TGGTTATAGC AGCCAGTTGC CTACTTCTCA GCTGCGGCCA CAACAAAACG      7380

TCACTCCTGC AACAGCTCCT CAAGCTCCTT TGAACATCAA CCTACGGCCA ACACCTGTAT      7440

CTTCTGCAAC TGATCAATTG CGCCCTCGTG CTCAGCAGCC ACCGCACAA AAGATGCAAC       7500

ATCCTCCTTC TGAGCTAGTT CAGCTCTTGT CACAACAGAC TCAGACTCTA CAAGCAACCT      7560

TCCAATCATC TCAGCAAGCA TTTTCTCAAC TGCAGGAGCA GGTGCAGTCC ATGCAGCAAC      7620

CAAACCAAAA ATTACCAGGC TCACAGACTG GCCATGGTAA ACAGCAGGTA CAAACATAGT      7680

TCCCTGTTGC ATCTGTCCAG TCCAGTTCCT CAGCTGTTTT TGTTGTTTTA ACTTACAATT      7740

ATTTCCTGAT GTCTAAGTAT TCAATCCTTC ATATATTTTA GTAGTCCCTC TTTTTTATTA      7800

TGTTTTTCTC GGTTGCTTCT CTATCAGTGG GCTGGATCTG CAATTCCGAC AGTTGTTAGC      7860

ACCACTGCTT CTACACCAGT TAGCTATATG CAAACAGCTG CACCTGCAGC AACTCAGAGT      7920

GTTGTTTCTC GCAAATGTAA CTGGACCGAG CATACCTCGC CTGATGGATT TAAGTATTAT      7980

TACAACGGTC AAACCGGTGA AAGCAAGGTG AGAAACGTGG TTCCTCTTTA GTTATGTTCT      8040

CTTGTGAGTT TCAGGAGGAT TCCTTGTATT TGCTGTGCTA TTTATTATCC TTGAACATGT      8100

ATATGTATAG ATTTCATATT TGAAGTTCAT CAATACGTGT CGTAATATAA TTGACTTTTG      8160

CAGTGGGAAA AACCTGAGGA AATGGTATTG TTCGAACGTC AGCAACAGCA GCCAACTATA      8220

AATCAGCCCC AGACCCAATC ACAGCAGGCT CTTTATTCCC AGCCGATGCA GCAACAACCA      8280

CAACAGGTTC ACCAGCAATA TCAGGGCCAA TATGTACAGC AGCCTATTTA TTCTTCAGTG      8340

GTTGGTTCTG TTTTCTTGCT GCTTACATCC ATATAGTTTT CTCACATGGT CTCTAACTTG      8400

AATATGTATT CTTTTCCATT TGGAGTTGCA GTATCCAACT CCAGGGGTCA GCCAGAATGC      8460

TCAGGTGTAT ATTTAGTTAA ATTATTTGCT TATCTTTCAT TTCAGAATTT GATCATTGAG      8520

TTACCAATCT AGTGGGTATA AGGAGACGGG CCACTTTATG CAATAAACCA TGGTTTTACA      8580
```

-continued

```
AGCGTTTTGA ATATACAGAT ACAAACATCT AAATTTGATC ATTTCAAAAT TTGATCATCG    8640

AGTTCCCTTT TCAATGCAGT ATCCGCCGCC ATTGGGAGTT AGTCAAAATA GCCAGGTACA    8700

TATTTGAACC TTATTTCACG TGGGACTAAT TGAAATTCGA TTTTGATATG CATTTCATAA    8760

ATGTGAAGAT TTGATGAGTG GTCGTTTTGG TAGCGTTTTA GAAAACGATA TGCATATATT    8820

CTCTAGTTGA ATATTTCTTT TTTCTGGAAC ATGCAGTTTC CTATGTCAGG CACCGGTCAA    8880

AATGCTCAGG TACATATTAT ATCATGCATC ATATCTTCTG ATTAACTTCA AATTTAATCA    8940

GAAAACATAC GTGAGATTCC AGTAGAAACA AAATCGATAT GACTGTATTG GTTGGAAATG    9000

GTTAAGGCAG AGCTCATGTT CTAATGTGTT AAAATTTTCT AGGAATTT                  9048
```

(2) INFORMATION FOR SEQ ID NO: 5:

(i) SEQUENCE CHARACTERISTICS:
        (A) LENGTH: 675 amino acids
        (B) TYPE: amino acid
        (C) STRANDEDNESS:
        (D) TOPOLOGY: linear (ii) MOLECULE TYPE: peptide (iii) HYPOTHETICAL: YES (iv) ANTI-SENSE: NO (vi) ORIGINAL SOURCE:
        (A) ORGANISM: Brassica napus (xi) SEQUENCE DESCRIPTION: SEQ ID NO: 5:

```
Met Gly Tyr Gly Phe Asp Gly Gly Phe Pro Pro Met Ser Arg Asp Gly
 1               5                  10                  15

Gly Phe Trp Pro Asn Val Pro Val Asn Phe Pro Pro Ser Glu Ser Pro
                20                  25                  30

Asp Ala Gly Gly Tyr Ser Gly Gly Arg Gly Phe Gln Ser Thr Gly Pro
            35                  40                  45

Ala Tyr Ser Val Arg Leu Thr Ser Pro Pro Ile Gln Gln Pro Leu Ser
        50                  55                  60

Gly Gln Lys Arg Gly Arg Pro Leu Ser Glu Gln Ser Ser Phe Thr Gly
65                  70                  75                  80

Thr Gly Leu Leu Ile Val Ala Val Met Val Lys Leu Phe Val Gly Ser
                85                  90                  95

Val Pro Arg Thr Ala Thr Glu Glu Val Arg Pro Phe Ser Asn Asn
                100                 105                 110

Thr Val Asn Val Leu Glu Val Ala Phe Ile Lys Asp Lys Arg Thr Gly
            115                 120                 125

Gln Gln Gln Gly Cys Cys Phe Val Lys Tyr Ala Thr Ser Glu Asp Ala
        130                 135                 140

Asp Arg Ala Ile Arg Ala Leu His Asn Gln Ile Thr Leu Pro Gly Gly
145                 150                 155                 160

Thr Gly Leu Val Gln Val Arg Tyr Ala Asp Gly Glu Arg Glu Arg Ile
                165                 170                 175

Gly Ala Val Glu Phe Lys Leu Phe Val Gly Ser Leu Asn Lys Gln Ala
            180                 185                 190

Thr Glu Asn Glu Val Glu Glu Leu Phe Leu Gln Phe Gly Arg Val Glu
        195                 200                 205

Asp Val Tyr Leu Met Arg Asp Glu Tyr Arg Gln Ser Arg Gly Cys Gly
    210                 215                 220

Phe Val Lys Tyr Ser Ser Lys Glu Thr Ala Met Ala Ala Ile Asp Gly
```

```
                  225                 230                 235                 240

Leu Asn Gly Thr Tyr Thr Met Arg Gly Cys Asn Gln Pro Leu Ile Val
                    245                 250                 255

Arg Phe Ala Asp Pro Lys Arg Pro Lys Pro Gly Glu Ser Lys Glu Val
                    260                 265                 270

Ala His Pro Val Gly Leu Cys Ser Gly Pro Arg Phe Gln Ala Ser Gly
                    275                 280                 285

Pro Lys Pro Thr Ser Asn Leu Gly Asp Leu Ser Val Asp Val Ser His
                    290                 295                 300

Thr Asn Pro Trp Arg Pro Met Asn Ser Pro Asn Met Gly Pro Pro Gly
    305                 310                 315                 320

Asn Thr Gly Ile Arg Gly Thr Gly Ser Asp Leu Ala Pro Arg Pro Gly
                    325                 330                 335

Gln Ala Thr Leu Pro Ser Asn Gln Gly Gly Pro Leu Gly Gly Tyr Val
                    340                 345                 350

Val Pro Ala Ile Asn Pro Leu Pro Val Ser Ser Ala Thr Ser Gln
                    355                 360                 365

Gln Gln Asn Arg Gly Ala Gly Gln His Met Ser Pro Leu Gln Lys Pro
                    370                 375                 380

Leu His Ser Pro Gln Asp Val Pro Leu Arg Pro Gln Thr Asn Phe Pro
    385                 390                 395                 400

Gly Ala Gln Ala Ser Leu Gln Asn Pro Tyr Gly Tyr Ser Ser Gln Leu
                    405                 410                 415

Pro Thr Ser Gln Leu Arg Pro Gln Gln Asn Val Thr Pro Ala Thr Ala
                    420                 425                 430

Pro Gln Ala Pro Leu Asn Ile Asn Leu Arg Pro Thr Pro Val Ser Ser
                    435                 440                 445

Ala Thr Asp Gln Leu Arg Pro Arg Ala Gln Gln Pro Pro Gln Lys
                    450                 455                 460

Met Gln His Pro Pro Ser Glu Leu Val Gln Leu Leu Ser Gln Gln Thr
    465                 470                 475                 480

Gln Thr Leu Gln Ala Thr Phe Gln Ser Ser Gln Ala Phe Ser Gln
                    485                 490                 495

Leu Gln Glu Gln Val Gln Ser Met Gln Gln Pro Asn Gln Lys Leu Pro
                    500                 505                 510

Gly Ser Gln Thr Gly His Gly Lys Gln Gln Trp Ala Gly Ser Ala Ile
                    515                 520                 525

Pro Thr Val Val Ser Thr Thr Ala Ser Thr Pro Val Ser Tyr Met Gln
                    530                 535                 540

Thr Ala Ala Pro Ala Ala Thr Gln Ser Val Val Ser Arg Lys Cys Asn
    545                 550                 555                 560

Trp Thr Glu His Thr Ser Pro Asp Gly Phe Lys Tyr Tyr Asn Gly
                    565                 570                 575

Gln Thr Gly Glu Ser Lys Trp Glu Lys Pro Glu Glu Met Val Leu Phe
                    580                 585                 590

Glu Arg Gln Gln Gln Pro Thr Ile Asn Gln Pro Thr Gln Ser
                    595                 600                 605

Gln Gln Ala Leu Tyr Ser Gln Pro Met Gln Gln Pro Gln Gln Val
                    610                 615                 620

His Gln Gln Tyr Gln Gly Gln Tyr Val Gln Pro Ile Tyr Ser Ser
    625                 630                 635                 640

Val Tyr Pro Thr Pro Gly Val Ser Gln Asn Ala Gln Tyr Pro Pro Pro
                    645                 650                 655
```

```
Leu Gly Val Ser Gln Asn Ser Gln Phe Pro Met Ser Gly Thr Gly Gln
            660                 665                 670

Asn Ala Gln
        675
```

(2) INFORMATION FOR SEQ ID NO: 6:

(i) SEQUENCE CHARACTERISTICS:
        (A) LENGTH: 78 amino acids
        (B) TYPE: amino acid
        (C) STRANDEDNESS:
        (D) TOPOLOGY: linear (ii) MOLECULE TYPE: peptide (iii) HYPOTHETICAL: YES (iv) ANTI-SENSE: NO (v) FRAGMENT TYPE: internal (vi) ORIGINAL SOURCE:
        (A) ORGANISM: Arabidopsis thaliana
        (B) STRAIN: Columbia (xi) SEQUENCE DESCRIPTION: SEQ ID NO: 6:

```
Asp Val Ser Asp Arg Ser Ser Thr Val Lys Leu Phe Val Gly Ser Val
1               5                   10                  15

Pro Arg Thr Ala Thr Glu Glu Glu Ile Arg Pro Tyr Phe Glu Gln His
            20                  25                  30

Gly Asn Val Leu Glu Val Ala Leu Ile Lys Asp Lys Arg Thr Gly Gln
        35                  40                  45

Gln Gln Gly Cys Cys Phe Val Lys Tyr Ala Thr Ser Lys Asp Ala Asp
    50                  55                  60

Arg Ala Ile Arg Ala Leu His Asn Gln Ile Thr Leu Pro Gly
65                  70                  75
```

(2) INFORMATION FOR SEQ ID NO: 7:

(i) SEQUENCE CHARACTERISTICS:
        (A) LENGTH: 71 amino acids
        (B) TYPE: amino acid
        (C) STRANDEDNESS:
        (D) TOPOLOGY: linear (ii) MOLECULE TYPE: peptide (iii) HYPOTHETICAL: YES (iv) ANTI-SENSE: NO (v) FRAGMENT TYPE: internal (vi) ORIGINAL SOURCE:
        (A) ORGANISM: Arabidopsis thaliana
        (B) STRAIN: Columbia (xi) SEQUENCE DESCRIPTION: SEQ ID NO: 7:

```
Arg Glu Arg Ile Gly Thr Leu Glu Phe Lys Leu Phe Val Gly Ser Leu
1               5                   10                  15

Asn Lys Gln Ala Thr Glu Lys Gly Val Glu Glu Ile Phe Leu Gln Phe
            20                  25                  30

Gly His Val Glu Asp Val Tyr Leu Met Arg Asp Glu Tyr Arg Gln Ser
        35                  40                  45

Arg Gly Cys Gly Phe Val Lys Tyr Ser Ser Lys Glu Thr Ala Met Ala
    50                  55                  60
```

```
Ala Ile Asp Gly Leu Asn Gly
 65                  70
```

(2) INFORMATION FOR SEQ ID NO: 8:

(i) SEQUENCE CHARACTERISTICS:
        (A) LENGTH: 36 amino acids
        (B) TYPE: amino acid
        (C) STRANDEDNESS:
        (D) TOPOLOGY: linear (ii) MOLECULE TYPE: peptide (iii) HYPOTHETICAL: YES (iv) ANTI-SENSE: NO (v) FRAGMENT TYPE: internal (vi) ORIGINAL SOURCE:
        (A) ORGANISM: Arabidopsis thaliana
        (B) STRAIN: Columbia (xi) SEQUENCE DESCRIPTION: SEQ ID NO: 8:

```
Trp Thr Glu His Thr Ser Pro Asp Gly Phe Lys Tyr Tyr Tyr Asn Gly
 1               5                  10                  15

Leu Thr Gly Glu Ser Lys Trp Glu Lys Pro Glu Glu Met Ile Val Phe
                20                  25                  30

Glu Arg Glu Gln
        35
```

(2) INFORMATION FOR SEQ ID NO: 9:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (iii) HYPOTHETICAL: YES (iv) ANTI-SENSE: NO (v) FRAGMENT TYPE: internal (vi) ORIGINAL SOURCE:
        (A) ORGANISM: Arabidopsis thaliana
        (B) STRAIN: Columbia (xi) SEQUENCE DESCRIPTION: SEQ ID NO: 9:

```
Phe Val Gly Ser Leu Asn Lys
 1               5
```

(2) INFORMATION FOR SEQ ID NO: 10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Degenerate
            oligonucleotide"

(iii) HYPOTHETICAL: YES (iv) ANTI-SENSE: NO

```
        (vi) ORIGINAL SOURCE:
              (A) ORGANISM: Arabidopsis thaliana
              (B) STRAIN: Columbia (xi) SEQUENCE DESCRIPTION: SEQ ID NO: 10:

TTYGTNGGNW SNYTRAAYAA RC                                                22

(2) INFORMATION FOR SEQ ID NO: 11:

(i) SEQUENCE CHARACTERISTICS:
              (A) LENGTH: 7 amino acids
              (B) TYPE: amino acid
              (C) STRANDEDNESS:
              (D) TOPOLOGY: linear (ii) MOLECULE TYPE: peptide (iii) HYPOTHETICAL: YES (iv) ANTI-SENSE: NO (v) FRAGMENT TYPE: internal (vi) ORIGINAL SOURCE:
              (A) ORGANISM: Arabidopsis thaliana
              (B) STRAIN: Columbia (xi) SEQUENCE DESCRIPTION: SEQ ID NO: 11:

Arg Gly Cys Phe Val Lys Tyr
1               5

(2) INFORMATION FOR SEQ ID NO: 12:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: other nucleic acid
              (A) DESCRIPTION:   /desc = "DEGENERATE
                  OLIGONUCLEOTIDE"

(iii) HYPOTHETICAL: YES (iv) ANTI-SENSE: YES (vi) ORIGINAL SOURCE:
              (A) ORGANISM: Arabidopsis thaliana
              (B) STRAIN: Columbia (xi) SEQUENCE DESCRIPTION: SEQ ID NO: 12:

TAYTTNACRA ANCCRCANCC T                                                 21

(2) INFORMATION FOR SEQ ID NO: 13:

(i) SEQUENCE CHARACTERISTICS:
              (A) LENGTH: 28 base pairs
              (B) TYPE: nucleic acid
              (C) STRANDEDNESS: single
              (D) TOPOLOGY: linear (ii) MOLECULE TYPE: other nucleic acid
              (A) DESCRIPTION:    /desc = "Oligonucleotide"

(iii) HYPOTHETICAL: YES (iv) ANTI-SENSE: NO (vi) ORIGINAL SOURCE:
              (A) ORGANISM: Arabidopsis thaliana
              (B) STRAIN: Columbia
```

(xi) SEQUENCE DESCRIPTION: SEQ ID NO: 13:

CAGGATCCTT CATCATCTTC GATACTCG                                                      28

(2) INFORMATION FOR SEQ ID NO: 14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "Oligonucleotide"

(iii) HYPOTHETICAL: YES (iv) ANTI-SENSE: NO (vi) ORIGINAL SOURCE:
            (A) ORGANISM: Arabidopsis thaliana
            (B) STRAIN: Columbia (xi) SEQUENCE DESCRIPTION: SEQ ID NO: 14:

GTCCCTCAGA TTCACGCTTC                                                                20

(2) INFORMATION FOR SEQ ID NO: 15:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "Oligonucleotide"

(iii) HYPOTHETICAL: YES (iv) ANTI-SENSE: YES (vi) ORIGINAL SOURCE:
            (A) ORGANISM: Arabidopsis thaliana
            (B) STRAIN: Columbia (xi) SEQUENCE DESCRIPTION: SEQ ID NO: 15:

CACTTTTCAA ACACATC                                                                   17

(2) INFORMATION FOR SEQ ID NO: 16:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION:   /desc = "Oligonucleotide"

(iii) HYPOTHETICAL: YES (iv) ANTI-SENSE: YES (xi) SEQUENCE DESCRIPTION: SEQ ID NO: 16:

GTTCTCTGTA CATTAACTC                                                                 19

(2) INFORMATION FOR SEQ ID NO: 17:

(i) SEQUENCE CHARACTERISTICS:
            (A) LENGTH: 20 base pairs
            (B) TYPE: nucleic acid
            (C) STRANDEDNESS: single

```
            (D) TOPOLOGY: linear (ii) MOLECULE TYPE: other nucleic acid
        (A) DESCRIPTION:   /desc = "Oligonucleotide"

(iii) HYPOTHETICAL: YES (iv) ANTI-SENSE: NO (vi) ORIGINAL SOURCE:
        (A) ORGANISM: Arabidopsis thaliana
        (B) STRAIN: Columbia (xi) SEQUENCE DESCRIPTION: SEQ ID NO: 17:

ATTGAGATTC TTACATACTG                                                 20

(2) INFORMATION FOR SEQ ID NO: 18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(iii) HYPOTHETICAL: YES (iv) ANTI-SENSE: YES (xi) SEQUENCE DESCRIPTION: SEQ ID NO: 18:

TAAGACATGT CTGACAG                                                    17

(2) INFORMATION FOR SEQ ID NO: 19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(iii) HYPOTHETICAL: YES (iv) ANTI-SENSE: YES (vi) ORIGINAL SOURCE:
        (A) ORGANISM: Arabidopsis thaliana
        (B) STRAIN: columbia (xi) SEQUENCE DESCRIPTION: SEQ ID NO: 19:

GTGATCTGAT TGTGCAG                                                    17

(2) INFORMATION FOR SEQ ID NO: 20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(iii) HYPOTHETICAL: YES (iv) ANTI-SENSE: YES (vi) ORIGINAL SOURCE:
        (A) ORGANISM: Arabidopsis thaliana
```

(B) STRAIN: Columbia (xi) SEQUENCE DESCRIPTION: SEQ ID NO: 20:

TAGACATCTT CCACATG                                                                17

(2) INFORMATION FOR SEQ ID NO: 21:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(iii) HYPOTHETICAL: YES (iv) ANTI-SENSE: YES (vi) ORIGINAL SOURCE:
        (A) ORGANISM: Arabidopsis thaliana
        (B) STRAIN: columbia (xi) SEQUENCE DESCRIPTION: SEQ ID NO: 21:

CAATGGCTGA TTGCAACCTC TC                                                          22

(2) INFORMATION FOR SEQ ID NO: 22:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(iii) HYPOTHETICAL: YES (iv) ANTI-SENSE: YES (vi) ORIGINAL SOURCE:
        (A) ORGANISM: Arabidopsis thaliana
        (B) STRAIN: columbia (xi) SEQUENCE DESCRIPTION: SEQ ID NO: 22:

TCTTTGGCTC AGCAAACCG                                                              19

(2) INFORMATION FOR SEQ ID NO: 23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(iii) HYPOTHETICAL: YES (iv) ANTI-SENSE: YES (vi) ORIGINAL SOURCE:
        (A) ORGANISM: Arabidopsis thaliana
        (B) STRAIN: Columbia (xi) SEQUENCE DESCRIPTION: SEQ ID NO: 23:

CAATGTGGCAGAAGATG                                                                 17

```
(2) INFORMATION FOR SEQ ID NO: 24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(iii) HYPOTHETICAL: YES (iv) ANTI-SENSE: YES (vi) ORIGINAL SOURCE:
        (A) ORGANISM: Arabidopsis thaliana
        (B) STRAIN: Columbia (xi) SEQUENCE DESCRIPTION: SEQ ID NO: 24:

AGGCCATTGT TTGGCAGCTC                                            20

(2) INFORMATION FOR SEQ ID NO: 25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION:   /desc = "Oligonucleotide"

(iii) HYPOTHETICAL: YES (iv) ANTI-SENSE: YES (vi) ORIGINAL SOURCE:
        (A) ORGANISM: Arabidopsis thaliana
        (B) STRAIN: columbia (xi) SEQUENCE DESCRIPTION: SEQ ID NO: 25:

CCCAGCTAAG TTACTACTAG                                            20

(2) INFORMATION FOR SEQ ID NO: 26:

(i) SEQUENCE CHARACTERISTICS:
        (A) LENGTH: 688 amino acids
        (B) TYPE: amino acid
        (D) TOPOLOGY: linear (xi) SEQUENCE DESCRIPTION: SEQ ID NO: 26:

Met Gly Phe Ala Tyr Asp Asp Gly Phe Arg Pro Met Gly Pro Asn Gly
1               5                  10                  15

Gly Val Gly Gly Glu Gly Thr Arg Ser Ile Val Gly Ala Arg Tyr Asn
            20                  25                  30

Tyr Pro Ala Lys Tyr Pro Pro Ser Glu Ser Pro Asp Arg Arg Arg Phe
        35                  40                  45

Ile Gly Lys Ala Met Glu Ser Asp Tyr Ser Val Arg Pro Thr Thr Pro
    50                  55                  60

Pro Val Gln Gln Pro Leu Ser Gly Gln Lys Arg Gly Tyr Pro Ile Ser
65                  70                  75                  80

Asp His Gly Ser Phe Thr Gly Thr Asp Val Ser Asp Arg Ser Ser Thr
                85                  90                  95

Val Lys Leu Phe Val Gly Ser Val Pro Arg Thr Ala Thr Glu Glu Glu
            100                 105                 110

Ile Arg Pro Tyr Phe Glu Gln His Gly Asn Val Leu Glu Val Ala Leu
```

-continued

```
            115                 120                 125
Ile Lys Asp Lys Arg Thr Gly Gln Gln Gln Gly Cys Cys Phe Val Lys
    130                 135                 140

Tyr Ala Thr Ser Lys Asp Ala Asp Arg Ala Ile Arg Ala Leu His Asn
145                 150                 155                 160

Gln Ile Thr Leu Pro Gly Gly Thr Gly Pro Val Gln Val Arg Tyr Ala
                165                 170                 175

Asp Gly Glu Arg Glu Arg Ile Gly Thr Leu Glu Phe Lys Leu Phe Val
            180                 185                 190

Gly Ser Leu Asn Lys Gln Ala Thr Glu Lys Glu Val Glu Glu Ile Phe
        195                 200                 205

Leu Gln Phe Gly His Val Glu Asp Val Tyr Leu Met Arg Asp Glu Tyr
    210                 215                 220

Arg Gln Ser Arg Gly Cys Gly Phe Val Lys Tyr Ser Ser Lys Glu Thr
225                 230                 235                 240

Ala Met Ala Ala Ile Asp Gly Leu Asn Gly Thr Tyr Thr Met Arg Gly
                245                 250                 255

Cys Asn Gln Pro Leu Ile Val Arg Phe Ala Glu Pro Lys Arg Pro Lys
            260                 265                 270

Pro Gly Glu Ser Arg Asp Met Ala Pro Pro Val Gly Leu Gly Ser Gly
        275                 280                 285

Pro Arg Phe Gln Ala Ser Gly Pro Arg Pro Thr Ser Asn Phe Gly Asp
    290                 295                 300

Ser Ser Gly Asp Val Ser His Thr Asn Pro Trp Arg Pro Ala Thr Ser
305                 310                 315                 320

Arg Asn Val Gly Pro Ser Asn Thr Gly Ile Arg Gly Ala Gly Ser
                325                 330                 335

Asp Phe Ser Pro Lys Pro Gly Gln Ala Thr Leu Pro Ser Asn Gln Gly
            340                 345                 350

Gly Pro Leu Gly Gly Tyr Gly Val Pro Pro Leu Asn Pro Leu Pro Val
        355                 360                 365

Pro Gly Val Ser Ser Ala Thr Leu Gln Gln Glu Asn Arg Ala Ala
    370                 375                 380

Gly Gln His Ile Thr Pro Leu Lys Lys Pro Leu His Ser Pro Gln Gly
385                 390                 395                 400

Leu Pro Leu Pro Leu Arg Pro Glu Thr Asn Phe Pro Gly Gly Gln Ala
                405                 410                 415

Pro Leu Gln Asn Pro Tyr Ala Tyr Ser Ser Gln Leu Pro Thr Ser Gln
            420                 425                 430

Leu Pro Pro Gln Gln Asn Ile Ser Arg Ala Thr Ala Pro Gln Thr Pro
        435                 440                 445

Leu Asn Ile Asn Leu Arg Pro Thr Thr Val Ser Ser Ala Thr Val Gln
    450                 455                 460

Phe Pro Pro Arg Ser Gln Gln Pro Leu Gln Lys Met Gln His Pro
465                 470                 475                 480

Pro Ser Glu Leu Ala Gln Leu Leu Ser Gln Thr Gln Ser Leu Gln
                485                 490                 495

Ala Thr Phe Gln Ser Ser Gln Gln Ala Ile Ser Gln Leu Gln Gln Gln
            500                 505                 510

Val Gln Ser Met Gln Gln Pro Asn Gln Asn Leu Pro Leu Ser Gln Asn
        515                 520                 525

Gly Arg Ala Gly Lys Gln Gln Trp Ala Gly Ser Ala Ile Pro Arg Val
    530                 535                 540
```

```
Ala Ser Thr Thr Gly Ser Thr Pro Val Ser Tyr Val Gln Thr Ala Ala
545                 550                 555                 560

Pro Ala Val Ser Gln Ser Val Gly Ser Val Lys Cys Thr Trp Thr Glu
            565                 570                 575

His Thr Ser Pro Asp Gly Phe Lys Tyr Tyr Asn Gly Leu Thr Gly
            580                 585                 590

Glu Ser Lys Trp Glu Lys Pro Glu Met Ile Val Phe Glu Arg Glu
            595                 600             605

Gln Gln Lys Gln Gln Gln His Gln Glu Lys Pro Thr Ile Gln Gln Ser
    610                 615                 620

Gln Thr Gln Leu Gln Pro Leu Gln Gln Pro Gln Gln Val Gln Gln
625                 630                 635                 640

Gln Tyr Gln Gly Gln Gln Leu Gln Gln Pro Phe Tyr Ser Ser Leu Tyr
                645                 650                 655

Pro Thr Pro Gly Ala Ser His Asn Thr Gln Tyr Pro Ser Leu Pro Val
            660                 665                 670

Gly Gln Asn Ser Gln Phe Pro Met Ser Gly Ile Gly Gln Asn Ala Gln
            675                 680                 685

(2) INFORMATION FOR SEQ ID NO: 27:

(i) SEQUENCE CHARACTERISTICS:
        (A) LENGTH: 72 amino acids
        (B) TYPE: amino acid
        (D) TOPOLOGY: linear (xi) SEQUENCE DESCRIPTION: SEQ ID NO: 27:

Met Asn Asp Pro Arg Ala Ser Asn Thr Asn Leu Ile Val Asn Tyr Leu
1               5                   10                  15

Pro Gln Asp Met Thr Asp Arg Glu Leu Tyr Ala Leu Phe Arg Ala Ile
            20                  25                  30

Gly Pro Ile Asn Thr Cys Arg Ile Met Arg Asp Tyr Lys Thr Gly Tyr
            35                  40                  45

Ser Phe Gly Tyr Ala Phe Val Asp Phe Thr Ser Glu Met Asp Ser Gln
    50                  55                  60

Arg Ala Ile Lys Val Leu Asn Gly
65                  70

(2) INFORMATION FOR SEQ ID NO: 28:

(i) SEQUENCE CHARACTERISTICS:
        (A) LENGTH: 78 amino acids
        (B) TYPE: amino acid
        (D) TOPOLOGY: linear (xi) SEQUENCE DESCRIPTION: SEQ ID NO: 28:

Pro Gly Gly Glu Ser Ile Lys Asp Thr Asn Leu Tyr Val Thr Asn Leu
1               5                   10                  15

Pro Arg Thr Ile Thr Asp Asp Gln Leu Asp Thr Ile Phe Gly Lys Tyr
            20                  25                  30

Gly Ser Ile Val Gln Lys Asn Ile Leu Arg Asp Lys Leu Thr Gly Arg
            35                  40                  45

Pro Arg Gly Val Ala Phe Val Arg Tyr Asn Lys Arg Glu Glu Ala Gln
    50                  55                  60

Glu Ala Ile Ser Ala Leu Asn Asn Val Ile Pro Glu Gly Gly
65                  70                  75
```

-continued (2) INFORMATION FOR SEQ ID NO: 29:

(i) SEQUENCE CHARACTERISTICS:
        (A) LENGTH: 77 amino acids
        (B) TYPE: amino acid
        (D) TOPOLOGY: linear (xi) SEQUENCE DESCRIPTION: SEQ ID NO: 29:

```
Ser Arg Glu His Pro Gln Ala Ser Arg Cys Ile Gly Val Phe Gly Leu
1               5                   10                  15

Asn Thr Asn Thr Ser Gln His Lys Val Arg Glu Leu Phe Asn Lys Tyr
                20                  25                  30

Gly Pro Ile Glu Arg Ile Gln Met Val Ile Asp Ala Gln Thr Gln Arg
            35                  40                  45

Ser Arg Gly Phe Cys Phe Ile Tyr Phe Glu Lys Leu Ser Asp Ala Arg
    50                  55                  60

Ala Ala Lys Asp Ser Cys Ser Gly Ile Glu Val Asp Gly
65                  70                  75
```

(2) INFORMATION FOR SEQ ID NO: 30:

(i) SEQUENCE CHARACTERISTICS:
        (A) LENGTH: 36 amino acids
        (B) TYPE: amino acid
        (D) TOPOLOGY: linear (xi) SEQUENCE DESCRIPTION: SEQ ID NO: 30:

```
Trp Lys Glu Ala Lys Asp Ala Ser Gly Arg Ile Tyr Tyr Tyr Asn Thr
1               5                   10                  15

Leu Thr Lys Lys Ser Thr Trp Glu Lys Pro Lys Glu Leu Ile Ser Gln
                20                  25                  30

Glu Glu Leu Leu
            35
```

(2) INFORMATION FOR SEQ ID NO: 31:

(i) SEQUENCE CHARACTERISTICS:
        (A) LENGTH: 36 amino acids
        (B) TYPE: amino acid
        (D) TOPOLOGY: linear (xi) SEQUENCE DESCRIPTION: SEQ ID NO: 31:

```
Trp Lys Glu Phe Met Ser Asp Asp Gly Lys Pro Tyr Tyr Tyr Asn Thr
1               5                   10                  15

Leu Thr Lys Lys Thr Gln Trp Val Lys Pro Asp Gly Glu Glu Ile Thr
                20                  25                  30

Lys Gly Glu Gln
```